US009907557B2

(12) United States Patent
Wallace et al.

(10) Patent No.: US 9,907,557 B2
(45) Date of Patent: *Mar. 6, 2018

(54) VASO-OCCLUSIVE DEVICES INCLUDING A FRICTION ELEMENT

(71) Applicant: STRYKER EUROPEAN HOLDINGS I, LLC, Kalamazoo, MI (US)

(72) Inventors: Michael P. Wallace, Pleasanton, CA (US); E. Skott Greenhalgh, Lower Gwynedd, PA (US)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 460 days.

This patent is subject to a terminal disclaimer.

(21) Appl. No.: 14/684,189

(22) Filed: Apr. 10, 2015

(65) Prior Publication Data

US 2015/0216530 A1    Aug. 6, 2015

Related U.S. Application Data

(63) Continuation of application No. 14/289,567, filed on May 28, 2014, now Pat. No. 9,011,482, which is a
(Continued)

(51) Int. Cl.
*A61M 29/00* (2006.01)
*A61B 17/12* (2006.01)
*A61B 17/00* (2006.01)

(52) U.S. Cl.
CPC .... *A61B 17/12113* (2013.01); *A61B 17/1214* (2013.01); *A61B 17/1215* (2013.01);
(Continued)

(58) Field of Classification Search
CPC ........ A61B 17/12031; A61B 17/12113; A61B 17/1214; A61B 17/1215; A61B 17/12163;
(Continued)

(56) References Cited

U.S. PATENT DOCUMENTS

| 4,754,685 A | 7/1988 | Kite et al. |
| 4,820,298 A | 4/1989 | Leveen et al. |

(Continued)

FOREIGN PATENT DOCUMENTS

| WO | WO 99/39646 A1 | 8/1999 |
| WO | WO 03/082363 A1 | 10/2003 |

(Continued)

OTHER PUBLICATIONS

Pyo et al.; Targeted gene disruption of matrix metalloproteinase-9 (Gelatinase B) suppresses development of experimental abdominal aortic aneurysms; J. Clinical Investigation; 105(11); pp. 1641-1649; Jun. 2000.

(Continued)

*Primary Examiner* — Gregory Anderson
(74) *Attorney, Agent, or Firm* — Vista IP Law Group, LLP

(57) ABSTRACT

Vaso-occlusive apparatuses, including implants, and methods of using them to treat aneurysms. The vaso-occlusive implants described herein include one or more soft and expandable braided member coupled to a pushable member such as a coil that maybe inserted and retrieved from within an aneurism using a delivery catheter as well as a friction element between the soft braided member and the coil. The friction element allows the relatively soft and elongate implant to be pushed out of a cannula without binding up within the cannula.

20 Claims, 37 Drawing Sheets

Related U.S. Application Data continuation-in-part of application No. PCT/US2013/000033, filed on Feb. 11, 2013.

(60) Provisional application No. 61/597,029, filed on Feb. 9, 2012, provisional application No. 61/721,367, filed on Nov. 1, 2012.

(52) U.S. Cl.
CPC .. *A61B 17/12031* (2013.01); *A61B 17/12163* (2013.01); *A61B 17/12168* (2013.01); *A61B 2017/00004* (2013.01); *A61B 2017/00367* (2013.01); *A61B 2017/00526* (2013.01); *A61B 2017/00884* (2013.01); *A61B 2017/00893* (2013.01); *A61B 2017/1205* (2013.01); *A61B 2017/12054* (2013.01); *A61B 2017/12063* (2013.01); *A61B 2017/12068* (2013.01); *A61B 2017/12095* (2013.01)

(58) Field of Classification Search
CPC .... A61B 17/12168; A61B 2017/00367; A61B 2017/1205; A61B 2017/12054
See application file for complete search history.

(56) References Cited

U.S. PATENT DOCUMENTS

| | | |
|---|---|---|
| 4,870,887 A | 10/1989 | Tresslar et al. |
| 4,994,069 A | 2/1991 | Ritchart et al. |
| 5,186,992 A | 2/1993 | Kite |
| 5,217,484 A | 6/1993 | Marks |
| 5,304,194 A | 4/1994 | Chee et al. |
| 5,382,259 A | 1/1995 | Phelps et al. |
| 5,423,849 A | 6/1995 | Engelson et al. |
| 5,536,274 A | 7/1996 | Neuss |
| 5,639,277 A | 6/1997 | Mariant et al. |
| 5,690,667 A | 11/1997 | Gia |
| 5,792,157 A | 8/1998 | Mische et al. |
| 5,888,201 A | 3/1999 | Stinson et al. |
| 5,891,191 A | 4/1999 | Stinson |
| 5,964,797 A | 10/1999 | Ho |
| 5,976,162 A | 11/1999 | Doan et al. |
| 6,019,786 A | 2/2000 | Thompson |
| 6,024,754 A | 2/2000 | Engelson |
| 6,066,158 A | 5/2000 | Engelson et al. |
| 6,096,052 A | 8/2000 | Callister et al. |
| 6,165,178 A | 12/2000 | Bashiri et al. |
| 6,187,027 B1 | 2/2001 | Mariant et al. |
| 6,193,728 B1 | 2/2001 | Ken et al. |
| 6,254,592 B1 | 7/2001 | Samson et al. |
| 6,287,318 B1 | 9/2001 | Villar et al. |
| 6,350,270 B1 | 2/2002 | Roue |
| 6,361,545 B1 | 3/2002 | Macoviak et al. |
| 6,458,119 B1 | 10/2002 | Berenstein et al. |
| 6,475,227 B2 | 11/2002 | Burke et al. |
| 6,551,340 B1 | 4/2003 | Kónya et al. |
| 6,589,256 B2 | 7/2003 | Forber |
| 6,592,617 B2 | 7/2003 | Thompson |
| 6,660,020 B2 | 12/2003 | Wallace et al. |
| 6,682,546 B2 | 1/2004 | Amplatz |
| 6,860,893 B2 | 3/2005 | Wallace et al. |
| 6,866,677 B2 | 3/2005 | Douk et al. |
| 6,872,218 B2 | 3/2005 | Ferrera et al. |
| 6,984,240 B1 | 1/2006 | Ken et al. |
| 6,994,689 B1 | 2/2006 | Zadno Azizi et al. |
| 7,066,946 B2 | 6/2006 | Douk et al. |
| 7,128,752 B2 | 10/2006 | Bales |
| 7,323,001 B2 | 1/2008 | Clubb et al. |
| 7,749,242 B2 | 7/2010 | Tran et al. |
| 7,828,816 B2 | 11/2010 | Mazzocchi et al. |
| 7,879,062 B2 | 2/2011 | Galdonik et al. |
| 8,002,789 B2 | 8/2011 | Ramzipoor et al. |
| 8,016,852 B2 | 9/2011 | Ho et al. |
| RE43,311 E | 4/2012 | Wallace et al. |
| 8,172,862 B2 | 5/2012 | Wallace et al. |
| 8,182,506 B2 | 5/2012 | Fitz et al. |
| 8,361,138 B2 | 1/2013 | Adams |
| 8,444,668 B2 | 5/2013 | Jones et al. |
| 8,486,104 B2 | 7/2013 | Samson et al. |
| 8,603,128 B2 | 12/2013 | Greene et al. |
| 9,011,482 B2 | 4/2015 | Wallace et al. |
| 9,060,777 B1 * | 6/2015 | Wallace ........... A61B 17/12113 |
| 2003/0093111 A1 | 5/2003 | Ken et al. |
| 2004/0098023 A1 | 5/2004 | Lee et al. |
| 2005/0222605 A1 | 10/2005 | Greenhalgh et al. |
| 2005/0277978 A1 | 12/2005 | Greenhalgh |
| 2006/0009799 A1 | 1/2006 | Kleshinski et al. |
| 2006/0030876 A1 | 2/2006 | Peacock et al. |
| 2006/0116709 A1 | 6/2006 | Sepetka et al. |
| 2006/0116713 A1 | 6/2006 | Sepetka et al. |
| 2008/0097401 A1 | 4/2008 | Trapp et al. |
| 2008/0109057 A1 | 5/2008 | Calabria et al. |
| 2009/0105748 A1 | 4/2009 | Fogarty et al. |
| 2009/0210047 A1 | 8/2009 | Amplatz et al. |
| 2009/0266366 A1 | 10/2009 | Swann et al. |
| 2009/0297582 A1 | 12/2009 | Meyer et al. |
| 2010/0063578 A1 | 3/2010 | Ren et al. |
| 2010/0152766 A1 | 6/2010 | Dieck et al. |
| 2011/0213405 A1 | 9/2011 | Porter et al. |
| 2013/0116722 A1 | 5/2013 | Aboytes et al. |
| 2013/0253572 A1 | 9/2013 | Molaei et al. |
| 2013/0267992 A1 | 10/2013 | Tran et al. |

FOREIGN PATENT DOCUMENTS

| | | |
|---|---|---|
| WO | WO 2004/045425 A1 | 6/2004 |
| WO | WO 2007/041624 A1 | 4/2007 |
| WO | WO 2007/123638 A1 | 11/2007 |
| WO | WO 2013/119332 A2 | 8/2013 |

OTHER PUBLICATIONS

Walton et al.; Inhibition of prostaglandin E2 synthesis in adominal aortic aneurysms; Circulation; pp. 48-54; Jul. 6, 1999.

Xu et al.; Sp1 increases expression of cyclooxygenase-2 in hypoxic vascular endothelium; J. Biological Chemistry; 275(32); pp. 24583-24589; Aug. 11, 2000.

* cited by examiner

| Braid | NiTi Size | Ends | Braid Angle On Mandrel | Mandrel O.D. (mm) | Pore size (um) | Pore area (mm^2) | Braid Angle in Catheter | Length of braid which is pushable(cm) |
|---|---|---|---|---|---|---|---|---|
| 1 | 0.00075" | 24 | 80 | 1 | - | - | 45 | 6 |
| 2 | 0.00075" | 24 | 53 | 1 | 184 | 0.034 | 40 | 8 |
| 3 | 0.00075" | 24 | 71 | 1.5 | 296 | 0.088 | 35 | 10 |
| 4 | 0.00075" | 24 | 51 | 1.5 | 332 | 0.11 | 30 | 15 |
| 5 | 0.00075" | 36 | 81 | 1.5 | 216 | 0.047 | 35 | 8 |
| 6 | 0.00075" | 36 | 51 | 1.5 | - | - | 25 | 15 |
| 7 | 0.00075" | 48 | 75 | 2 | 160 | 0.026 | 30 | 10 |
FIG. 10
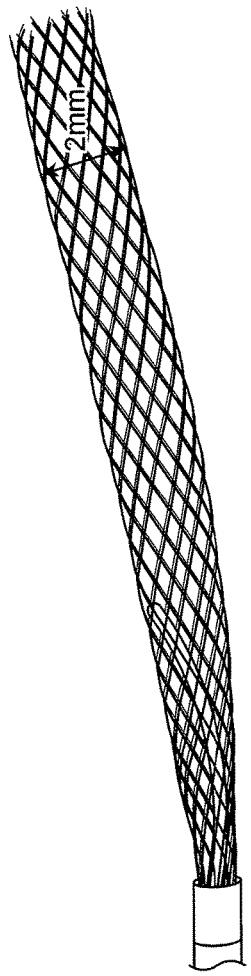
FIG. 11B
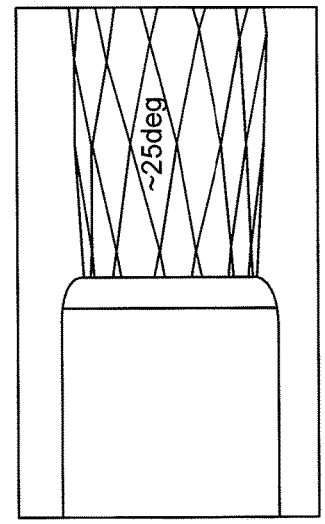
FIG. 11A

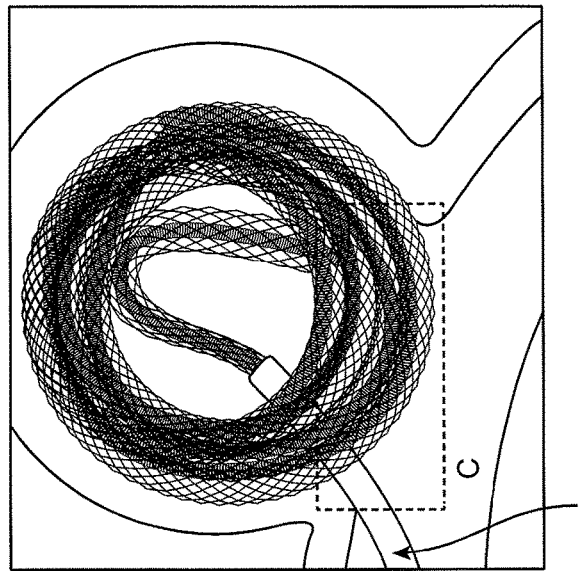
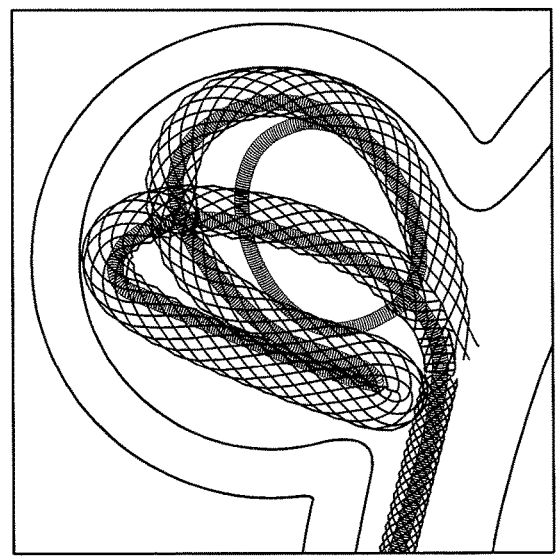
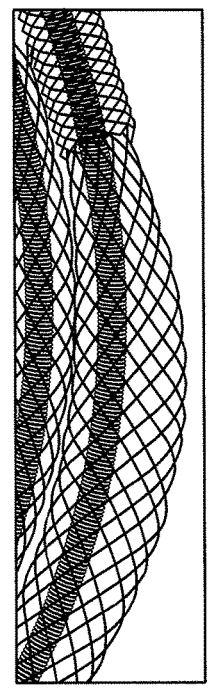
FIG. 14B
FIG. 14C
FIG. 14A
Catheter

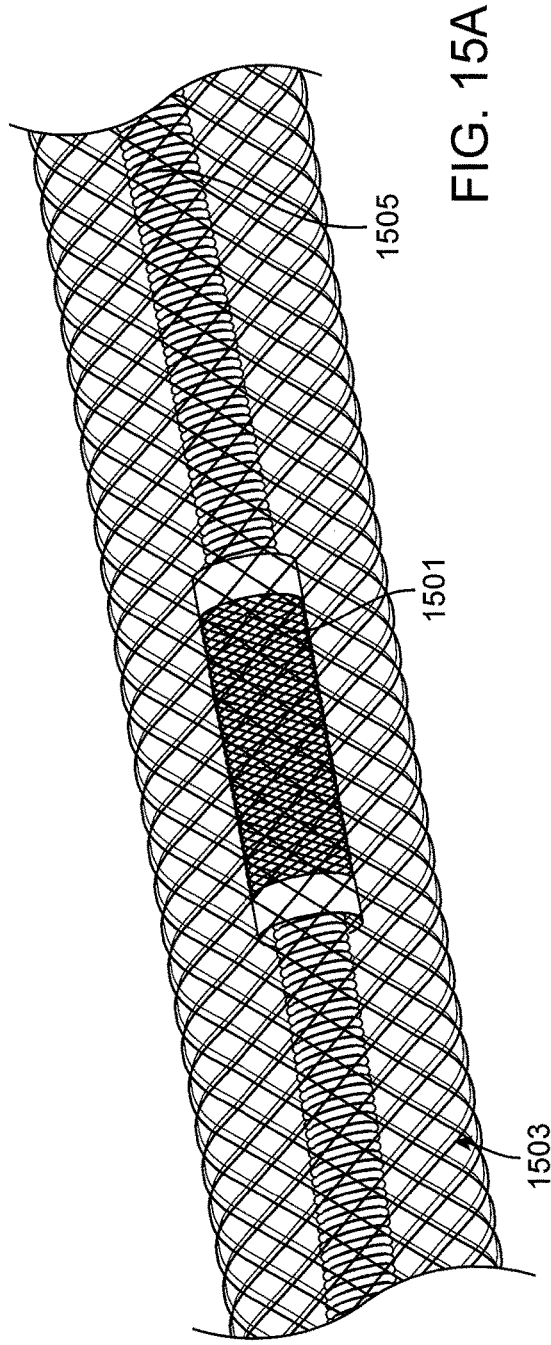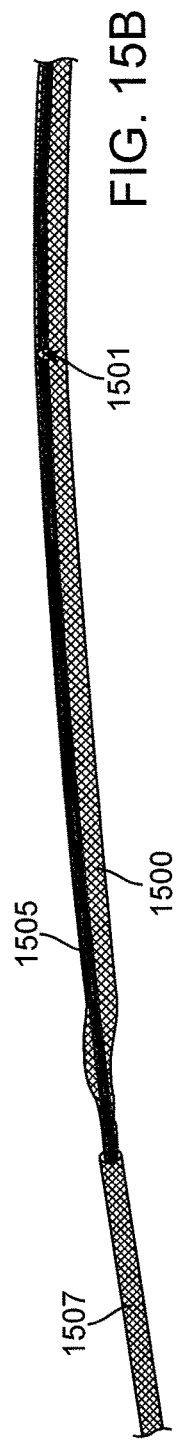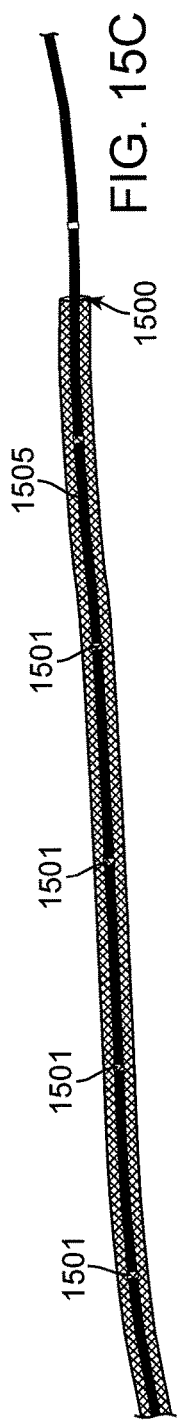
FIG. 15A
FIG. 15B
FIG. 15C

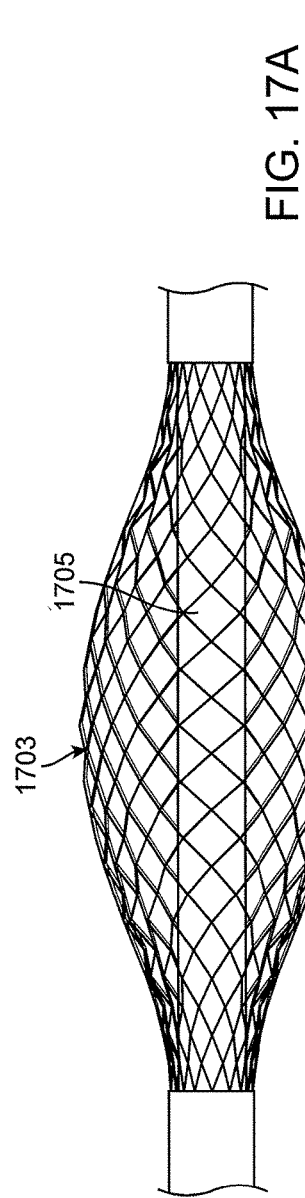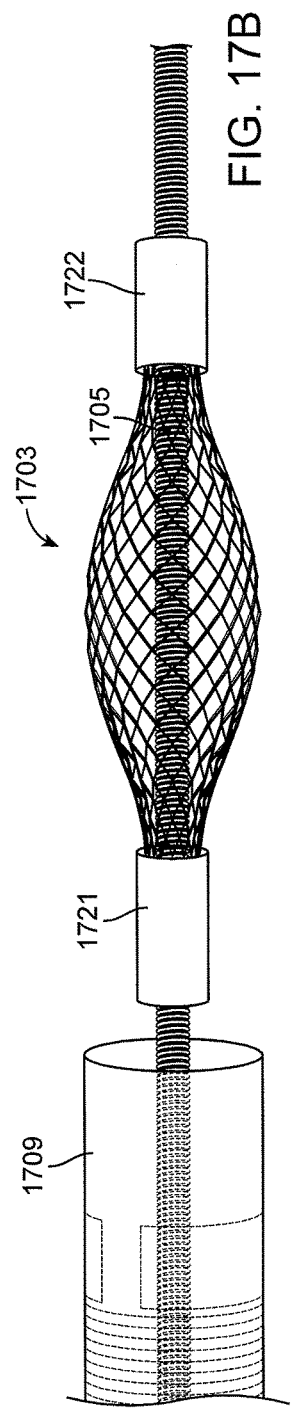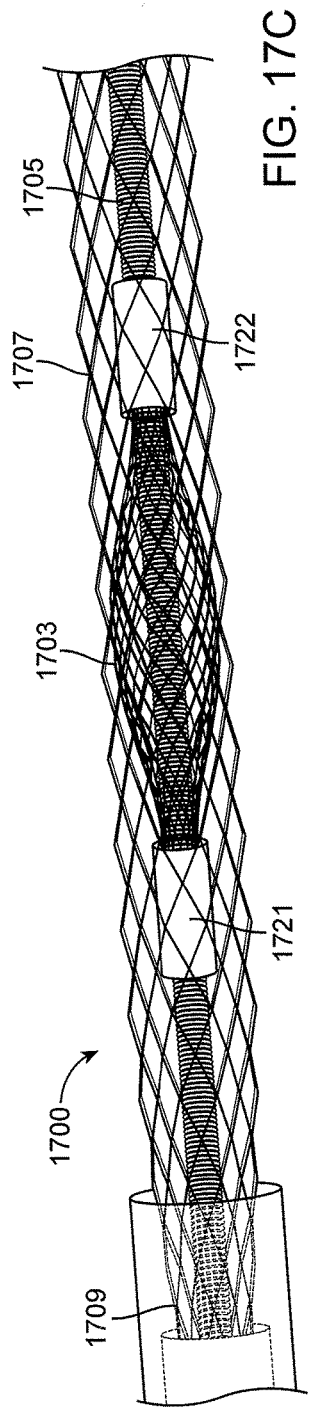

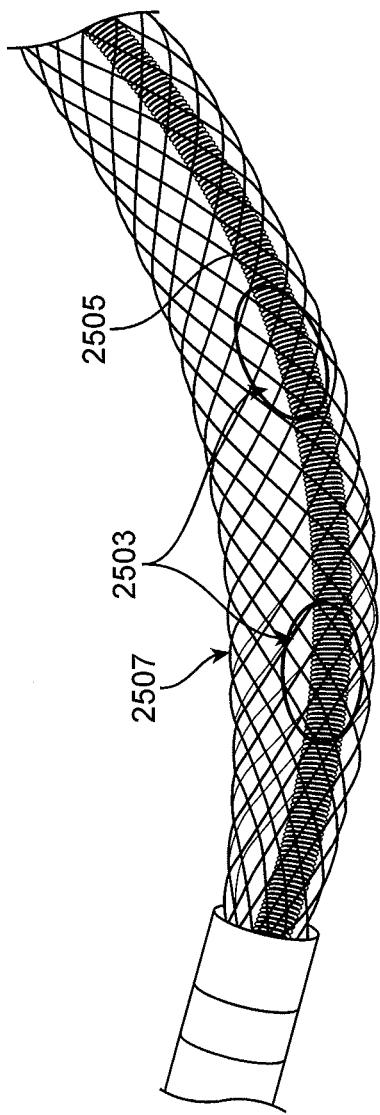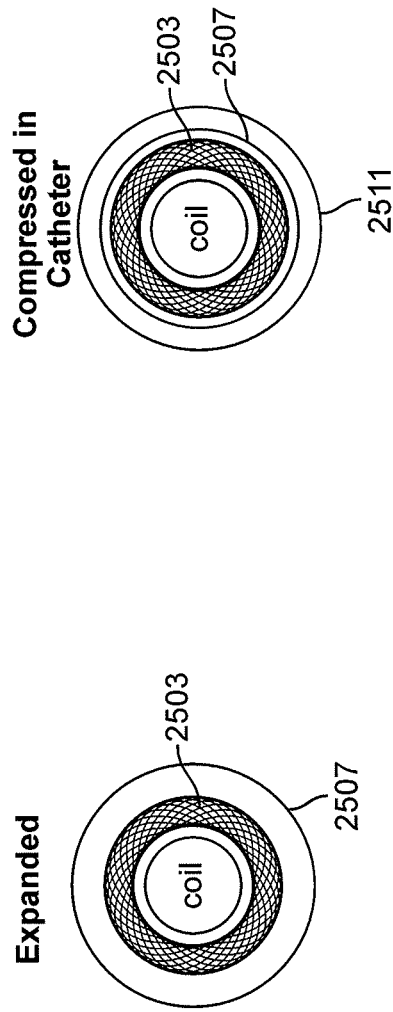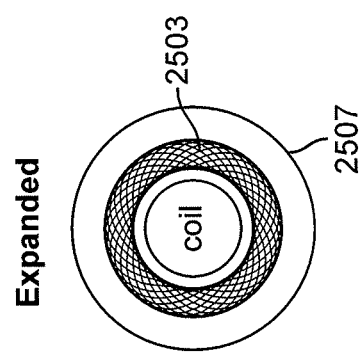

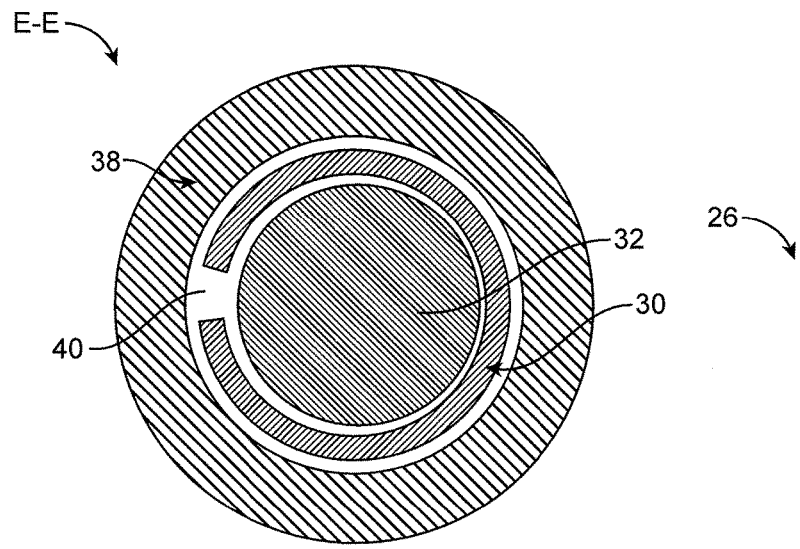
FIG. 27C
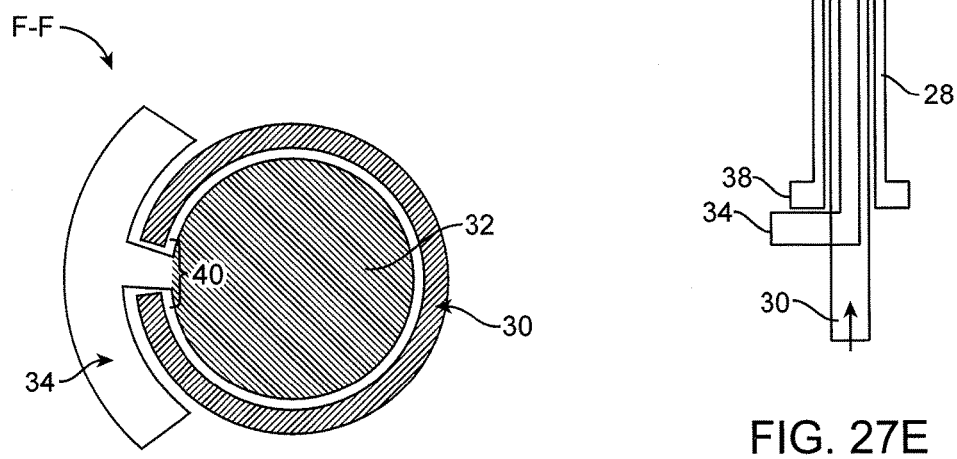
FIG. 27D
FIG. 27E

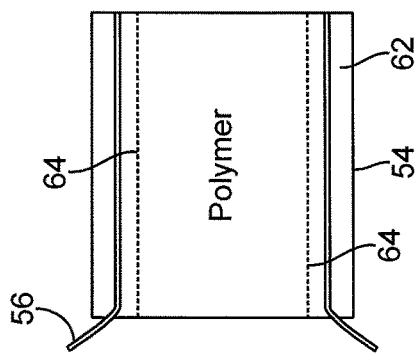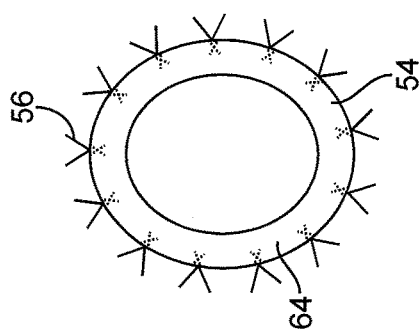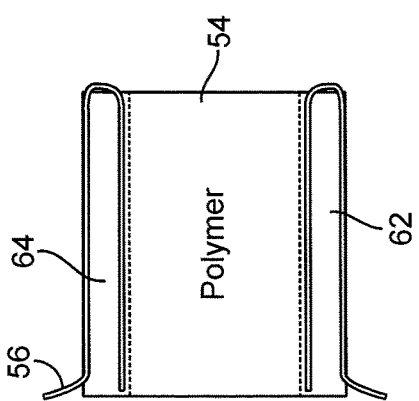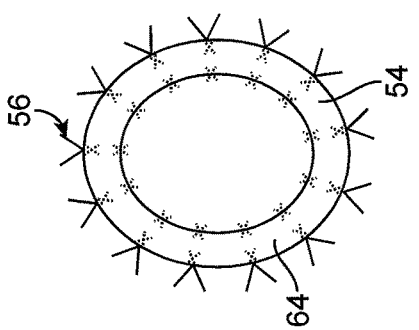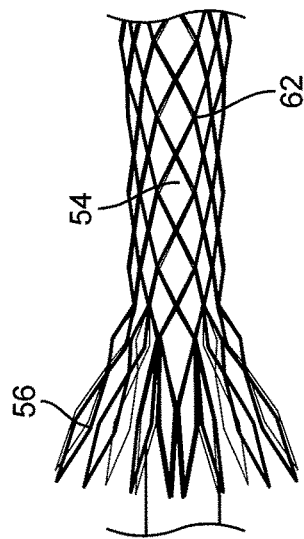
FIG. 34A
FIG. 34B
FIG. 33A
FIG. 33B
FIG. 33C

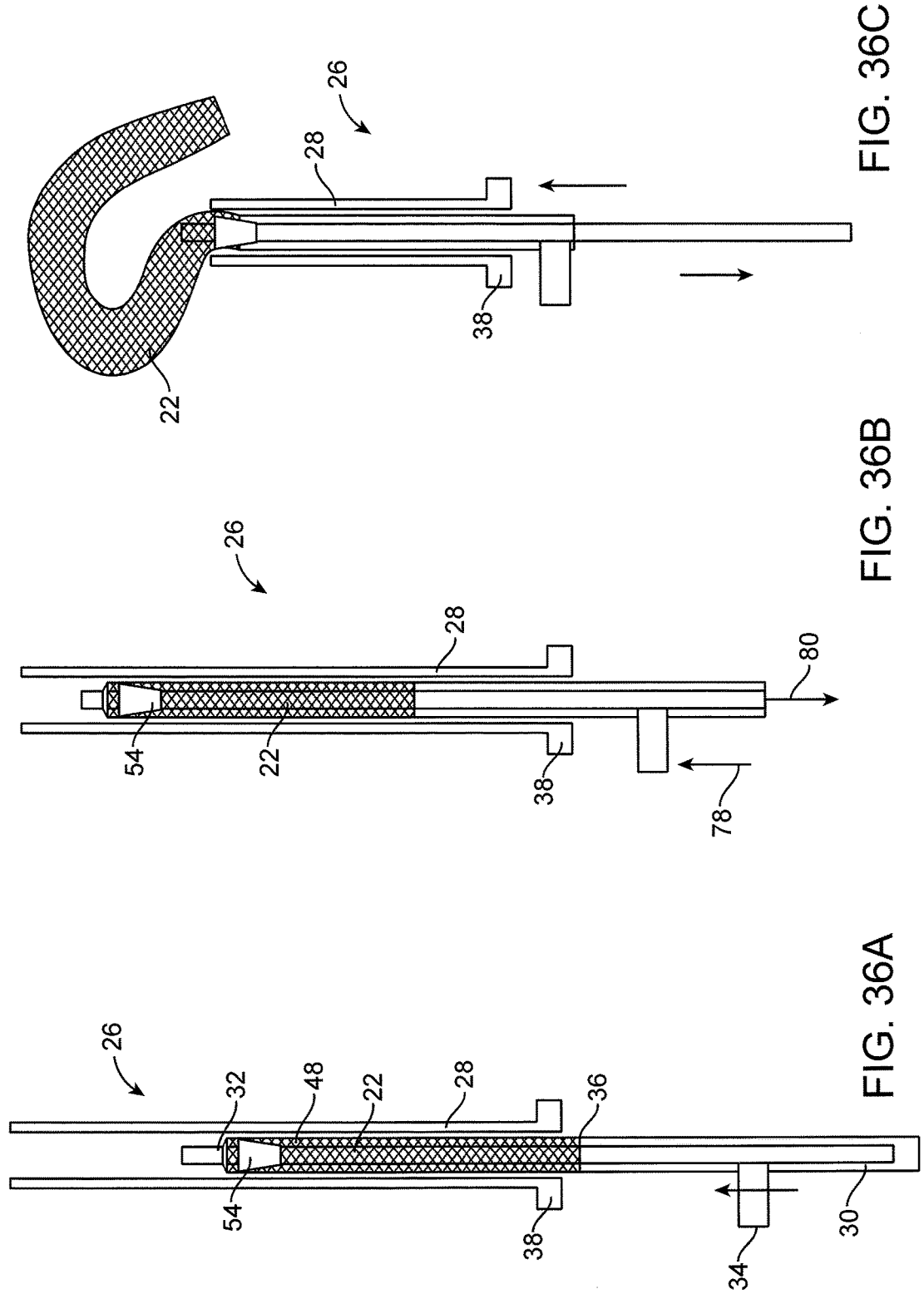

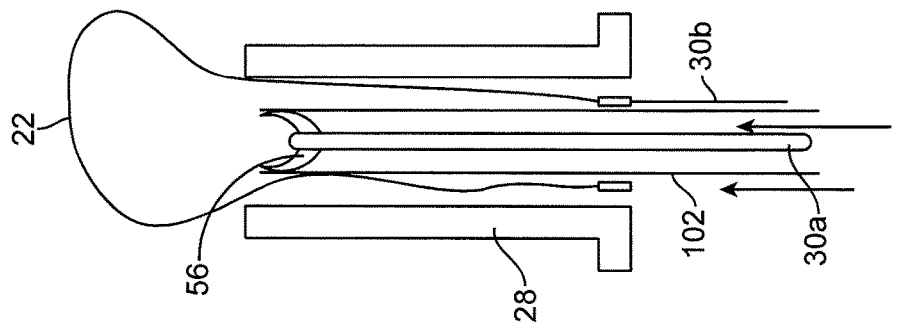
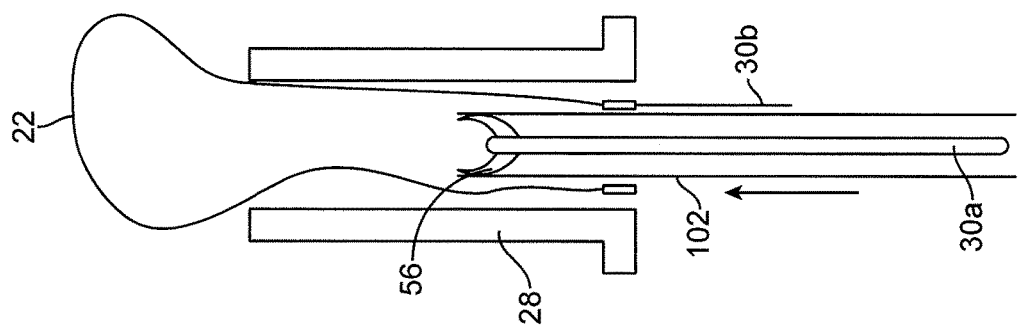
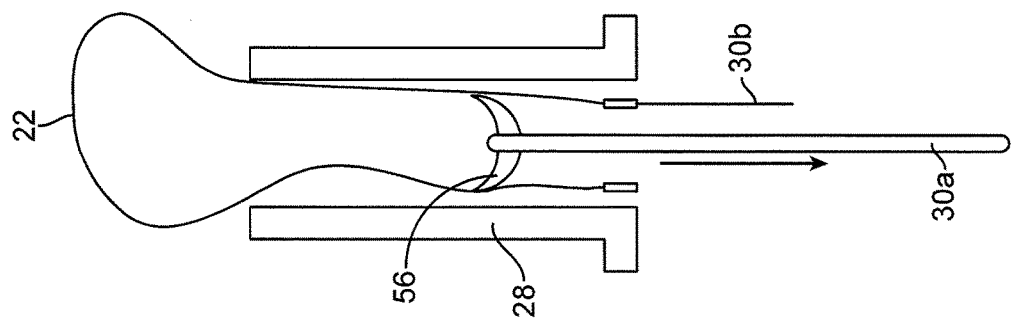
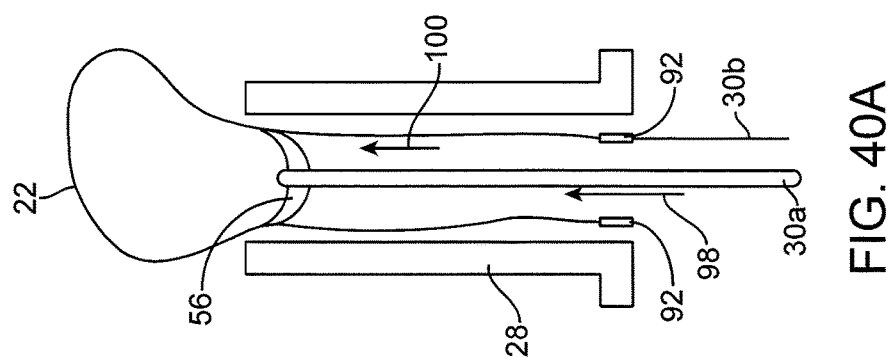

VASO-OCCLUSIVE DEVICES INCLUDING A FRICTION ELEMENT

CROSS REFERENCE TO RELATED APPLICATIONS

This patent application claims priority as a continuation of U.S. patent application Ser. No. 14/289,567, filed May 28, 2014, Publication No. US-2014-0277099-A1, which claims priority as a continuation-in-part to Patent Cooperation Treaty (PCT) international application no. PCT/US2013/000033, filed Feb. 11, 2013, which claimed priority to U.S. provisional patent applications: 61/597,029, filed Feb. 9, 2012 and 61/721,367 filed Nov. 1, 2012. Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are vaso-occlusive apparatuses (including embolic devices and systems) and method of making and using them. More specifically, described herein are pushable and retrievable vaso-occlusive apparatuses capable of locating with a high precision and including a highly expansive braid for use in vascular and particularly neurovascular applications.

BACKGROUND

An aneurysm is a dilation of a vessel, such as blood vessel, that may pose a risk to a patient's health due from rupture, clotting, or dissecting. For example, rupture of an aneurysm in a patient's brain may cause a stroke, and lead to brain damage and death. Cerebral aneurysms may be detected in a patient, e.g., following seizure or hemorrhage, and may be treated by applying vaso-occlusive devices, such as coils or stents. Coils that may be used to fill or embolize neurological aneurysms are typically made from platinum, and tend to be small coils or springs which can be shaped into a secondary shape of a more complex curve in order to help fill the aneurysm body. Unfortunately, currently used and proposed occlusive devices are difficult to position and remove, and present a risk of migration and resulting harm to the patient, particularly if they become dislodged from the site of insertion.

One type of neurovascular embolization stent coil device that has been proposed includes a central coil (e.g., metal coil) with a woven and/or braid material connected to the device. See, e.g., U.S. Pat. No. 7,749,242 ("the '242 patent"), which describes an expanding vaso-occlusive device including an expandable member attached to a central inner member on both ends of the expandable member but includes an internal "stop" attached to the central inner member. Similarly, U.S. Pat. No. 5,382,259 ("the '259 patent") describes vasoocclusion devices that may include a fibrous, woven or braided covering. Both the '259 patent and the '242 patent require that the woven, expandable outer members be relatively short and limited in expandability, otherwise they are difficult (if not impossible) to push and/or retrieve to/from a cannula. Unfortunately, small (short) coils are less desirable. Aneurysms with larger mouths are very difficult to treat, particularly with small and relatively thin coils. The coils may slip back out of the aneurysm sack. In addition, procedures using such small, thin, coils may require a longer and more involved procedure. For example, a 7 mm diameter neurological aneurysm may typically be filled with five to seven individual spring shaped coils, resulting in a longer and more complicated procedure than if the number of devices was reduced.

Described herein are braid-stent coil structures in which an expandable braided portion (which may be very long, e.g., 5 cm and longer) is connected to a pushable/pullable metal coil; the metal coil may provide a pushable core that may be used to position the braided expandable member. In the embodiments described herein, the tubular braided region may be fixed to the metal coil at only a single position, and be of great length and have an expanded diameter that is much larger than the diameter of the push coil, while still allowing the device to be pushed to insert from a catheter and pulled to retrieve into a catheter.

In addition to the implants (vaso-occlusive apparatuses), there is also a need for tools, including deployment tools, for deploying such devices. Accordingly, a deployment tool for delivering a soft, long stent-coil or other embolic device is desired. A deployment tool that can prevent longitudinal structural failure, buckling, and locking of the embolic device in the deployment catheter is also desired. A deployment tool that can retract and reposition the embolic device in the catheter is also desired. In addition to solutions for delivering a soft, long stent-coil which includes an inner core member such as a coil, a deployment tools is also desired to easily deploy, retrieved and detach a long, soft stent which has no core member.

SUMMARY OF THE DISCLOSURE

Described herein are vaso-occlusive devices that include a soft and expandable braid and a coil that maybe inserted and retrieved from within an aneurism using a delivery catheter, as well as delivery devices and methods of making an using them. Although this disclosure may be divided up into different sections describing different variations and embodiments, any of the features and elements described in any of the variations may be used as part of any of the other variations and embodiments.

For example, described herein are pushable and retrievable vaso-occlusive devices that include a coil and a soft tubular braid in which braid is attached at one end, e.g., a proximal end, coaxially around the inner coil and the opposite end of the braid, e.g., a distal end, is free-floating at the distal end. Such devices may be pushable within the catheter even though they include a relatively long (e.g., greater than 5 cm length) soft braided region that is collapsed when held within the catheter and expands to a diameter of more than one and a half times the diameter of the inner coil (e.g., more than: 2× the diameter of the inner coil, 2.5× the diameter of the inner coil, 3× the diameter of the inner coil, 3.5× the diameter of the inner coil, 4× the diameter of the inner coil, 4.5× the diameter of the inner coil, 5× the diameter of the inner coil, 5.5× the diameter of the inner coil, 6× the diameter of the inner coil, 7× the diameter of the inner coil, 8× the diameter of the inner coil, 9× the diameter of the inner coil, 10× the diameter of the inner coil, etc.).

As will be described in detail below, it has been extremely difficult to create devices having a soft, tubular braid of material that is attached at only one end to a pushable coil within a catheter in which the pushable material does not bind up within the catheter when pushing the device distally out of the catheter, particularly when the braided tube is bound only at the proximal end. Described in detail below are parameters that permit devices having such long, soft braided and expandable tubes coupled to a pushable inner member (e.g., coil) to be pushable, and also set forth examples that would not be pushable. Thus, described herein are systems including pushable implants having an inner member to which a soft, woven, and expandable out member is attached and a catheter from which the implant may be pushed (or retrieved).

For example, a vaso-occlusion system for occluding an aneurysm may include: a delivery catheter extending from a proximal end to a distal end; and a vaso-occlusive device within the delivery catheter, wherein the vaso-occlusive device is adapted to be pushed out of, and retrieved back into, the distal end of the delivery catheter, the vaso-occlusive device comprising: an elongate inner member having a diameter; an outer braided tubular member formed of about 36 strands or less, wherein the braided tubular member is attached to the inner member at a proximal end of the braided tubular member but is not attached at a distal end of the braided tubular member, further wherein the braided tubular member has a length that is greater than 5 cm, forms a braid angle of about 35 degrees or less when held within the delivery catheter, and expands to a diameter of greater than 1.5 times the diameter of the inner member when released from the delivery catheter.

A vaso-occlusion system may also include a pusher connected to the vaso-occlusive device.

In general, the braided tubular member may be made of any material that forms a relatively "soft" tube that can expand from a collapsed form having a first braid angle into an expanded having a diameter that is at least 1.5× greater than the diameter of the inner member. For example, the vaso-occlusive device braided tubular member may be formed of multiple strands of a monofilament, wire, or the like that forms multiple strand braided into the tubular shape. The strand (e.g., wire) may be any appropriate material, including metals, alloys, polymers, or the like. For example, the stands may be formed of a shape memory material (e.g., Nitinol), cobalt-chromium alloys, Pt, Pt-Iridium alloys, polymers (e.g., Nylon, Polyester, etc.) or combinations of these. The same material or different materials may be used to form the braided tubes of any of the variations described herein. Any appropriate diameter of strand may be used for form the braided tubes. For example, the strands may have a thickness that is less than about 0.0008 inches diameter. The diameter of the tube may be between about 0.0004 and about 0.00075 inches. In some variations, the strands forming the braided tube include a Nitinol wire having a thickness that is between about 0.0004 and 0.00075 inches diameter. In general, different wire diameters can be used in the same braided tube, and/or different combinations of materials can be used, i.e., Nitinol wire and Pt wires may be braided in the same tube. The braided tubes may be referred to as "woven" tubes.

The pushable member (e.g., the inner member in some variations) of the vaso-occlusion implant (apparatus) may be formed of any appropriate material. The pushable member (and therefore the entire implant) may generally be soft enough to be safely deployed in a fragile aneurysm. In general the pushable (e.g., inner) member has a column strength sufficient to allow pushing (and pulling) distally and proximally within a catheter, while still remaining sufficiently flexible to allow the implant to bend and/or form secondary or tertiary structures once pushed from the delivery device (e.g., catheter). For example, in some variations the pushable member is a coil, such as a closed-pitch coil. For example, an inner member (pushable member) comprises a closed pitch coil. The pushable member may be made of any appropriate material. For example, the pushable member may be a platinum coil.

Among the features that may be manipulated to aid in pushability of the implant including a soft and expandable braided member of greater than a predetermined length that are coupled with a pushable member are: collapsed/compressed braid angle (e.g., angle of the braid within a delivery device/catheter), number of strands forming the braid, expanded diameter of the braid (and/or the expanded braid angle of braid). Additional considerations that may affect pushability may include the outer diameter of the braid (e.g., the inner diameter of the catheter), the diameter of the strands forming the braid, and/or the smoothness of the braid. As described below, for a particular predetermined length of braid (e.g., greater than 5 cm), the ability of the device including a braid of the predetermined length to be pushable out of a catheter/delivery device may depend upon some or all of these factors. For example, with respect to collapsed braid angle, in some variations the braided tubular member comprises a braid angle of 30 degrees or less when held within the delivery catheter.

Any of the vaso-occlusion systems described may include an implant having a plurality of such 'pushable' elongate, soft and expandable braided tubular members that are connected sequentially along the pushable (e.g., inner) member. For example, an apparatus including a pushable inner member may include one (or more) braided tubular members that are attached to the inner member proximal to the first outer braided/braided tubular member. Different elongate, soft and expandable braided tubular members attached to the same pushable element may be of different lengths. For example, the distal-most elongate, soft and expandable braided tubular member may be of between about 5 and about 45 cm in length, while subsequent (more proximally) arranged braided tubular members may be shorter, or may alternate with longer and shorter lengths.

In general, the braided tubular member described herein may include any appropriate number of strands arranged into the braided tubular member. For example, a braided tubular member may have between about 24 and about 36 strands.

In general, the braided tubular member may be configured to have an expanded braid angle between about 35-90 degrees and a diameter between about 0.75 mm to about 3.0 mm. For example, the braided tubular member may be configured to have an expanded braid angle of less than about 50 degrees and a diameter between about 0.75 mm to about 3.0 mm.

The expandable braided tubular members described herein are typically porous, as they are expandable braids, but have a constrained pore-size formed by the braid. For example, the braided elongate tubes may have a pore size that is sufficiently small to prevent substantial blood flow (and particularly small enough to prevent passage of a clot) through the pores. For example, a braided tubular member may have a pore size formed between strands in the expanded configuration of less than about 0.1 square mm.

The braided tubular member may generally be configured to have a pre-set expanded diameter/transverse shape; this diameter may be circular or non-circular (e.g. oval, tear-shaped, etc.). In addition or alternatively, the braided tubular member may have a pre-set secondary or tertiary shape. For example, an elongate length of the vaso-occlusive device (including the braided member and/or the pushable member) may be configured to have a pre-set curve or shape (e.g., sinusoidal shape, curved shape, balled shape, etc.).

The proximal end of the braided tubular member may be coupled (e.g., bound) to the pushable member (e.g., an inner member) by any appropriate technique. For example, the braided tubular member may be bound to the pushable inner member by a polymeric junction or a metallic weld.

In addition to the minimum length of the soft and expandable and pushable braided tubular member (e.g., 5 cm), the braided tubular member may have a maximum length. For example, the braided tubular member may have a length that is less than about 45 cm. In a preferred embodiment, the length is between about 5 cm and about 30 cm.

Any appropriate delivery device may be used. For example, the delivery device may include a catheter having an inner diameter of between about 0.015 inches and about 0.025 inches. For example, the catheter may have an inner diameter of between about 0.015 inches and about 0.018 inches.

Also described herein are apparatuses (e.g., devices or implants) configured to be pushable out of a catheter as mentioned above. For example, a vaso-occlusion device for occluding an aneurysm, wherein the vaso-occlusion device comprises a collapsed configuration that is pushable out of a delivery catheter and an expanded configuration outside of the catheter, the vaso-occlusive device further includes: an elongate inner member having a diameter; and an outer braided tubular member formed of about 36 strands or less, wherein the braided tubular member is attached to the inner member at a proximal end of the braided tubular member but is not attached at a distal end of the braided tubular member, further wherein the braided tubular member has a length that is greater than 5 cm, forms a braid angle of about 35 degrees or less in the collapsed configuration within the delivery catheter, and expands to a diameter of greater than 1.5 times the diameter of the inner member in the expanded configuration when released from the delivery catheter.

Methods of using these apparatus are also described. For example, a method of occluding an aneurysm in a patient may include: inserting a catheter into the patient, wherein the catheter houses a vaso-occlusive device in a collapsed configuration within a lumen of the catheter, and the vaso-occlusive device comprises an elongate inner member having a diameter and an outer braided tubular member formed of about 36 strands or less, wherein the braided tubular member is attached to the inner member at a proximal end of the braided tubular member but is not attached at a distal end of the braided tubular member, further wherein the braided tubular member has a length that is greater than 5 cm, and the braided tubular member forms a braid angle of about 35 degrees or less in the collapsed configuration within the catheter; and pushing the vaso-occlusive device distally out of the catheter so that the braided tubular member expands to a diameter of greater than 1.5 times the diameter of the inner member in an expanded configuration when released from the delivery cannula.

In general, any of the implants described herein may be severable to a selectable or pre-selected length. For example, the pushable member may be mechanically, electrically, chemically or otherwise severable so that any appropriate length of implant may be inserted to an aneurysm. Thus, any of the methods described herein may include detaching a distal length of the vaso-occlusive device from the proximal end of the vaso-occlusive device.

As mentioned, any of the implants described herein may be retrieved/retrievable, including in particular retrievable back into the delivery apparatus (e.g., catheter). Thus, any of the methods of using these implants may include a step of retrieving at least a portion of the vaso-occlusive device that has been pushed out of the catheter back into the catheter by retracting the vaso-occlusive device proximally into the catheter. For example, a method of using them may include retrieving at least a portion of the vaso-occlusive device that has been pushed out of the catheter back into the catheter by retracting the vaso-occlusive device proximally into the catheter, and then again pushing the vaso-occlusive device distally out of the catheter.

As mentioned, any of these vaso-occlusive devices (implants) may be pre-biased in a curve so that it bends as it is pushed out of the catheter to assume three-dimensional shape. The device may include either or both a pre-biased tubular braid or a pre-biased pushable (e.g., inner) member.

In general, the apparatus may be positioned at or near the mouth of an aneurysm as part of the method of using the apparatus. For example, a method of occluding an aneurysm may include positioning a distal end region of the catheter adjacent an aneurysm in the body before pushing the vaso-occlusive device out of the catheter.

Once inserted, the device may limit the flow of blood. For example, a method of operating (e.g., method of occluding an aneurysm) may include limiting the flow of blood through the vaso-occlusive device when inserted into the patient after being pushed from the catheter by a small pore size formed between strands in the expanded configuration that are less than about 0.1 square mm.

Also described herein are vaso-occlusive implants having a soft and expandable braid that is arranged over an inner pushable member in which additional friction elements are included on either the braid and/or free-floating between the braid and the inner member. The friction elements are generally separated from the proximal and distal end regions of the outer tubular braid, but act to add friction between the outer braid and the inner pushable member over a portion of the length of the outer braid when the outer braid is collapsed over the inner member (e.g., in the delivery device/catheter). Although these friction elements may be used as part of the implants described above (e.g., implants having a soft, expandable, tubular braid member that is longer than 5 cm and is attached at one end, such as the proximal end, to the inner member and free-floating at the other end), in addition, friction elements may be used with any variation of implant including a soft, expandable, tubular braided member that is coaxially arranged over a pushable inner member.

For example, a vaso-occlusion system for occluding an aneurysm may include: a delivery catheter extending from a proximal end to a distal end; and a vaso-occlusive device within the delivery catheter, wherein the vaso-occlusive device is adapted to be pushed out of, and retrieved back into, the distal end of the delivery catheter, the vaso-occlusive device comprising: an elongate inner member having a length; an outer braided tubular member, wherein the braided tubular member has a length that is greater than 5 cm and has a collapsed configuration when held within the delivery catheter, and expands to a diameter of greater than 1.5 times the diameter of the inner member when released from the delivery cannula; and at least one friction element that is not attached to the inner member and is configured to contact both the inner member and the braided tubular member when the inner member is in the collapsed configuration when held within the delivery catheter so that the braided tubular member moves with the inner member when the vaso-occlusive device is pushed distally out of the delivery catheter.

In general, the friction element may be attached to the outer braided tubular member. For example, the friction element may be free-floating between the inner member and the outer braided tubular member when the vaso-occlusive device is out of the delivery catheter and the braided tubular member is expanded. Alternatively or additional, the friction element may be coupled/attached to the expandable braided tubular member. As mentioned, any number of friction elements may be included, and they may be arranged in any appropriate manner. For example, a plurality of friction elements may be positioned along the length of the inner member. The frictional elements may be arranged in a spiral or diagonal line along the length of the tubular member, and/or they may be arranged in a ring (e.g., in some variations with multiple rings along the length). For example, a plurality of friction elements may be positioned at radially offset positions around the inner member.

In some variations the friction elements comprises annular elements (e.g., rings or partial rings, e.g., U- or C-shapes).

In general, a frictional element is any element that may be positioned between the outer tubular member and the inner member to increase the friction between the outer member and inner member so that when the inner member is pushed within the delivery device/cannula the outer member is pushed along with it, preventing the outer expandable, soft braided member from being retained within the catheter as the implant is pushed distally (and/or pulled proximally). The inner frictional elements described herein may work exceptionally well where the friction between the outer tubular member and the delivery device/cannula inner diameter is low (or lower than the friction between the expandable outer braided tubular member and the inner member). Thus, at least the outer surface of the woven tubular member may be formed of a material or otherwise treated so that it has a low friction relative to the inside delivery device/catheter.

Any appropriate friction element may be used. The friction element may comprise a plastic, elastic or plastic and elastic material. For example, in some variations a friction element comprises a length of braided material having open proximal and distal ends.

Any of the previously described braided tubular portions may be used with the variations including frictional elements. For example, the braided member may be formed from a plurality of strands. The braided tubular material may be formed from a plurality of strands formed of a monofilament wire having a thickness that is less than about 0.0008 inches (e.g., a thickness that is between about 0.0004 and 0.0008 inches diameter). The braided tubular material may be formed from a plurality of strands and wherein the braided tubular member has between 24 and 48 strands. The braided tubular material may be formed from a plurality of strands, and wherein the braided tubular member is configured to have an expended braid angle between about 35-90 degrees and a diameter between about 0.75 mm to about 3.0 mm. The braided tubular material may be formed from a plurality of strands and wherein the braided tubular member has a pore size formed between strands in the expanded configuration of less than about 0.1 square mm. The braided tubular member may be configured to have a pre-set transverse shape that is non-circular. The elongate length of the vaso-occlusive device may be configured to have a pre-set curve.

The proximal end, distal end or distal and proximal end of the braided tubular member may be bound to the inner member. The braided tubular member may have a length that is less than about 30 cm. The catheter may have an inner diameter of between about 0.015 inches and 0.025 inches. The catheter may have an inner diameter of between about 0.015 inches to about 0.018 inches.

Also described are methods of occluding an aneurysm in a patient, the method comprising: inserting a catheter into the patient, wherein the catheter houses a vaso-occlusive device in a collapsed configuration within a lumen of the catheter, and the vaso-occlusive device comprises an elongate inner member having a length, an outer braided tubular member coaxial with the inner member and having a length that is less than the inner member and greater than 5 cm, and a friction element that is not attached to the inner member and is configured to contact both the inner member and the braided tubular member while the vaso-occlusive device is in the collapsed configuration within the delivery catheter, so that the braided tubular member moves with the inner member when the vaso-occlusive device is pushed distally out of the delivery catheter; and pushing the vaso-occlusive device distally out of the catheter by pushing the inner member, so that the braided tubular member expands to a diameter of greater than 1.5 times the diameter of the inner member in an expanded configuration when released from the delivery cannula.

As mentioned above, any of these methods may also include detaching a distal length of the vaso-occlusive device from the proximal end of the vaso-occlusive device. The method may also include retrieving at least a portion of the vaso-occlusive device that has been pushed out of the catheter back into the catheter by withdrawing the inner member proximally. The method may also include retrieving at least a portion of the vaso-occlusive device that has been pushed out of the catheter back into the catheter by withdrawing the inner member proximally, and then again pushing the vaso-occlusive device distally out of the catheter.

The vaso-occlusive device may be pre-biased in a curve so that it bends as it is pushed out of the catheter to assume three-dimensional shape. The method may also include positioning a distal end region of the catheter adjacent an aneurysm in the body before pushing the vaso-occlusive device out of the catheter.

The method may also include limiting the flow of blood through the vaso-occlusive device when inserted into the patient after being pushed from the catheter by a small pore sizes formed between strands in the expanded configuration that are less than about 0.1 square mm.

Also described herein are apparatus in which a soft, expandable tubular braided structure is non-concentrically attached to a pushable member and methods of making and using them.

For example, a vaso-occlusion system for occluding an aneurysm may include: a delivery catheter extending from a proximal end to a distal end; and a vaso-occlusive device within the delivery catheter, wherein the vaso-occlusive device is adapted to be pushed out of, and retrieved back into, the distal end of the delivery catheter, the vaso-occlusive device comprising: an elongate member having a diameter and a length; and a braided tubular member formed of a plurality of strands, wherein the elongate member is non-concentrically attached along a longitudinal side of the braided tubular member, further wherein the braided tubular member has a length that is greater than 5 cm; wherein the vaso-occlusive device has expands from a collapsed configuration in which the braided tubular member is compressed within the catheter to an expanded configuration having a diameter of greater than 1.5 times the diameter of the elongate member when released from the delivery cannula.

In some variations, the elongate member is positioned inside of the braided tubular member, e.g., attached, including attached at discrete locations, along one inner side of the braided tubular member. Alternatively, the elongate member is positioned outside and adjacent to the braided tubular member, e.g., attached, including attached at discrete locations, along one outer side of the braided tubular member.

In any of the systems described herein, the system may include a pusher connected to the vaso-occlusive device.

As mentioned above, any of the expandable, soft, braided tubular members described herein may be formed from a plurality of strands of any appropriate material. For example, the strands may comprise a monofilament wire having a thickness that is less than about 0.0008 inches diameter; the strands may comprise a Nitinol wire having a thickness that is between about 0.0004 inches and about 0.00075 inches diameter. In addition, any appropriate pushable member may be used, including an elongate member comprising a closed pitch coil, such as a 'soft' platinum coil. The braided tubular member may comprise a braid angle of 35 degrees or less in the collapsed configuration. The braided tubular member may have between 24 and 36 strands.

Additional (e.g., one or more) outer braided tubular members may be attached to the elongate member proximal to the outer braided tubular member. The braided tubular member may be configured to have an expended braid angle between about 35-90 degrees and a diameter between about 0.75 mm to about 3.0 mm in the expanded configuration. The braided tubular member may have a pore size formed between strands in the expanded configuration of less than about 0.1 square mm. The braided tubular member may be configured to have a pre-set transverse shape that is non-circular; an elongate length of the vaso-occlusive device may be configured to have a pre-set curve. The braided tubular member may be bound to the elongate member by a polymeric junction or a metallic weld. In general, the braided tubular member may have a length that is less than about 45 cm (e.g., less than 30 cm).

The system may include a catheter having an inner diameter of between about 0.015 inches and about 0.025 inches; e.g., the catheter may have an inner diameter of between about 0.015 inches and about 0.018 inches.

Also described herein are apparatus including one or more friction elements that are located on the pushable member (e.g., coil), instead or in addition to friction elements located on the soft, expandable tubular braided member and/or between the braided member and the pushable member.

For example, a vaso-occlusion system for occluding an aneurysm may include: a delivery catheter extending from a proximal end to a distal end; and a vaso-occlusive device within the delivery catheter, wherein the vaso-occlusive device is adapted to be pushed out of, and retrieved back into, the distal end of the delivery catheter, the vaso-occlusive device comprising: an elongate inner member having a length, wherein the length comprises a plurality of elongate regions having a first diameter separated by discrete regions having a second diameter that is greater than the first diameter but less than 1.5 times the first diameter, wherein the discrete regions form friction elements; an outer braided tubular member, wherein the braided tubular member has a length that is less than the length of the elongate inner member and greater than 5 cm, and has a collapsed configuration when held within the delivery catheter, and expands to a diameter of greater than 1.5 times the first diameter of the inner member when released from the delivery cannula; and wherein the friction elements are positioned along the length of the inner member proximal to the distal end of the outer braided tubular member and distal to the proximal end of the outer braided tubular member, and are configured to press the braided tubular member against the catheter when the inner member is in the collapsed configuration within the delivery catheter so that the braided tubular member moves with the inner member when the vaso-occlusive device is pushed distally out of the delivery catheter.

The elongate inner member may comprise a helical coil, including any of the pushable members described above. In some variations the elongate inner member may comprise a helical coil having regions of different diameter.

For example, described herein are vaso-occlusion systems for occluding an aneurysm comprising: a delivery catheter extending from a proximal end to a distal end; and a vaso-occlusive device within the delivery catheter, wherein the vaso-occlusive device is adapted to be pushed out of, and retrieved back into, the distal end of the delivery catheter, the vaso-occlusive device comprising: an elongate inner member having a length and a diameter; an outer braided tubular member, wherein the braided tubular member has a length that is less than the length of the elongate inner member and greater than 5 cm, and has a collapsed configuration when held within the delivery catheter, and expands to a diameter of greater than 1.5 times the diameter of the inner member when released from the delivery cannula; and a plurality of friction elements on the inner member at locations along the length of the inner member proximal to the distal end of the outer braided tubular member and distal to the proximal end of the outer braided tubular member, wherein the friction elements are configured to press the braided tubular member against the catheter when the inner member is in the collapsed configuration within the delivery catheter so that the braided tubular member moves with the inner member when the vaso-occlusive device is pushed distally out of the delivery catheter.

The friction element(s) may be configured as a bump on the inner member having a diameter of greater than about 1.2× the diameter of the inner member. The friction element(s) may comprise annular elements.

The friction elements may be made of any appropriate material, including, for example, plastic, elastic or plastic and elastic materials.

The system may include a pusher connected to the vaso-occlusive device.

In general, the braided tubular member may be any of the braided tubular members described herein, including for example braided tubular members formed from a plurality of strands. For example, the braided tubular material may be formed from a plurality of strands formed of a monofilament wire having a thickness that is less than about 0.0008 inches diameter. The braided tubular material may be formed from a plurality of strands of Nitinol wire having a thickness that is between about 0.0004 inches and about 0.00075 inches. The braided tubular material may be formed from a plurality of strands, further wherein the braided tubular member may comprises a braid angle of 30 degrees or less in the collapsed configuration. The braided tubular material may be formed from a plurality of strands and wherein the braided tubular member has between 24 and 48 strands. The braided tubular material may be formed from a plurality of strands, wherein the braided tubular member is configured to have an expended braid angle between about 35-90 degrees and a diameter between about 0.75 mm to about 3.0 mm. The braided tubular material may be formed from a plurality of strands and wherein the braided tubular member has a pore size formed between strands in the expanded configuration of less than about 0.1 square mm. The braided tubular member is configured to have a pre-set transverse shape that is non-circular. The braided tubular member may have a length that is less than about 45 cm.

The inner member may be any of the pushable members described herein, including, for example, pushable members comprising a closed pitch coil. The inner member may comprise a platinum coil. The catheter may have an inner diameter of between about 0.015 inches and about 0.025 inches. The catheter may have an inner diameter of between about 0.015 inches and about 0.018 inches.

The elongate length of the vaso-occlusive device may be configured to have a pre-set curve.

The proximal end, distal end or distal and proximal end of the braided tubular member may be bound to the inner member.

BRIEF DESCRIPTION OF THE DRAWINGS

FIG. 10 is a table summarizing the results of tests performed to determine pushability of implants having braided members of various configurations.

FIGS. 11A and 11B illustrate an example of a vaso-occlusive device (implant) that includes a soft, elongate, braided outer member that is pushable.

FIGS. 14A-14C illustrate the insertion of a vaso-occlusive device with a soft, elongate, braided outer member inserted into a model (e.g., silicone) aneurysm.

FIG. 15A illustrates one example of a portion of a vaso-occlusive device having a friction element attached to a pushable inner member portion of the implant.

FIGS. 15B and 15C illustrate implants including the friction element shown in FIG. 15A.

FIG. 17A is an example of another friction element that may be used as part of a vaso-occlusive implant.

FIGS. 17B and 17C show the friction element of FIG. 17A attached to a pushable member of an implant and as part of an implant including an outer braided member, respectively.

FIG. 25A is an example of a vaso-occlusive implant including a floating frictional element between the outer braided member and an inner pushable member of the implant.

FIGS. 25B and 25C show schematics of sectional views of the implant of FIG. 25A in an expanded and compressed configuration, respectively.

In FIG. 26A the pushable member is connected along the outer surface of the expandable braided member, while in FIG. 26B the pushable member is connected along an inner side of the expandable braided member.

FIGS. 27A, 27B, 27E and 27F illustrate a method of deploying a vaso-occlusive device (embolic device) with a variation of a deployment tool. FIGS. 27C, 27D are variations of cross-sections E-E and F-F, respectively of FIG. 27B.

FIGS. 28A, 28B, 28C and 28D illustrate a method of deploying the embolic device with a variation of the deployment tool.

FIGS. 33A and 33B are front and side views, respectively of a variation of the flare and the braided member, and FIG. 33C is a side view of the flare on a mandrel or core.

FIGS. 34A and 34B are front and side views, respectively, of a variation of the flare and the braided member.

FIGS. 36A-36C illustrate a method of deploying the embolic device with a variation of the deployment tool.

FIGS. 40A-40D illustrate a method of using a variation of the deployment tool.

DETAILED DESCRIPTION

Figure 2B:
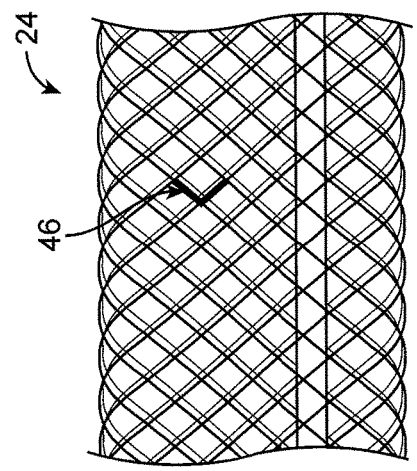
FIGS. 2A and 2B are close-up views of variations of the braided embolic devices.

In general, described herein are vaso-occlusive devices that may be delivered into an aneurysm where they can expand to fill the aneurysm. These apparatuses may include an implant having an elongate (and severable) pushable member, such as a soft metallic or polymeric coil attached to an elongate soft, expandable and braided tubular member that either co-axially surrounds the pushable member or is adjacent to the pushable member. These implants may be held within a delivery device so that the relatively long (e.g., longer than 5 cm) braided tubular member is in a collapsed configuration within the lumen of the delivery member (e.g., catheter). Although in general it is difficult, if not impossible, to push an elongate (>5 cm) expandable braided member distally or proximally from with a lumen, described herein are embodiments that are adapted to be pushable so that they can be delivered by pushing from a delivery device and retrieved back into the delivery device, and expand to 1.5× or more than the delivery diameter and/or the diameter of the pushable member of the implant. In particular, described herein are vaso-occlusive implants having a pushable inner member to which an elongate (e.g., longer than 5 cm), soft, expandable braded member is attached at just one end of the braided member, where the braid member is constructed from a specific design to make it more pushable inside the delivery catheter, thereby preventing the braid from collapsing or bunching up during delivery to the desired anatomical site. Also described herein are apparatuses in which the implant includes one or more friction elements either or both attached to the braided member or between the braided member and the pushable member. Also described herein are apparatuses in which the pushable member is adapted to include friction elements along the length between the distal and proximal ends of the braided outer member. Finally also described herein are apparatuses in which the braided outer member and the pushable member are coupled off-axis relative to each other. Any of these variations may be combined or adapted to include any of the other features of these embodiments, unless the context indicates otherwise. Methods of making and using these apparatuses are also described, and particularly methods of using any of these apparatuses to treat (e.g., occlude) an aneurysm.

In general, a vaso-occlusive implant includes a pushable member and a braided member. A pushable member may include a coil, wire, tendon, or the like, having a sufficient column strength to permit pushing of the implant into an aneurysm body. The pushable member may be "soft", i.e., may be made from a soft material such as platinum. In any of these variations the pushable member may be a coil, such as a platinum coil. In variations in which the pushable member is at least partially surrounded by the expandable braided member, the pushable member may be referred to as an inner member or inner coil. Although coils may be preferred, they are not required to form the pushable member. For example, a pushable member may be formed or a non-coiled wire or the like.

In general, a braided member may be formed of any number of filaments ("strands") that are woven or braided together to form a braided tube of the desired length (e.g., greater than 5 cm, between 5 cm and 45 cm, between 5 cm and 30 cm, etc.). The strands are typically monofilaments but also can be multifilament strands, and may be formed of any appropriate material, including, but not limited to, metals (including alloys) and polymers (both natural and synthetic) or the like. For example, the strands may be a shape memory material such as Nitinol, or the like (examples are provided below). Braided strands may be formed using braiding machines, and strands may be braided around a mandrel in a continuous fashion. Braids can also be formed over a three-dimensional mandrel in a non-continuous fashion. If the strands are braided over a mandrel (e.g., a mandrel having a round, oval, flat or other shape) it may form a "tubular braid". Alternatively, strands can be woven into a flat sheet and subsequently formed & heat set around a mandrel to form a "woven tubular" construct. For the purpose of this specification the term woven tube and braided tube may be used interchangeably and be inclusive of the constructs described above.

The braided members are typically expandable from a collapsed tubular configuration into an expanded tubular configuration, in which the diameter of the braided member expands from a first diameter to a second (expanded) diameter that is typically greater than 1.5× the collapsed diameter (e.g., 2× the collapsed diameter, 2.5× the collapsed diameter, 3× the collapsed diameter, etc.). The number of strands ("ends") may be between about 12 and about 48, but more preferably between about 24 and 36. The strands may be formed into the braided tube shape by being braided over a mandrel.

Figure 1B:
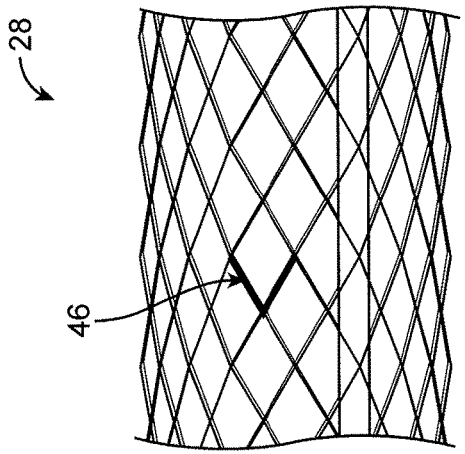
FIGS. 1A and 1B are close-up views of a variation of braided embolic devices as described herein.
Figure 1A:
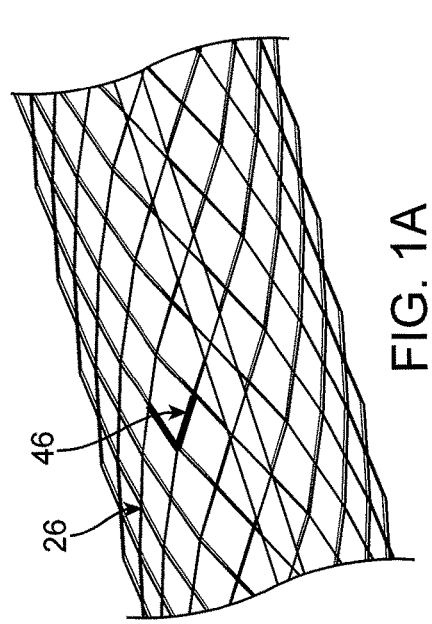

FIGS. 1A-1B and 2A-2B illustrate variations of a braided member that is positioned over a pushable (inner) member. In FIG. 1A, the implant ("embolic device") has a braided member with a braid angle 46. In general, a braid angle 46 can be the angle between two crossing filaments or fibers viewed along the direction of the longitudinal axis. FIG. 1A shows an implant in which the braid angle 46 is apparent when the braided member of the implant 22, 24 is in a radially contracted configuration (e.g., when loaded in a catheter). In this example, the braid angle is between about 20° to about 30°. The braid angle 46 when the device is in a radially expanded configuration (e.g., when deployed out of a catheter) can be from about 40° to about 80°, for example about 50°. In FIG. 1A the fibers or filaments can be 0.0008 in. metal (e.g., Nitinol) wires heat set on a manufacturing mandrel having a diameter of about 1 mm. FIG. 1B shows an example of another implant in which the strands forming the braided member are slightly larger diameter than in FIG. 1A.

Figure 2A:
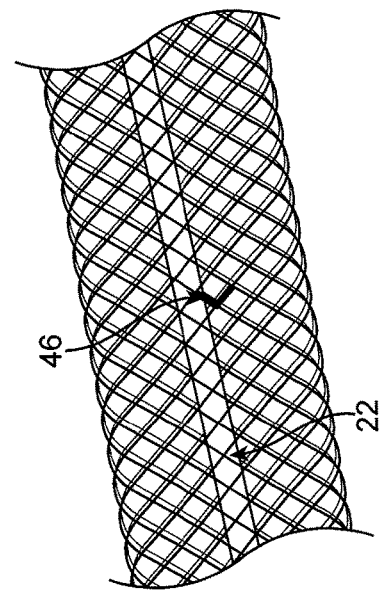

FIGS. 2A and 2B illustrate an embolic device 26, 28 having a braid angle 46 in a radially expanded configuration. In FIG. 2A, the braid angle has expanded to between about 100° to about 110°. When the device 22, 24 is in a radially contracted configuration, the braid angle 46 can be from about 50° to about 70°. A deployment tools can deploy, retrieve and reposition an implant (embolic device, e.g., a stent-coil) fabricated with small or large braid angles. The deployment tools can push the stent-coil braid structure inside a catheter and into an aneurysm. For example, the proximal end of a 12 cm long, braided embolic device 22 having a collapsed braid angle 46 of about 20° (e.g., as shown in FIGS. 1A and 1B) can be pushed inside a 0.021" ID catheter.

Figure 3:
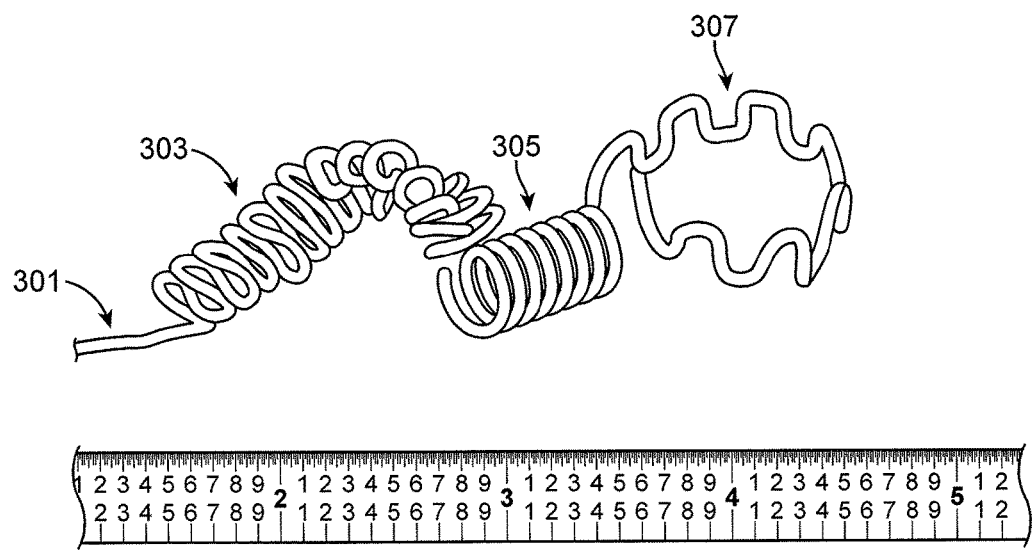
FIG. 3 illustrates a braided member of an embolic device (implant) having various pre-set shapes.

Any of the devices described herein may also be configured so that the implant includes a pre-set configuration that is bent, curved, or three-dimensional (e.g., balled-up, looped, etc.). Either or both the pushable member and/or the braided member may be pre-set to include a secondary or tertiary structure when expanded outside of the delivery device/catheter. For example, FIG. 3 illustrates a coil having a plurality of different pre-set shapes. In FIG. 3, the braided member includes a non-preset length (straight length 301), a figure-8 bent region, a coiled region 305 and a sine-curved length 307. Any one or more of these pre-set shapes may be used for the braided member and/or pushable member.

Figure 4A:
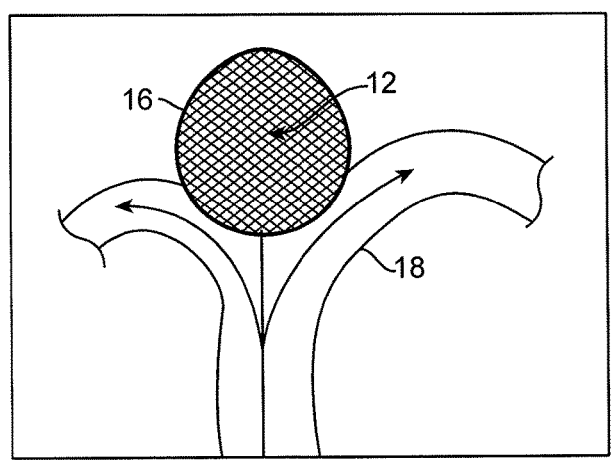
FIGS. 4A and 4B illustrate the use of coils in aneurysms.
Figure 4B:
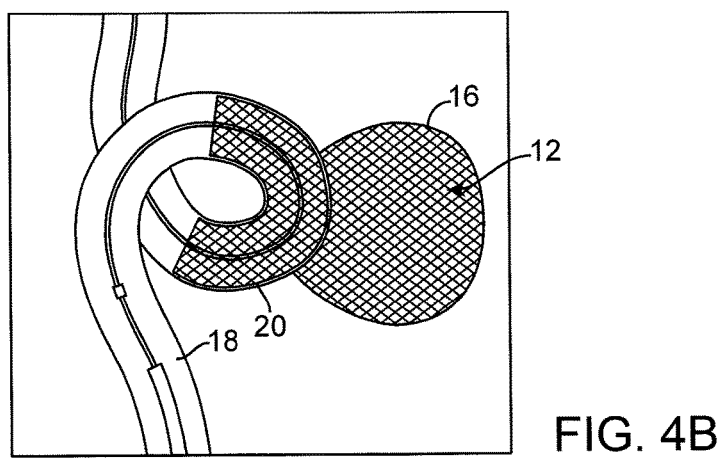

In use, any of the implants described herein may be inserted into an aneurysm in order to occlude the aneurysm. Stents, including stent coils, for occluding an aneurysm are known, as illustrated in FIGS. 4A and 4B, which illustrate the use of prior art stent coils to fill an aneurysm. In these examples the implants described herein, which include an expandable braided member, may have numerous advantages compared to existing stent coils for filling aneurysm. In particular the soft, expandable coils may be between about 6-15 times greater at volume filing, and may allow flow diverting for both ruptured an un-ruptured aneurysms. This may allow for a reduction in the number of coils required per aneurysm as well as shorter procedures (and therefore reduced radiation exposure) for patients. This may also result in a reduced risk of aneurysm recanalization, and the patient may not require a long (or indefinite) course of anti-platelet medications or blood thinners.

In general, any of the implants described herein may be inserted into a patient by inserting (e.g., minimally invasively), a catheter/insertion device into the patient's vasculature to reach the aneurysm site. At the aneurysm site the implant may be pushed distally out of the catheter/insertion device and delivered into the aneurysm body. After being extruded from the catheter/insertion device, the implant, and particular the braided portion, may self-expand into the expanded configuration, and the implant may also assume a pre-set configuration as described above. Sufficient implant may be inserted to fill and occlude the aneurysm. In the expanded configuration the pores (gaps between the strands forming the braided tubular member, may be sufficiently small, e.g., less than 0.1 mm$^2$, and preferable less than about 0.06 mm$^2$, to prevent passage of clots, etc. Once sufficient implant has been inserted, the implant may be severed (or predefined lengths may be inserted) to fill the aneurysm. The implant may also be removed or withdrawn, and collapsed back into the delivery device/catheter, by withdrawing the implant proximally.

Part I: Pushable Braided Regions

A vaso-occlusive pushable and retrievable apparatus (e.g., implant) may include a pushable inner member (e.g., coil) and a soft, expandable, tubular braided member which braid is attached at one end, e.g., a proximal end. The braided member typically has a length that is greater than 5 cm, and a plurality of these braided members may be positioned along the length of the inner member so that each braided member is coaxially positioned around the inner coil. One end of the braided member is typically free or loose (allowing maximal expansion) while the opposite end is coupled/attached to the inner member. Thus, the distal end of the braided member is free-floating at the distal end.

Such devices may be pushable within the catheter even though they include a relatively long (e.g., greater than 5 cm length) soft braided region that is collapsed when held within the catheter and expands to a diameter of more than one and a half times the diameter of the inner coil (e.g., more than: 2× the diameter of the inner coil, 2.5× the diameter of the inner coil, 3× the diameter of the inner coil, 3.5× the diameter of the inner coil, 4× the diameter of the inner coil, 4.5× the diameter of the inner coil, 5× the diameter of the inner coil, 5.5× the diameter of the inner coil, 6× the diameter of the inner coil, 7× the diameter of the inner coil, 8× the diameter of the inner coil, 9× the diameter of the inner coil, 10× the diameter of the inner coil, etc.).

Figure 5:
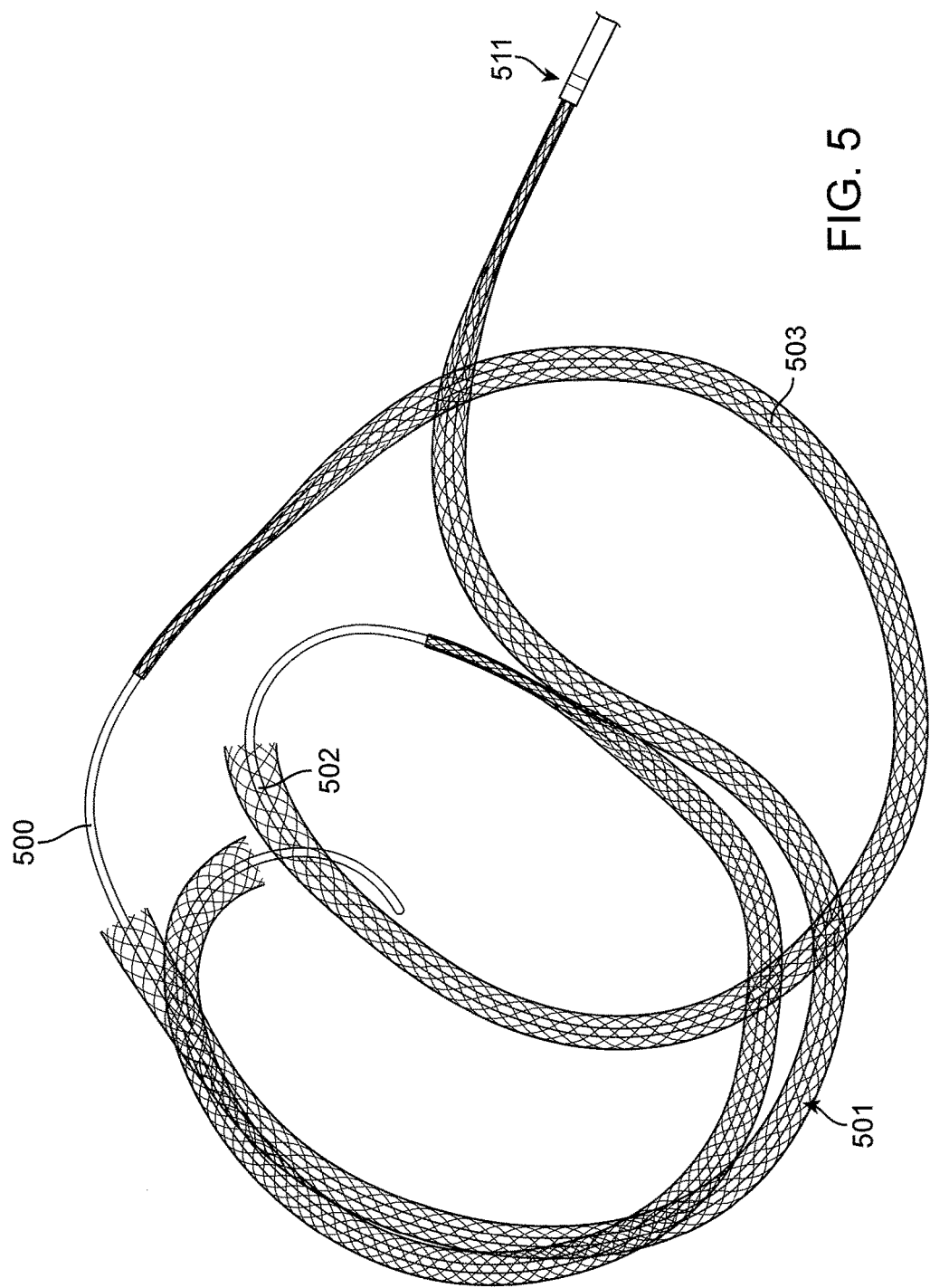
FIG. 5 shows one example of a vaso-occlusive device (implant or embolic device) having a pushable inner member and a plurality of soft, elongate, braided members that are attached to the inner member at only a proximal location.

FIG. 5 illustrates one example of an implant having a pushable inner member 500 and a plurality of outer, braided members 501, 502, and 503. Dashed lines 1, 2 and 3 trace the path of the braided member over the inner member of braided members 501, 502 and 503, respectively. In FIG. 5, the implant is a 20 cm coil with three 6 cm long braided members (having a 1 mm OD). This example is very pushable even when held within a catheter 511, and is retrievable. As shown, the proximal end of each braided member is bound to the inner member over a portion of the length, while the expanded portion of the braided member is otherwise unconnected to the inner member, and the loose end is free to expand.

These implants are pushable when held within a catheter or other delivery device, even catheters/delivery devices having extremely narrow inner diameters (e.g., between about 0.015 inches and about 0.025 inches, or between about 0.015 inches and about 0.018 inches), and even when the length of the braided region is >5 cm (e.g., between about 5 cm and about 30 cm). This may be accomplished by controlling the number of strands for the braid, the braid angle, and/or the expanded configuration, relative to the collapsed configuration. For example, in any of the implants having a free-floating end with a length of greater than 5 cm, it may be advantage to allow pushability with a catheter/delivery device by having a braid angle that is less than about 35 degrees (e.g., less than about 34°, less than about 33°, less than about 32°, less than about 31°, less than about 30°, less than about 29°, less than about 28°, less than about 27°, less than about 26°, less than about 25°, etc.), as measured inside of the delivery catheter/delivery device.

These factors may enhance pushability by preventing collapse of braid, which could otherwise result in bunching of braid in catheter when pushing and cause jamming of the implant in the catheter.

Although braided members that could be made with shorter braid sections (e.g., <5 cm), such shorter expandable members, in the absence of additional longer members, may be less useful, as they may be difficult and expensive to manufacture, having a great number of sections to bond, and may also add multiple stiff coil sections where the proximal end of each braid section is attached to the coil. Such stiff coil sections may increase the risk of brain aneurysm rupture when deployed into the aneurysm.

In contrast, the implants described herein are "soft" to prevent damage/rupture of the aneurysm body. For example, the use a fine wire tubular braided region (<0.0008" NiTi, or more preferably between about 0.0005" to 0.0075") over a soft Pt coil (inner member) may provide an embolic device that is small soft enough to be safely deployed into a fragile aneurysm.

Furthermore, the implants described herein typically include a pore size that is sufficiently small to occlude blood. For example, using a specific number of braids (e.g., between 24-48 ends) and heat setting the fully expanded braid angle (e.g., the angle of the braided region when unconstrained outside the catheter) so that the expanded braid angle is between about 35-90 degrees (preferably <60 degrees, and even more preferably around ~50 degrees) on a mandrel that is between about 0.75 mm to 3.0 mm in diameter, with a preferable diameter range 1.0 to 2.0 mm may help ensure that the created pore size of the braid material is small enough (e.g., less than about 0.1 mm$^2$, and preferable <0.06 mm$^2$) to arrest blood flow into a blood vessel or aneurysm filled with such an implant.

As mentioned above, the braided tubular regions can be pre-set (shape set, for example by heat setting) to have a round or non-round cross-sectional shape, e.g., flat oval or of other geometric shapes, to give the braid a specific cross-sectional shape. To have the braid expand to a maximum width, it may be desirable to heat set the braid to an oval of flat shape, rather than round. A tubular braided region may also be heat set into a variety of three-dimensional shapes, as discussed above (e.g., a curve shape along its length, rather than being straight).

Any of the implants described herein are typically retrievable into catheter (delivery device). For example, an implant (which may be referred to as a braid/coil assembly) may be retrievable when pulled back (proximally) into catheter. This may be achieved by having the proximal end of each braid attached to the coil and the distal end of each braid segment being free to expand, as mentioned above. The coil assembly may be resistant to damage/permanent set during retrieval. This may be achieved with soft platinum coils, for example. Any of these implants maybe configured to be detachable into aneurysm/vessel at the users control.

Thus, any of the implants (embolic devices), and particularly the devices including a free-floating end described herein may include an inner member (e.g., coil) attached to a detachable pusher wire element intended to be delivered and retrieved through a catheter delivery system before being detached, where one or more expandable, soft braided tubular elements are located around the coil and formed to expand to a diameter of at least 1.5 times larger than the coil's diameter, when unconstrained (e.g., outside of catheter). The proximal end of each braided tubular element may be fixed to the coil, and the distal end of each tubular element may be free floating. The tubular braided element (structure) may be pushable inside the catheter, and the braid may maintain its stability after multiple deployments. For braided members that are longer than about 5 cm or more (e.g., between about 5 cm and about 45 cm, preferably between about 5 cm and 30 cm), the braid angle when constrained inside the catheter typically ranges from less than 35 degrees when the number of strands (ends) is between about 12 and about 48 (e.g., between about 12 and about 36, between about 24 and 36, between about 12 and 40, etc.). At least one of the individual braid ends (strands) has a diameter between about 0.0005" to 0.002".

Figure 6A:
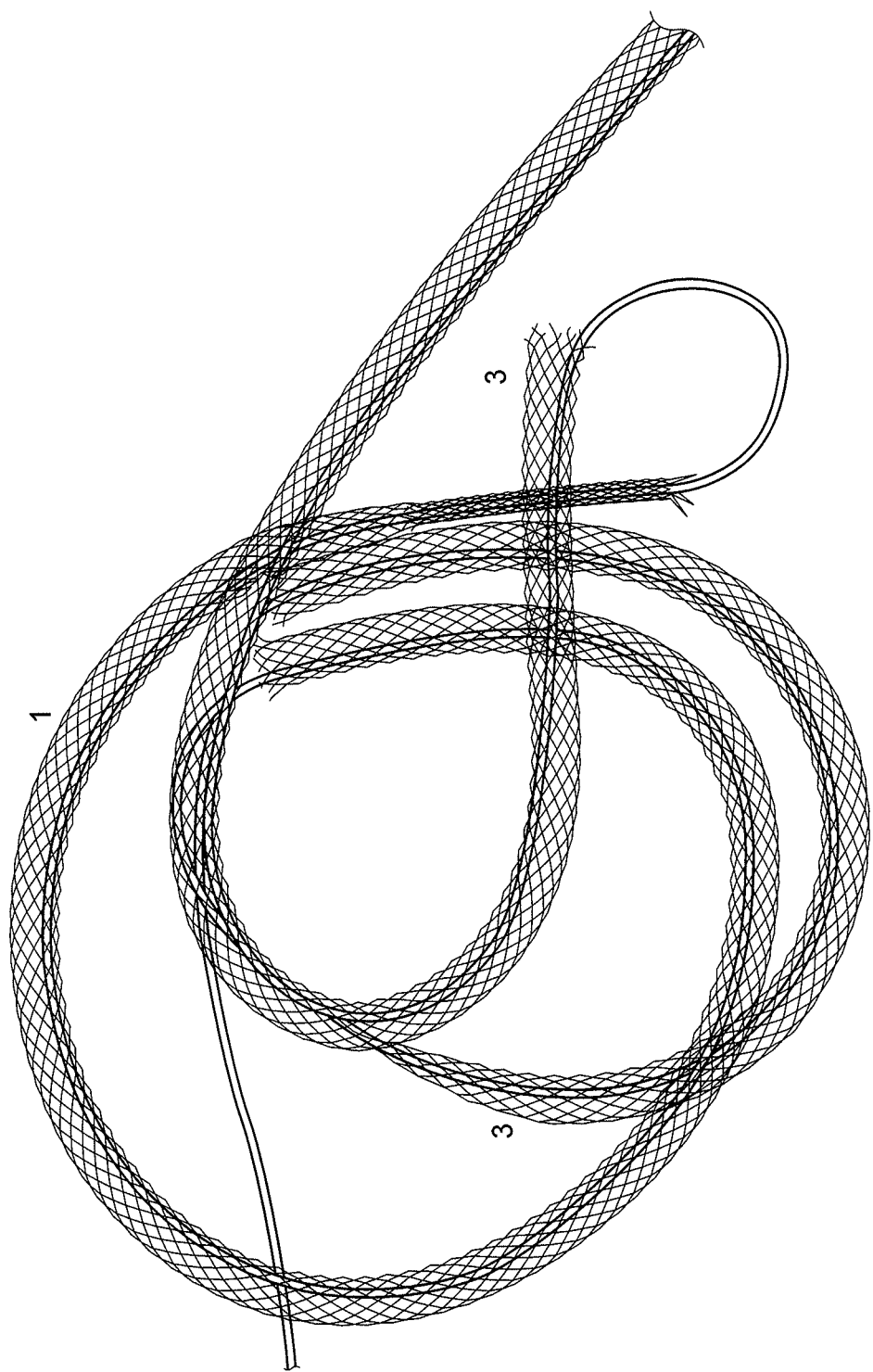
FIG. 6A is another example of a vaso-occlusive device (implant) having a pushable inner member and a plurality of soft, elongate, braided members that are attached to the inner member at only a proximal location.

FIG. 6A illustrates another variation of a preferred embodiment of a vaso-occlusion implant for occluding an aneurysm that includes an inner member (coil) and an outer braided member having a length greater than 5 cm which is attached to the inner member only at the proximal end of the braided member. For example, in FIG. 6A, a portion of such an implant is shown, including three braided members formed of 24 strands of 0.0075 inch Nitinol. The expanded braid angle of the braided members has a braid angle of approximately 51 degrees. In FIG. 6A, three discrete sections of braided members are shown attached (e.g., by an epoxy) at their proximal end to the inner member. The inner member is a 0.020 inch OD platinum coil. The three lengths of braided members include a first braided member that is 12 cm long, a second length of braided member that is 12 cm long and a third length of braided member that is 3 cm long, for a total of 28 cm of braided length attached to a 45 cm long inner, coil, member. The entire length may be loaded into a delivery catheter having an inner diameter of approximately 0.025 inches.

Figures 6B, 6C:
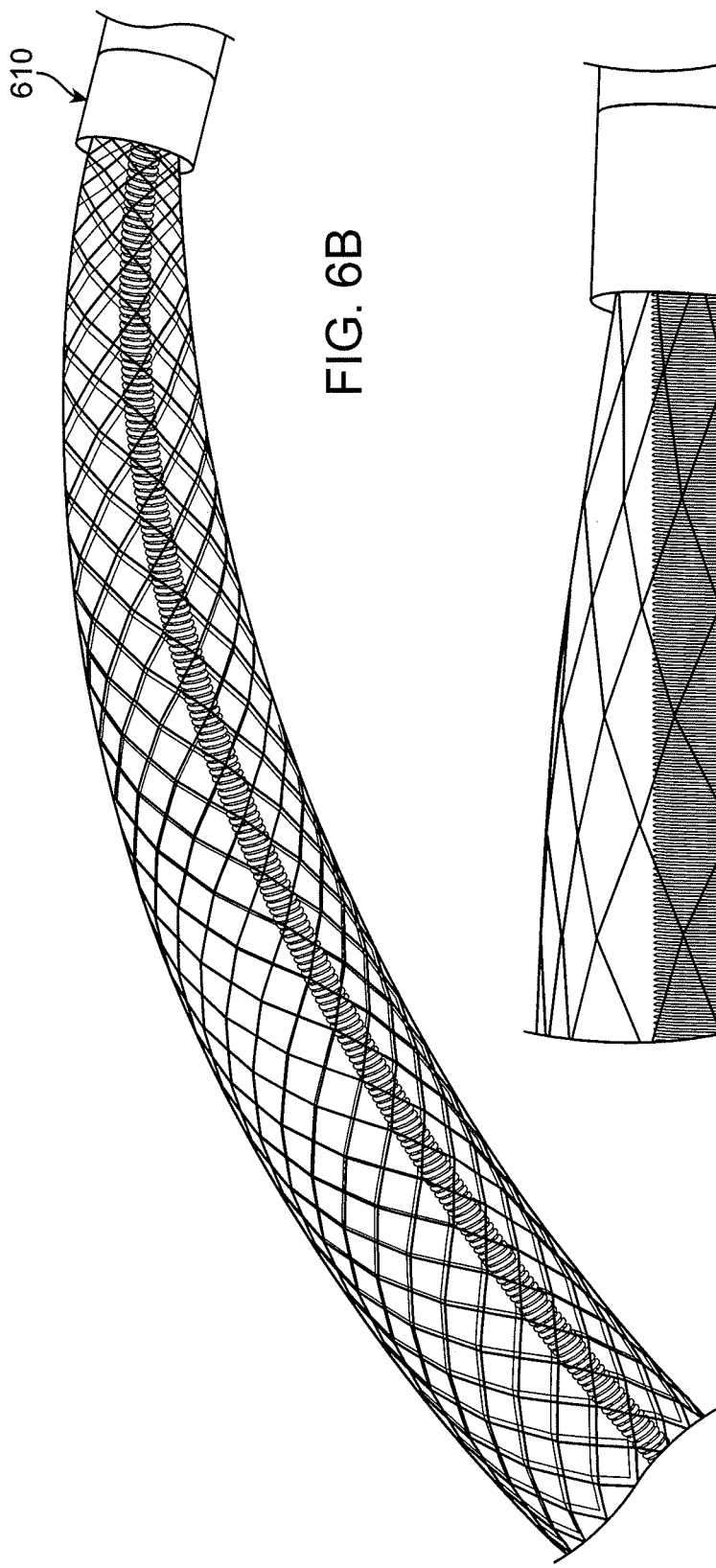
FIGS. 6B and 6C show enlarged views of portions of the implant of FIG. 6A.

FIGS. 6B and 6D illustrate enlarged views of the implant of FIG. 6A as it is extruded (pushed) distally out of a catheter 610, to expand. The constrained braid angle in the catheter is approximately 33 degrees, and the braided region expands to a diameter of greater than 1.5 times the diameter of the inner member (in this example, the outer braided region expands to a diameter of about 5-6 times the diameter of the inner member. FIG. 6C shows a slightly enlarged view of the device exiting the catheter 610.

Figure 7A:
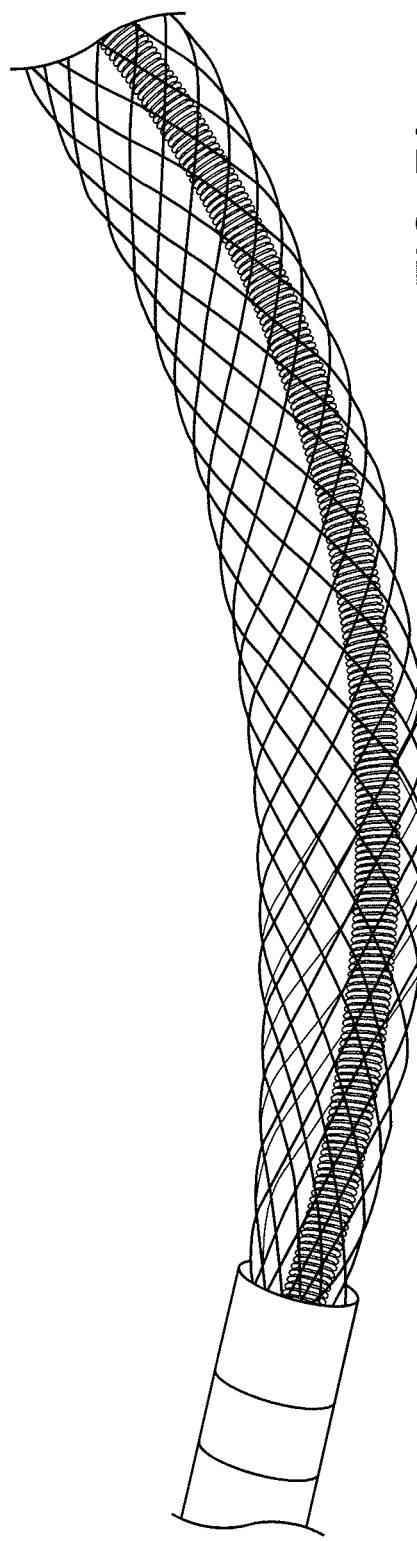
FIGS. 7A and 7B show another example of a vaso-occlusive device (implant).
Figure 7B:
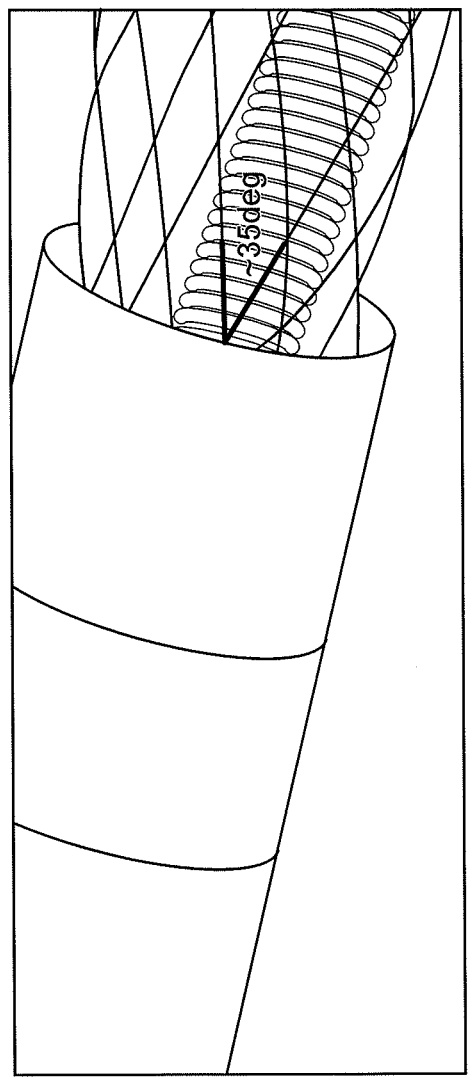

FIGS. 7A and 7B show another example of an implant having a braided outer member that is only attached to the inner member at the proximal end and is free-floating at the distal end. In FIG. 7A, the implant includes an outer braided member that is formed of 24 strands with an expanded diameter of approximately 1 mm and a 53 degree braid angle; when constrained in the catheter, the implant is pushable (even for greater than 5 cm of length of the expandable braided member) and has a collapsed/constrained braid angle of approximately 35 degrees. FIG. 7B shows a slightly enlarged view of the implant as it is pushed distally from a catheter.

Figure 8A:
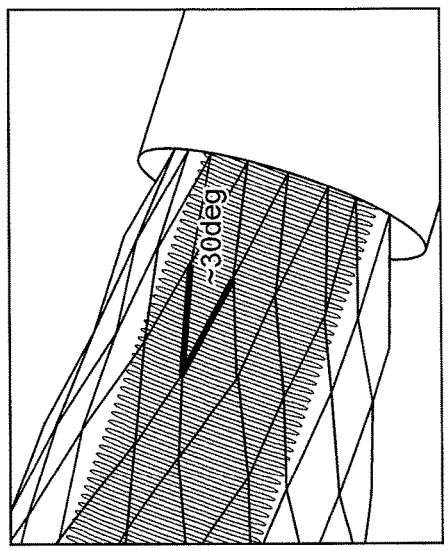
FIGS. 8A-8E illustrate various examples of portions of vaso-occlusive devices with braid angles labeled when in a delivery catheter.
Figure 8B:
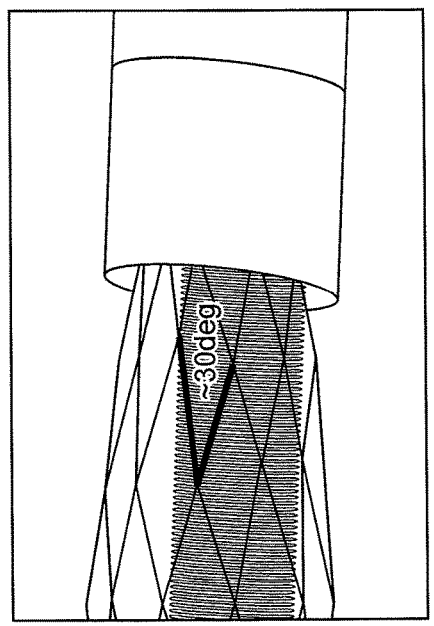

As mentioned above, the ability of an implant having a central core (e.g., coil) with an attached expandable outer braided member that is coupled to the central core only at the proximal end to be pushable out of and within a delivery catheter may depend upon a number of features. The inventors have herein determined ranges of values for these parameters that may be used to determine when an implant is pushable (and therefore useful) for delivery from a catheter. In some variations, the maximum length of a braided region on an implant that allows pushing from a delivery catheter varies depending on one or more of: braid angle within the catheter (constrained braid angle), expanded outer diameter (OD), expanded braid angle, and number of strands forming the braided region (e.g., number of "ends"). FIGS. 8A-8E illustrate a variety of different implants having the same characteristics for an inner member with different examples of braided tubular members, and indicates the maximum length of each braided member that may be considered "pushable" for a particular delivery catheter. For example, in FIG. 8A, the braided outer member is a 24 strand braided member having a 1.5 mm expanded diameter and a braid angle of about 51 degrees, with a collapsed/constrained braid angle of approximately 30 degrees; for this example greater than 15 cm of length could be easily pushed through the delivery catheter. In FIG. 8B, the braided member has an outer diameter of 2 mm and is formed of a 36 strand (36 end) braid with an expanded braid angle of approximately 81 degrees and a collapsed/constrained braid angle of approximately 30 degrees within the delivery catheter. For the example shown in FIG. 8B, only an implant having approximately 8 cm of length was pushable distally out of the delivery cannula.

Figure 8C:
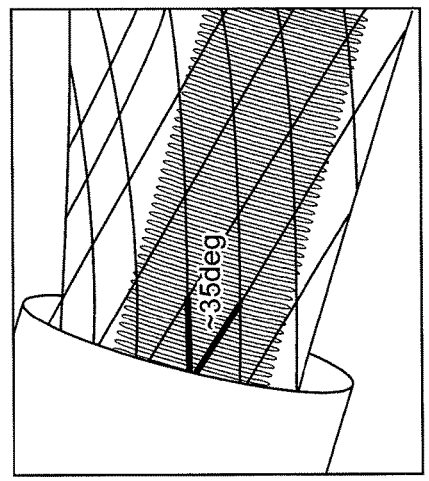
Figure 8D:
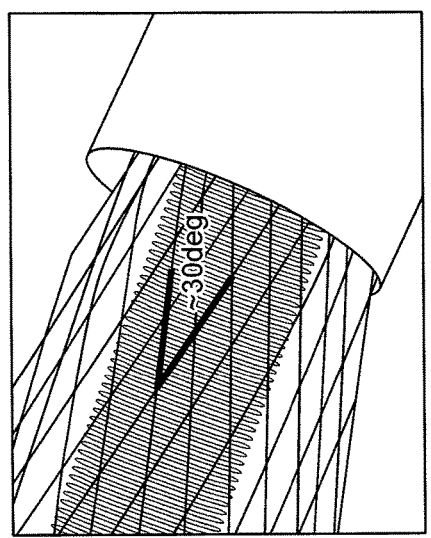
Figure 8E:
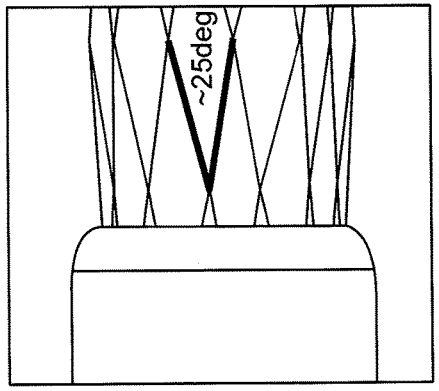

In FIG. 8C, the braided member has an outer diameter of 2 mm and is formed of a 24 strand (24 end) braid with an expanded braid angle of approximately 80 degrees and a collapsed/constrained braid angle of approximately 25 degrees within the delivery catheter; an implant having a braided member of approximately 20 cm was pushable distally out of the delivery cannula for this example. In FIG. 8D an implant having a maximum length for the braided outer member of approximately 10 cm was pushable where the braided outer member had a 2 mm outer diameter, 48 ends, an expanded braid angle of about 85 degrees and a collapsed/constrained braid angle within the cannula of about 30 degrees. Similarly, as shown in FIG. 8E, an implant having a braided outer member with a maximum length of approximately 8 cm was pushable when the braided outer member had an expanded diameter of 1 mm, had 24 strands (24 ends), an expanded braid angle of 53 degrees and a collapsed/constrained braid angle within the catheter of approximately 35 degrees.

Figure 9B:
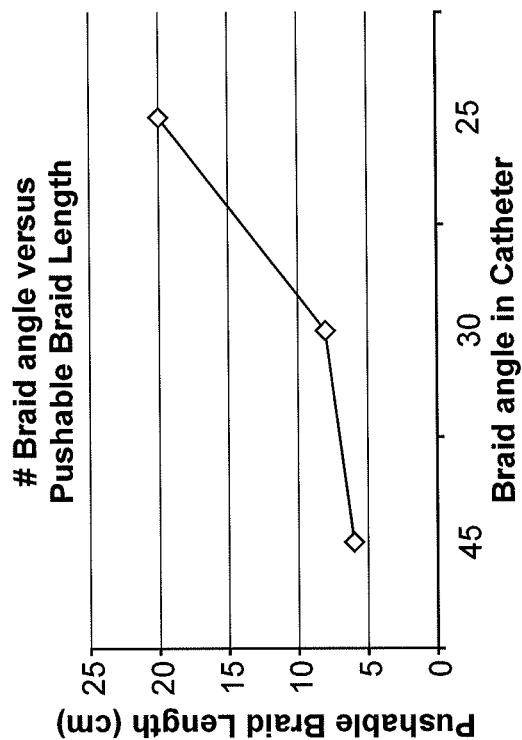
FIGS. 9A and 9B are graphs illustrating the relationship between pushable braid length and the number of strands (braid ends) and braid angle (compressed), respectively.
Figure 9A:
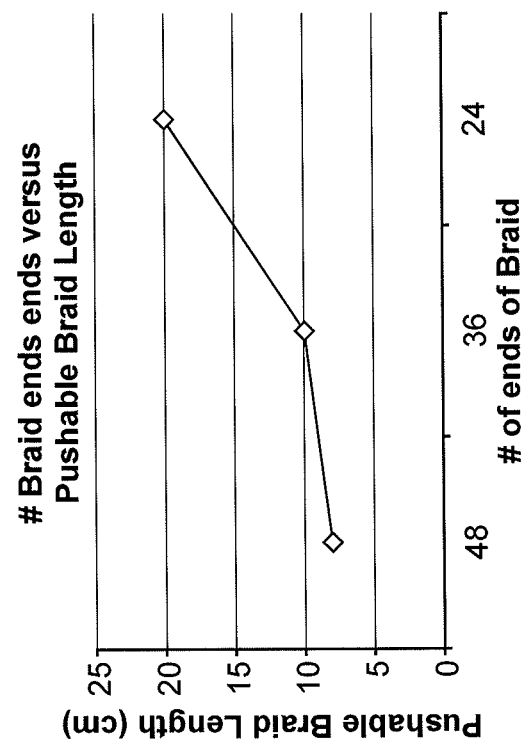

The graphs shown in FIGS. 9A and 9B illustrate exemplary relationships for the number of strands forming the braid ("number of braid ends") versus the pushable length of the braid (FIG. 9A) and the braid angle in the catheter (constrained/collapsed braid angle) versus the pushable braid length. As can be seen, in general, the fewer the number of braid ends (strands) the longer the pushable length, as well as the lower the braid angle, the greater the pushable length. A multivariate analysis in which braid angle, strand number, and relative outer diameter were accounted, a braided outer member that is attached to an inner member only at the proximal end may have one or more braided members of length greater than 5 cm (e.g., between 5 cm and 30 cm, and more particularly between 10 cm and 30 cm) when the number of braid ends (strands) is between about 24 and 36 and when the constrained braid angle is about 35 degrees or less. While shorter lengths of braided members may be pushable, outside of this range, the implant is more likely to bind up within a delivery catheter, preventing reliable delivery.

FIG. 10 is a table illustrating some of the parameters exampled for pushable braided regions. The results generally fit the predicted results described above and provide a range of potential values for some of the characteristics discussed. Braided regions having the smallest braid angles (e.g., 25 degrees) allows pushing of the longest lengths of braided regions, while braided regions having more than 36 ends and 75-80 degree (unconstrained) braid angles allowed only relatively small lengths of braided regions to be pushed.

FIGS. 11A-11B, 12 and 13 illustrate examples of devices having outer, braided members with different characteristic properties and therefore different maximum lengths that may be pushed out of a typical 0.025" inner diameter (ID) catheter ("Penumbra"). In FIGS. 11A and 11B, the braid is pushable for lengths of greater than 20 cm; the braided region has a collapsed/constrained brain angle within the catheter of approximately 25 degrees, and the braid is formed from 24 strands of 0.0008" Nitinol. The unconstrained (expanded) braid angle is approximately 80 degrees and the outer diameter is 2 mm.

Figure 12:
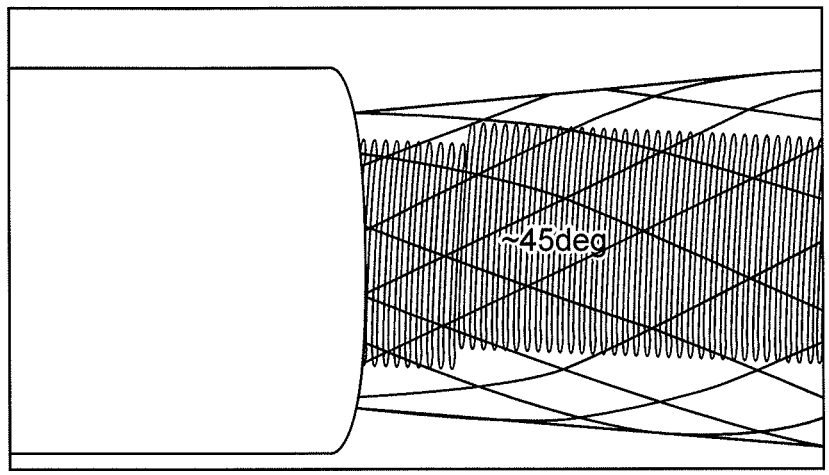
FIG. 12 illustrates an example of a vaso-occlusive device with a soft, elongate, braided outer member that is less pushable than the example shown in FIGS. 11A and 11B.
Figure 13:
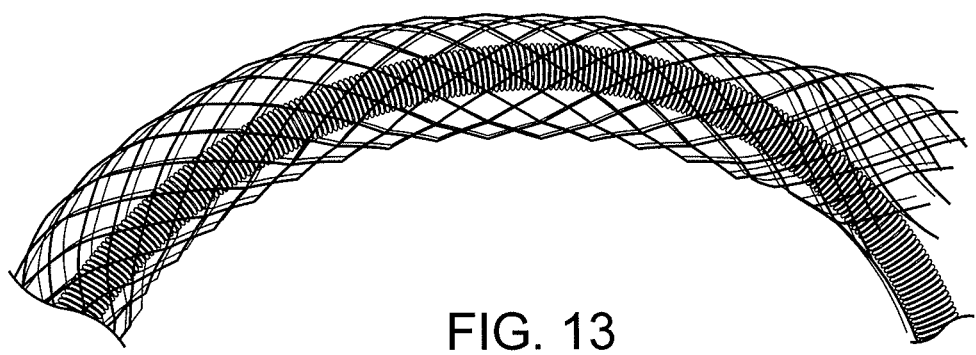
FIG. 13 shows an example of a vaso-occlusive device with a soft, elongate, braided outer member that is less pushable than the example shown in FIGS. 11A and 11B.

In contrast, the braided region shown in FIG. 12 also has a braid that is formed from 24 strands of 0.0008" Nitinol, but has a constrained angle within the delivery catheter of approximately 45 degrees. The unconstrained (expanded) outer diameter in FIG. 12 is approximately 1 mm and the braid angle is 80 degrees. In this example, only about 5 cm of braided region could be pushed. Similarly in FIG. 13, the resulting implant with a braided region having an OD of 2 mm and an expanded braid angle of 80 degrees but a constrained braid angle of >35 degrees with 24 strands could not be pushed out of the catheter at any length tested (2 cm or greater).

FIGS. 14A-14C illustrate the use of one example of a vaso-occlusive apparatus (including a vaso-occlusive implant). In FIGS. 14A-14C, the implant is inserted into a simulated (silicone) aneurysm. In FIG. 14A, the first seven cm of implant having an inner pushable member to which an outer expandable braided region is attached at only the proximal end, and is free-floating at the distal end. In FIG. 14B the final 30 cm of the implant have been inserted, resulting in a high density coverage of the aneurysm neck region, as shown in greater detail in FIG. 14C. In general, a method of inserting an implant having an expandable braided region as shown above may be used to deliver between 30-50 cm (or more) of implant even through a highly tortious path. The implant may be retrieved (e.g., by withdrawing proximally) and is radiopaque and stretch resistant.

Part II: Vaso-Occlusive Devices with Friction Elements

A. Friction Element on Inner Member

Any of the vaso-occlusive devices described herein may have one more (e.g., a plurality) of friction elements that act to increase the friction between the pushable member (e.g., coil) and an expandable, soft, braided member when the braided member is in a collapsed configuration, e.g., within a catheter lumen of the delivery device. Further, the friction element may be adapted so that it does not contact or increase friction with the inner surface of the catheter lumen.

In general the friction element is positioned between the braided member and the pushable member, in a region that is proximal to the distal end and distal to the proximal end of the expandable braided member. For example, a friction element may be positioned on or formed by a region of the pushable member (e.g., inner coil). Such friction elements may be protrusions formed on/off the pushable member, including for pushable members formed by coils, regions of the coil having a larger diameter. In some cases the friction elements are instead attached to the expandable braided member. In some cases the friction elements are free-floating between the pushable member and the expandable braided member. Combinations of such friction elements may be used.

For example, FIG. 15A shows one variation of an implant having an elongate pushable member 1505 formed as a coil and an outer expandable braided member 1503 that can be collapsed around the inner coil member 1505 when held in a delivery device (e.g., catheter). In FIG. 15A a single friction element 1501 is shown attached to a portion of the pushable member 1505. The friction member 1501 in this example is a cylindrical body that is tapered at the ends, and attached to an outer region of the inner coil. The body of the friction element may be formed of a material having a relatively high friction when interacting with the expandable braided member, such as a polymeric (e.g., rubber, silicone, etc.) material. In FIG. 15 the friction element extends slightly (protrudes) from the surface of the pushable member; the friction element is formed as an annular body around the entire outer surface of a short stretch (e.g., less than 0.2 mm, 0.5 mm, 0.7 mm, 1 mm, 1.2 mm, 1.5 mm, 1.7 mm, 2 mm, etc.) of the inner member. Shorter regions may be preferred, as they may interfere less with the flexibility/bending of the inner member. In FIG. 15A, the outer diameter of the friction element is slightly larger than the outer diameter of the inner member (coil 1505). In some variations the outer diameter may be non-uniform or it may be flush with the outer diameter of the inner member. In some variations the outer diameter is approximately 0.05 mm (or 0.1 mm, 0.2 mm, 0.3 mm, etc.) greater than the diameter of the pushable member. A friction element may be compressible and/or expandable. Further, although the friction element shown in FIG. 15A is solid, in some variations the friction element is a braided or woven material that is biased to expand radially outwards.

A friction element, including the friction element 1501 shown in FIG. 15, may be referred to as a bump.

FIGS. 15B and 15C show less enlarged views of the apparatus of FIG. 15A. In FIG. 15B a delivery catheter 1507 holding a portion of the implant 1500 (embolic device) is included. In FIG. 15C the implant 1500 is shown to include a plurality of different friction elements ("bumps" positioned at 3 cm intervals over the length of the inner core member 1505 in regions underneath a middle portion of an expandable braided member.

In FIGS. 15A-15C, the core (inner pushable member 1505) can have multiple friction elements as shown. These bumps 1501 can be radially larger than the core, and may be slightly less or the outer diameter of the bump can match the inner diameter of the embolic device and/or braided member when in a radially contracted configuration (e.g., loaded in the catheter). For example, a friction element outer diameter can be about 0.0215 inches and the catheter inner diameter can be about 0.0220 in. The pushable member (core) can have an outer diameter from about 0.002 in. to about 0.010 in. smaller than the outer diameter of the bump 86. The bump length can be from about 0.1 mm to about 10 mm. Bumps can be spaced apart, for example, by a bump spacing of about 3 cm longitudinally from each other on the core. Bumps can be soft, tacky, or the like, including being formed of expandable foam or rubber. Bumps can have knurls. Bumps can be heat sensitive. Bumps can expand into the cells in the inner member (e.g., coil) and/or braided member ("deforming layer").

Figure 16A:
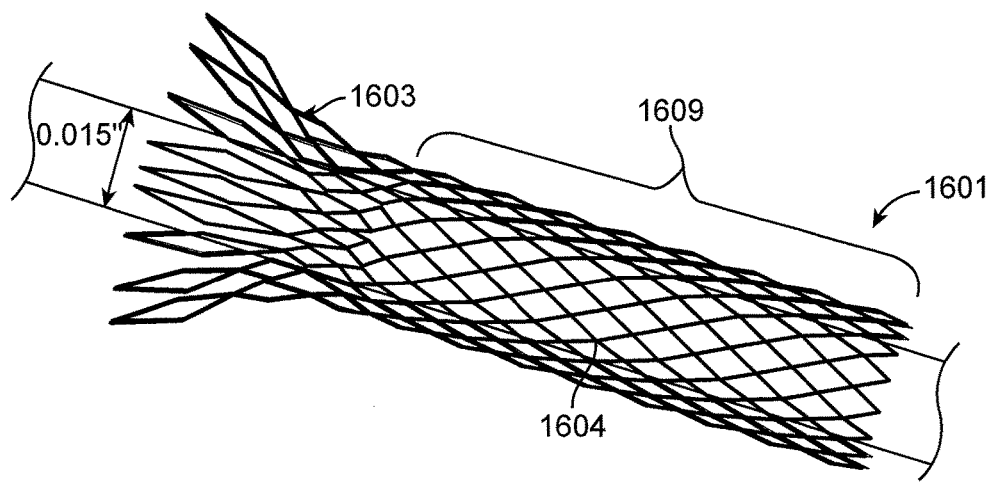
FIGS. 16A and 16B show another example of a friction element (FIG. 16A) and an implant including the friction element (FIG. 16B).
Figure 16B:
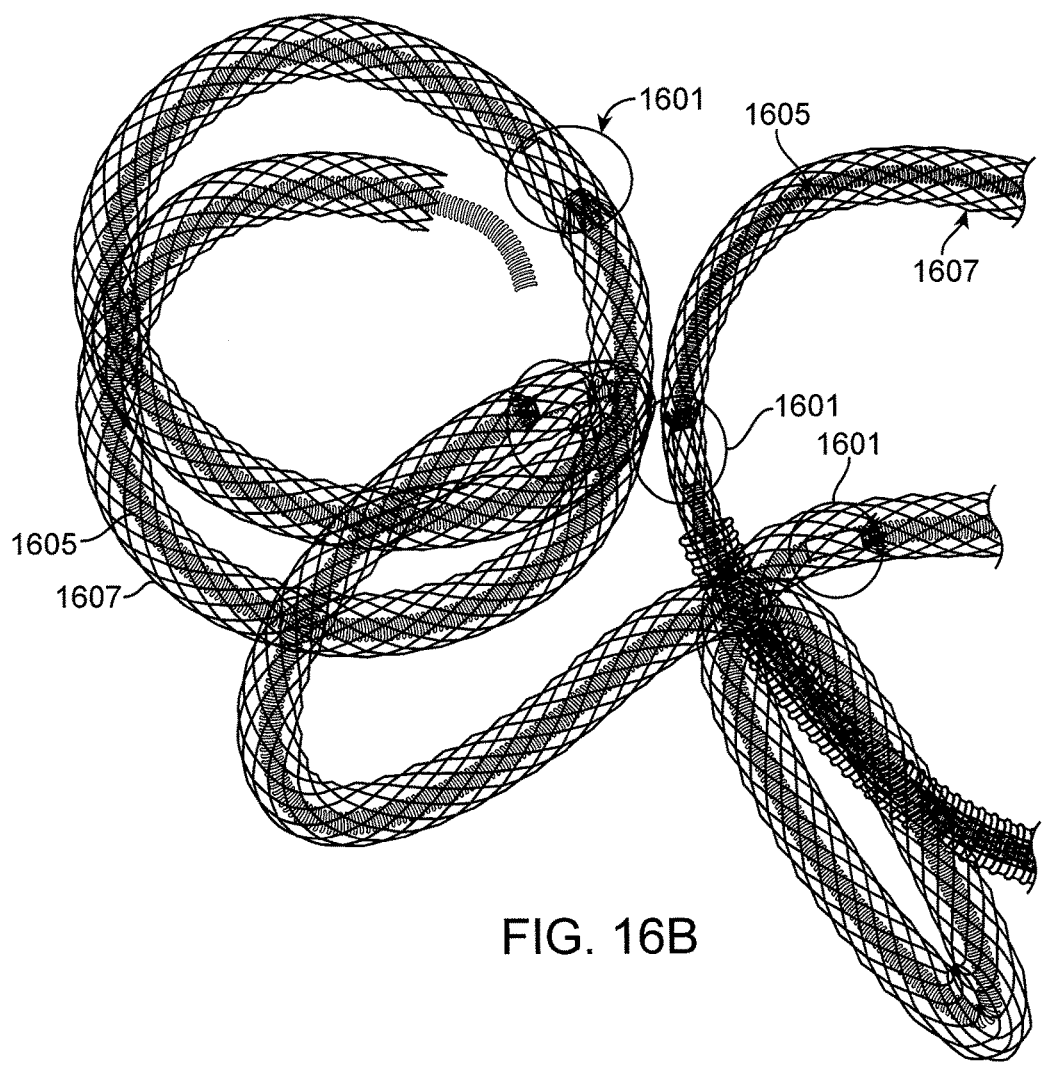

FIGS. 16A-16D show another variation of a friction element 1601 attached to a pushable member. In FIG. 16A, the friction element is configured as an expandable friction element having free ends 1603 ("prongs") that flare away from attachment site to the pushable member. This variation may be referred to as a 'flare'. A region of the friction element is attached to the pushable member and one or both ends of the element are configured to expand outward from a collapsed configuration. In FIG. 16A, the friction element (flare) can be made from a braid. For example, the flare can be made from braided wire. The wires of the flare can be made from any material disclosed herein or combinations thereof, for example Nitinol. In one example, the flare has about 24 wires. The wires forming the flare can be from about 0.0005 in. to about 0.0011 inches, for example about 0.0008 in. in diameter. The ends of the wires forming extending from the body of the friction element ("flare prongs"), can interdigitate with the openings (e.g., pores/cells) of the expandable braid member. A region (e.g., the proximal end) 1609 of each friction element having a flaring configuration can be fixedly attached to the pushable member (core wire or coil). FIG. 16B illustrates that an implant having a pushable member (coil 1605), outer braided member 1607 and multiple friction elements configured as flares 1601 that are spaced along the pushable member 1605. For example, along a 30 cm length of pushable member (core), the friction elements (flares 1601) can be longitudinally spaced apart with the first prongs of each flare at 12 cm, 15 cm, 18 cm, 21 cm, 24 cm, and 27 cm from the proximal end of the pushable member 1605. The friction elements can also be placed, for example, with the first prongs of each flare at 3 cm, 6 cm, and 9 cm from the proximal end of the pushable element.

FIG. 16A shows one example of formation of a braided friction element configured as a flare braid. The flare braid can be braided over a first manufacturing mandrel, and then inverted (i.e., turned inside out) over a second manufacturing mandrel. A cohesion layer can then be formed by applying melted polymer onto the attachment region (e.g., proximal end) of the friction element. The prongs or fingers of the friction element can be uncoated with the polymer, or coated to increase friction between the friction element and the braided member.

As mentioned above, a friction element can be made from multiple wires (e.g., 24 wires, etc.). For example, the wires can be about 0.0008 in. in diameter. A first manufacturing mandrel can be about 2 mm in diameter. The second manufacturing mandrel 66 can have a second manufacturing mandrel diameter 68 of about 0.015 inches.

Figure 16C:
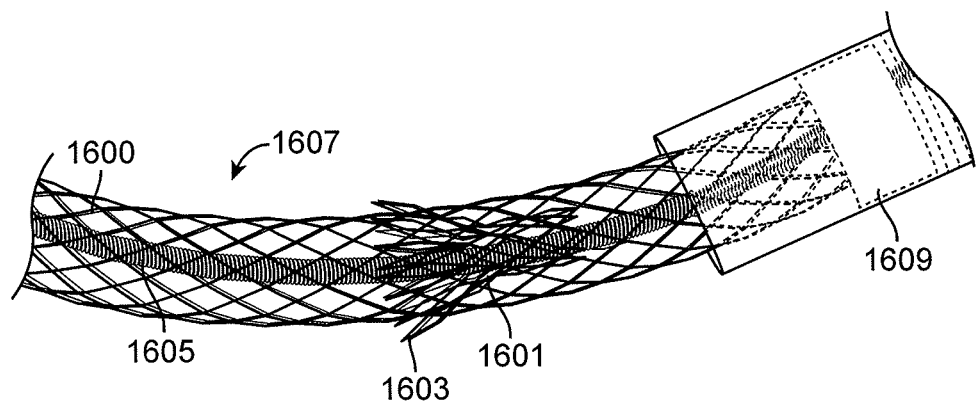
FIG. 16C shows the implant of FIG. 16B within and exiting a delivery catheter.

FIG. 16C illustrates operation of an apparatus including a friction element configured as an expanding or flaring element that is attached to an inner coil forming a pushable member. In FIG. 16C, the device 1600 (embolic or vaso-occlusive device) is shown extending from within a catheter 1609. The implant includes an inner coil 1605 forming a core (pushable member) over which an expandable braided member 1607 is positioned. When held within the catheter, the braided material is collapsed and the friction element 1601 connects the braided element 1607 with the pushable member (core 1605) so that as the core is pushed distally (or pulled proximally) the braided element and the pushable member move together. In FIG. 16C, the prongs of the flaring friction element or friction member extend outwards top pass within and engage the braided member. Once allowed to expand after release from the catheter, the flaring friction element does not interfere with expansion of the braided element and may remain attached, or it may separate from the friction element.

Figure 16D:
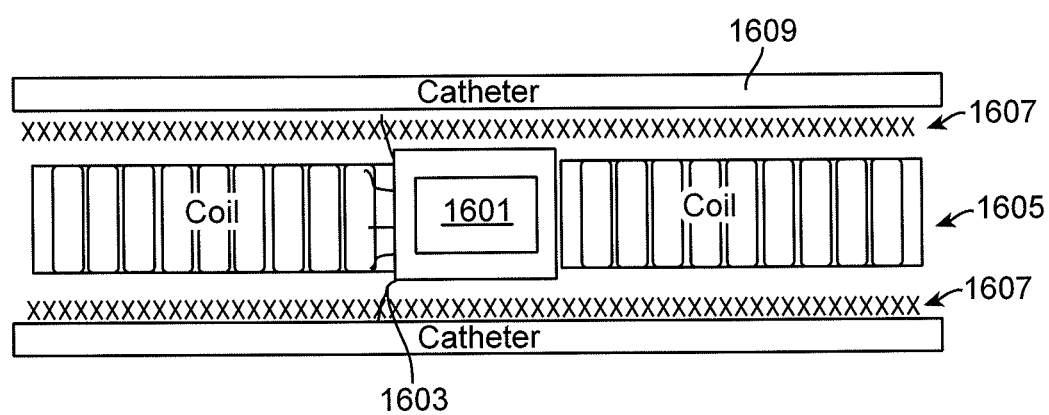
FIG. 16D is a schematic illustration of an implant including a friction element such as the one shown in FIG. 16A.

FIG. 16D is a schematic view of one variation of a system including an outer catheter 1609, that may house an implant with an outer, soft and expandable braided member 1607 and an inner pushable member configured as a coil 1605 to which one or more friction elements 1601 having a plurality of extending prongs or arms 1603 extend to engage the braided member 1607 when the braided member is collapsed over the inner member 1605 within the catheter.

In the example shown in FIG. 16C, the prongs 1603 can extend through cells or pores in the braided member 1607 of the embolic implant device. The prongs 1603 can radially restrain the braided wires of the braided member, for example, preventing the braided member from completely expanding when outside of the catheter 28. The inner pushable member 1605 can be retracted to withdraw the prongs 1603 of the expandable member from the embolic device, allowing the braided member of the embolic device 1607 to radially expand completely.

As mentioned, FIG. 16D illustrates that the friction element prongs can pass through cells of an outer braided portion of an embolic device, and may contact the inner wall of the catheter when the friction device having a flare is in the catheter. When the flaring arms of the friction device are deployed from the catheter 1609, prongs 1603 can release and detach from the braided member forming part of the device. The prongs 1603 can extend orthogonally (i.e., perpendicular) to the longitudinal axis of the core (pushable member 1605) of the device over a short region while still engaging the braided member 1607 of the implant. For example, the pushable member (e.g., coil) can have an outer diameter of about 0.015 in. The catheter can have an inner diameter of about 0.021 in. The prongs 1603 can extend orthogonally about 0.003 in. The inner coil can have a single prong or arm of a friction element (e.g., flare 1601) per unit length (e.g., a single prong extending from each flare) or multiple prongs per unit length, as shown in FIGS. 16A-16D. The prongs can extend at a prong angle (in an unconstrained state) that is between about 70° to about 110° relative to a longitudinal axis of the inner member 1605. A flare braid may be made on a first manufacturing mandrel, or formed directly on an inner member. For example, a portion of the length of the braid can be coated with a polymer to form a cohesion layer securing the friction member to the pushable inner member (e.g., coil).

Another variation of a friction element is shown in FIGS. 17A-17C, in which the friction element 1703 is also a braided structure forming a 'bump' that is coupled to the inner pushable (coil) member. In this example, the 'bump' region attaches at both ends to the inner member (coil) 1705. One advantage of this configuration is that the expandable bump may extend relatively far along the length of the pushable member and since only the ends are attached to the pushable member, even a long bump region will not adversely affect flexibility of the implant.

As shown in FIG. 17A, the friction element (bump 1703) can have a braided, woven or knitted configuration. In FIG. 17A, the friction element (bump) can have a wireframe. When the bump is attached to a pushable member 1705 (which may also be referred to as a coil, core, leader, etc.), at the proximal and/or distal end of the braided bump. When just one end (e.g., the proximal end) of the friction element is fixed, the braid of the friction element can radially expand further when the opposite end (e.g., the distal end) is forced to slide (e.g., proximally), causing the bump to exert more radial force onto the inside of the braided member.

FIG. 17B shows a pusher member (inner coil member 1705) with an attached friction element 1703 that is a flexible basket (braided structure) before it is inserted into an elongate, soft expandable braided member 1701, as shown in FIG. 17C, and pulled proximally into a catheter 1706 to pre-load it. In FIGS. 17B and 17C, the friction element (bump 1703) has a distal bump collar 1722 and/or a proximal bump collar 1721. The bump collars can be fixed or integral with the remainder of the friction element. For example, the friction element 1703 can have a braid of wires or fibers, and the collars can be coated lengths of the braid at the longitudinally terminal ends of the braid.

The proximal and/or distal collars can be longitudinally and/or rotatably fixed, anchored or locked, and/or longitudinally slidably attached to the inner member (pushable coil element 1705). For example, the proximal bump collar can be fixed to the pushable member 1705. The distal bump collar can be slidably attached to the pushable member 1705. When the friction element is in the catheter, as the pushable member 1705 is translated distally, the friction element can press into the expandable braided member 1707, pressing the braided member 1707 into the radially inner surface of the catheter wall. The drag from the catheter wall can be transferred through the braided member 1707 (which can be in compression between the friction element and the catheter) and to the most radially-expanded length of the friction element. The friction element at that most radially-expanded length can be pushed proximally by the drag force. If the proximal bump collar is fixed to the pushable member and the distal bump collar is slidably attached to the pushable member, the friction element can longitudinally shorten and radially expand, for example, exerting more radial force against the braided member 1707 (e.g., compressing the braided member 1707 against the catheter), and transferring more of the longitudinally translating force from the pushable member to the braided member 1707.

As mentioned, FIG. 17C illustrates that the braided member 1707 can be positioned over and pressed against the friction member as the friction member exits the catheter (or is drawn into the catheter if withdrawing the implant or loading it). The braided member 1707 of the implant can radially expand upon release from the catheter. As the friction element translates distally away the distal port of the catheter, the braided member 1707 can radially separate from the friction element.

Figure 18:
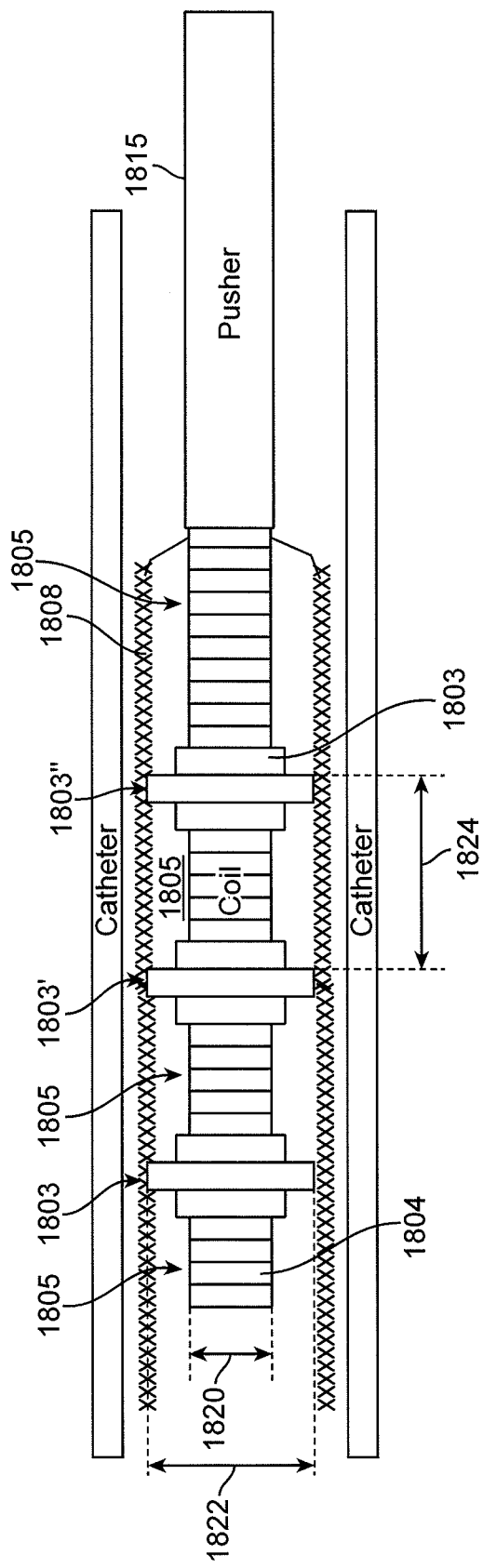
FIG. 18 is a schematic of another variation of a vaso-occlusive implant including a plurality of friction elements formed integrally into the pushable member.

Another variation of a friction element is shown in FIG. 18. In this example, the friction element is an integrated part of the pushable member, which is shown as a coil 1805. Longitudinally separated regions of the pushable member have an expanded diameter ("peak diameter") that is greater than the primary diameter of the pushable member (coil 1804). The expanded diameter regions in this example are formed by coils having a larger diameter. When constrained within a catheter, as shown in FIG. 18, the implant includes the pushable member (coil 1804) inside of an elongate, expandable and soft braided member 1807. The larger diameter friction element regions 1803, 1803', 1803" of the pushable member increase the friction between the pushable member and the braided member so that driving (e.g., using a pusher 1815) the pushable member distally (or withdrawing it proximally) also moves the braided member within the catheter 1811, as the catheter wall has a lower friction relative to the braided member.

In FIG. 18, the pushable member is formed of a coil having a winding with coil primary sections 1805, 1805', 1805" and peaks 1803, 1803', 1803", such as first, second and third peaks, as shown. The primary section 1805 can have lengths on either or both ends of the most proximal and distal peaks and between adjacent peaks. The primary section can have a primary diameter 1820. Lengths of the primary section 1805 separated by a peak 1803 can have equal or different primary diameters 1820. The primary diameter 1820 can be constant along the length of a contiguous (i.e., not separated by a peak) primary section. The primary diameter 1820 can be constant along the length of all primary sections for the pushable member 1804 or can vary between the primary sections (e.g., the primary diameter 1820 can be larger or smaller for one primary section compared to an adjacent primary section). Each peak can be the radially outermost winding for a wave formed in the coil. As mentioned, the peaks can press the braided member into the wall of the catheter. The peak can frictionally drag the braided member longitudinally along the catheter lumen when the pusher 1815 is pushed or pulled, resulting in the braided member being longitudinally translated with respect to the catheter. The braided member can be taut (i.e., in tension) between adjacent peaks.

The primary diameter 1820 can be from about 0.005 inches to about 0.050 inches, for example about 0.015 inches. The peak diameter 1822 can be from about 0.010 inches to about 0.055 inches, for example about 0.020 inches. For example, the peak diameter 1822 can be from about 5% to about 50%, or for example about 10% larger than the primary diameter 1820. The peaks can be separated by wave gaps 1824. The wave gaps 1824 can be from about 0.001 to about 0.010 inches, for example about 0.002 inches. The wave gaps 1824 can be equal to the dimensions disclosed for spacing between the friction element regions and vice versa.

The coil forming the pushable member can be open pitch or closed pitch. The coil can be a single winding along the length of the coil (e.g., wound and shaped, such as with heat, on a mandrel with the desired shape of the primary sections and waves). The coil can be made from bonding or welding a winding of the coil primary section to a coil formed as a wave, and attaching additional primary sections and waves as needed for the desired shape. The distal terminal end of the braided member can be attached to the coil (not shown for illustrative purposes) or unattached.

Also described herein are friction elements that are attached to the braided member. In general, the fiction elements may be attached at a variety of different locations, and arranged circumferentially around the braided element, and/or staggered along the length of the braided member. In general, a friction element may be attached to the braided member in any appropriate manner, including bonding, gluing, over-molding onto the braided member, sewn or tied onto the braided member, melted or formed onto the braided member, or the like. In some variations, small tubular friction elements may be threaded over a strand of the braided element prior to braiding. In some variations the friction elements on the braided member are coupled to the braided member so that the majority of the friction-enhancing surface faces inward (e.g., towards an inner pushing member) and not outward (towards the catheter wall when loaded into a catheter).

Figure 19A:
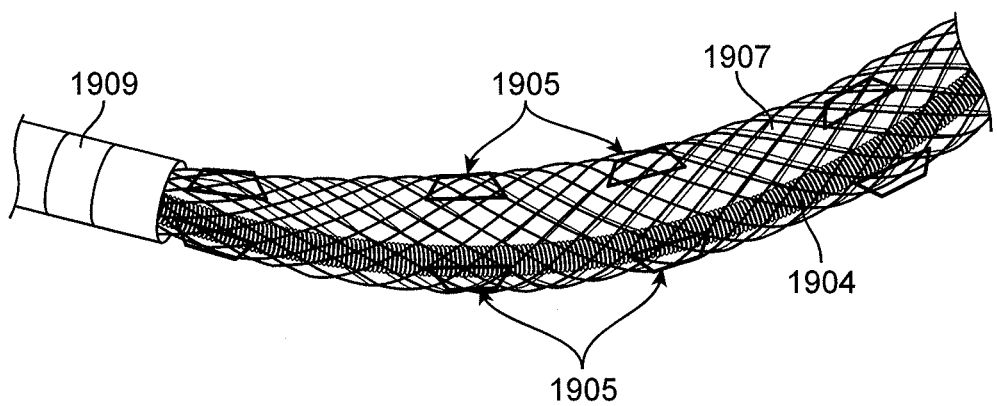
FIGS. 19A-19D schematically illustrate friction elements that may be included on the braided member portion of an implant.

For example, FIGS. 19A-19D illustrate variations of frictional elements that are coupled to an elongate, expandable braided member 1907. In FIG. 19A, a plurality of frictional elements 1905 are attached to the braided member 1907. In this example, the two frictional elements 1905 are located radially opposite each other (though more than two may be used) and multiple pairs (or sets) are attached to the braided member 1907 at longitudinally-offset positions within the inside of the braided member 1907. FIG. 19A shows the portion of the implant in an expanded configuration in which the braided member 1907 is expanded. Upon contraction and loading into a catheter, the friction elements may engage with the pushable member (inner member 1904 so that as the friction element is pushed or pulled (proximally/distally), within the catheter 1909, the braided member 1907 is moved along with it. This is illustrated in FIG. 20A, showing the expanded configuration of the braided member 1907 in an exemplary cross-section, and in collapsed/compressed configuration in FIG. 20B, within a catheter.

Figure 19B:
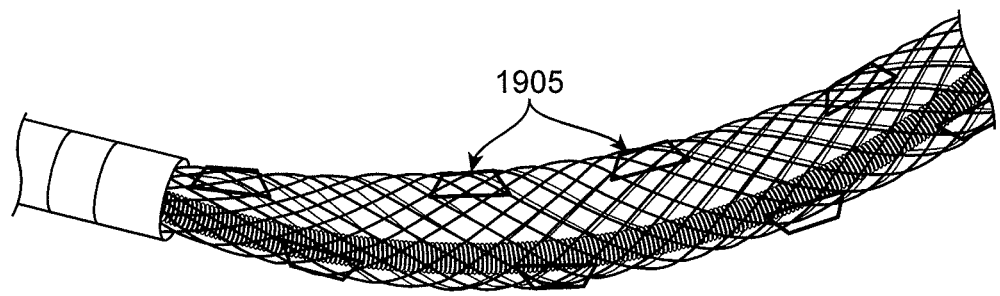
Figure 19C:
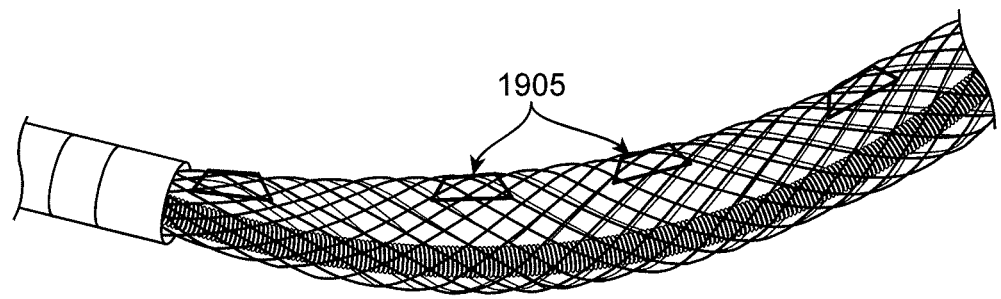
Figure 19D:
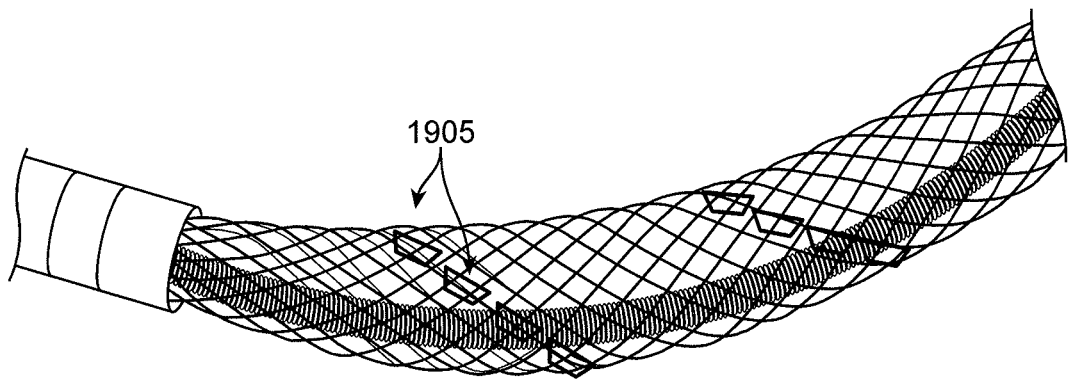
Figure 20A:
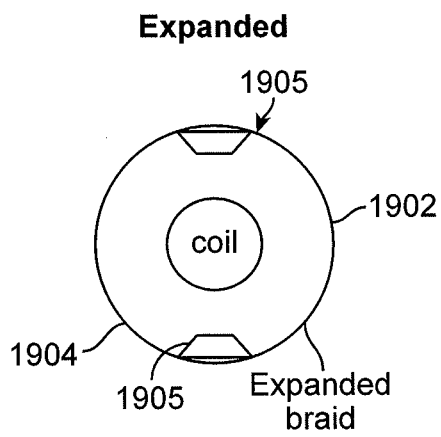
FIGS. 20A and 20B show sectional views of an implant including frictional elements on the braided portion such as the one shown in FIG. 19A in an expanded (FIG. 20A) and compressed (FIG. 20B) configuration, respectively.
Figure 20B:
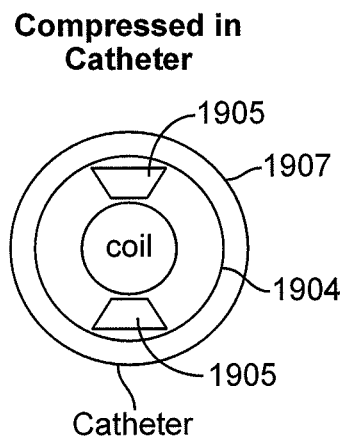

In FIG. 19B, the frictional elements 1905 are arranged at staggered locations along the length of the braided member 1907. Similarly in FIG. 19C, the friction elements 1905 are located on only one side of the braided member 1907. In FIG. 19D, the pattern of friction elements 1905 are arranged in a diagonal or spiral pattern within the braided member 1907.

Figure 21:
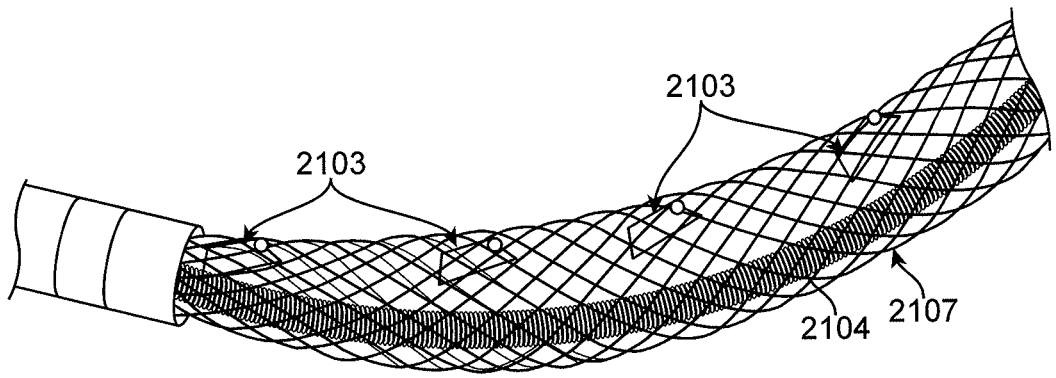
FIG. 21 is an example of a dynamic frictional element attached to a braided portion if a vaso-occlusive implant.

FIG. 21 shows another variation of a braided member having friction elements that are movable but coupled to the braided member. In this example, the friction elements are schematically illustrated and include a pivot point 2103 that is coupled to the braided member 2107. The friction elements can pivot down to jam into the pushable inner member (coil 2204) when the coil is pushed, and therefore constraining the braided member against the coil.

Figure 22A:
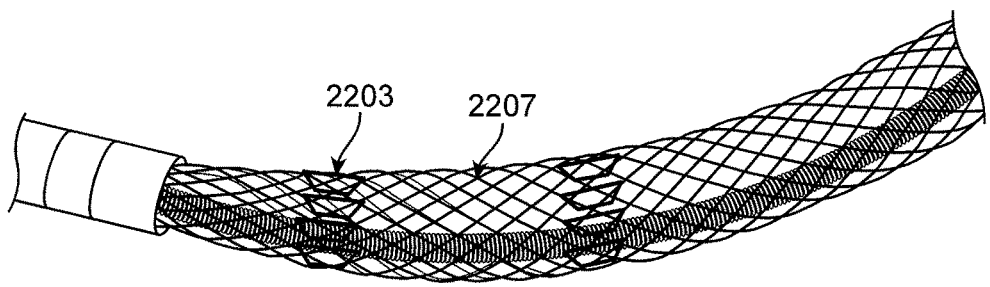
FIG. 22A is another example of a vaso-occlusive implant including a plurality of frictional elements attached to the braided member of the implant.
Figure 22B:
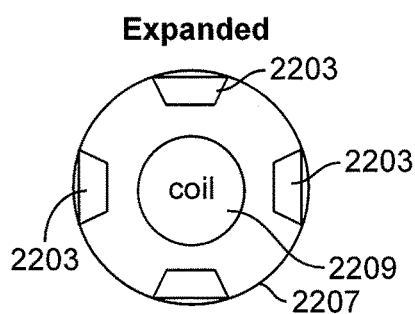
FIGS. 22B and 22C show schematics of sectional views of the implant of FIG. 22A in an expanded and compressed configuration, respectively.
Figure 22C:
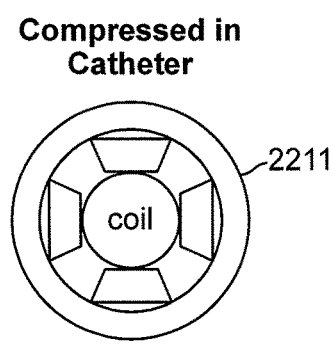

FIG. 22A shows another example of a braided member including a plurality of friction elements attached to the inner surface. In this example, four friction elements are arranged circumferentially around discrete longitudinally-spaced locations within the braided member 2207. As shown in FIGS. 22B and 22C, in the expanded state (FIG. 22B), the friction elements do not touch the inner member (coil 2209). FIG. 22C shows the braided member in the constrained/collapsed configuration within a catheter 2211, compressing the friction elements against the inner coil member (pushable member 2209).

Figure 23A:
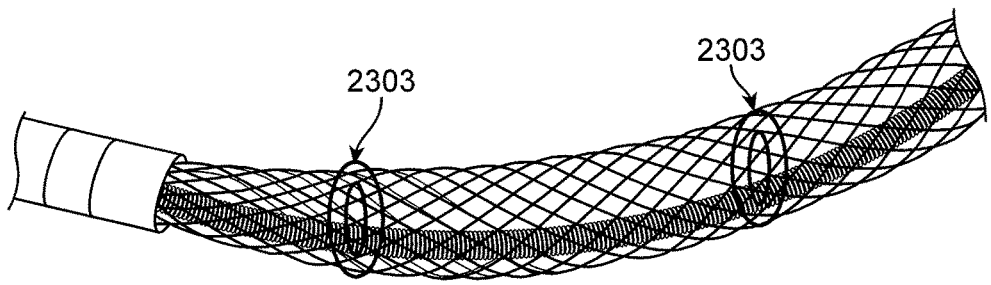
FIG. 23A is another example of a vaso-occlusive implant including a plurality of frictional elements attached to the braided member of the implant.
Figure 23B:
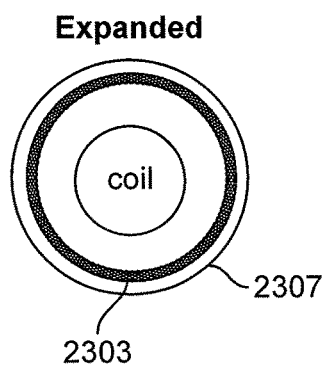
FIGS. 23B and 23C show schematics of sectional views of the implant of FIG. 23A in an expanded and compressed configuration, respectively.
Figure 23C:
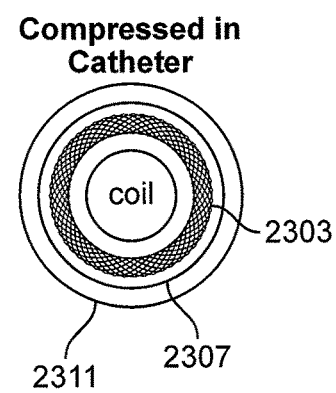

In addition to the discrete friction elements shown above, a friction element may also span more than one strand of the braided member. For example, in FIG. 23A annular (ring-shaped) friction elements, which may alternatively or additional be C-shaped or U-shaped, may be attached within the braided member to provide additional friction. FIGS. 23B and 23C illustrate the operation of the frictional elements in the expanded (FIG. 23B) and collapsed (FIG. 23C) configurations. In this example, the frictional element may be expandable or collapsible. For example, the friction element may be a rubber or rubber-like material. In some variations the frictional elements may aid in expanding the braided member when it is moved distally out of a catheter.

Figure 24A:
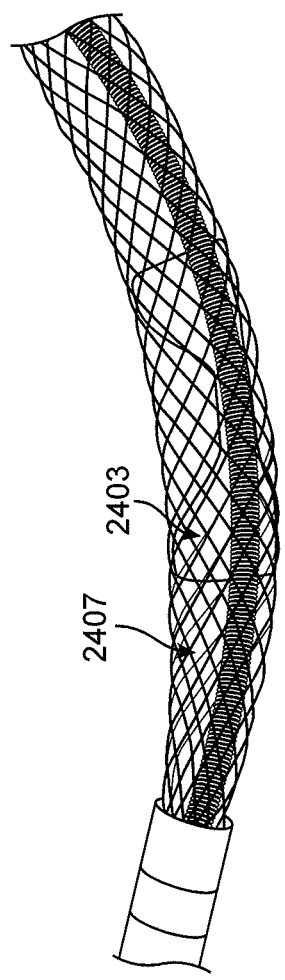
FIG. 24A is an example of a vaso-occlusive implant including a braided frictional element between the outer braided member and an inner pushable member of the implant.
Figures 24B, 24C:
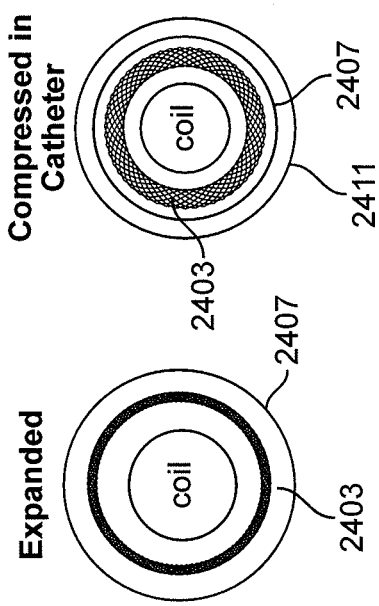
FIGS. 24B and 24C show schematics of sectional views of the implant of FIG. 24A in an expanded and compressed configuration, respectively.

Another alternative for a friction element within a braided member (and either free-floating or coupled to the braided member) is shown in FIGS. 24A-24E. In this example, the friction element 2403 is also formed of a braided structure (a flared or hour-glass profile structure) between the inner surface of the braided member 2407 and the inner pushable member 2404. FIGS. 24B and 24C illustrate the expanded and collapsed/constrained configurations, e.g., outside and inside of a catheter 2411. In FIGS. 24A-24E the friction element is a braided friction element that may be formed as discussed about for the outer braided members (e.g., of braided strands of material such as Nitinol.

Figure 24D:
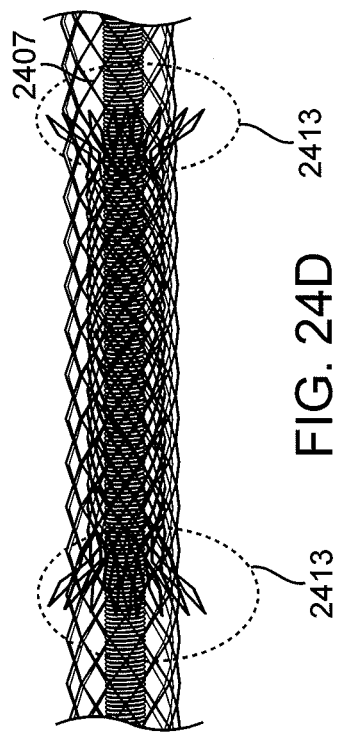
FIGS. 24D and 24E illustrate variations of frictional elements such as the one shown in FIG. 24A.
Figure 24E:
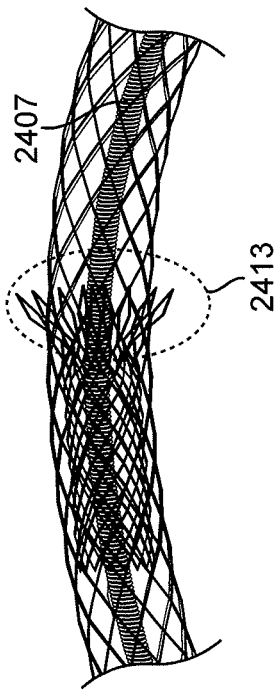

FIG. 24D illustrates a braided friction element in which the braid is a Nitinol braid with free ends 2413 that poke into the pores of the braided outer member 2407. In FIG. 24D, both ends of the friction element have free strands, while in FIG. 24E only one end includes free strands.

The example shown in FIG. 24 may be considered a free-floating friction element since the friction element does not need to be attached to the braided member, particularly when the braided member is expanded. Another example of a free-floating friction element is shown in FIGS. 25A-25C. In this example, a free-floating friction element 2503 is positioned between the outer braided member 2507 and the inner pushable member (coil 2505). The friction element may be any appropriate shape that is retained within this space; for example, the frictional element may be a tubular foam material or short section of Nitinol or Pt braid that has a smaller diameter compared to the outer braided member. In FIGS. 25A-25B the friction member is a free-floating annual (ring-shape); other shaped, including C-shapes, U-shapes, crescent-shapes, etc. may be used. The shapes may be symmetrically positioned around the central coil or they may be asymmetric (e.g., present only one side).

In general the friction elements described herein are configured to at least partially fill the space between the outer braided member and the inner pushable member when the implant is held within a catheter.

Part III: Vaso-Occlusive Devices Coupled Off-Axis to Pushable Member

Figure 26A:
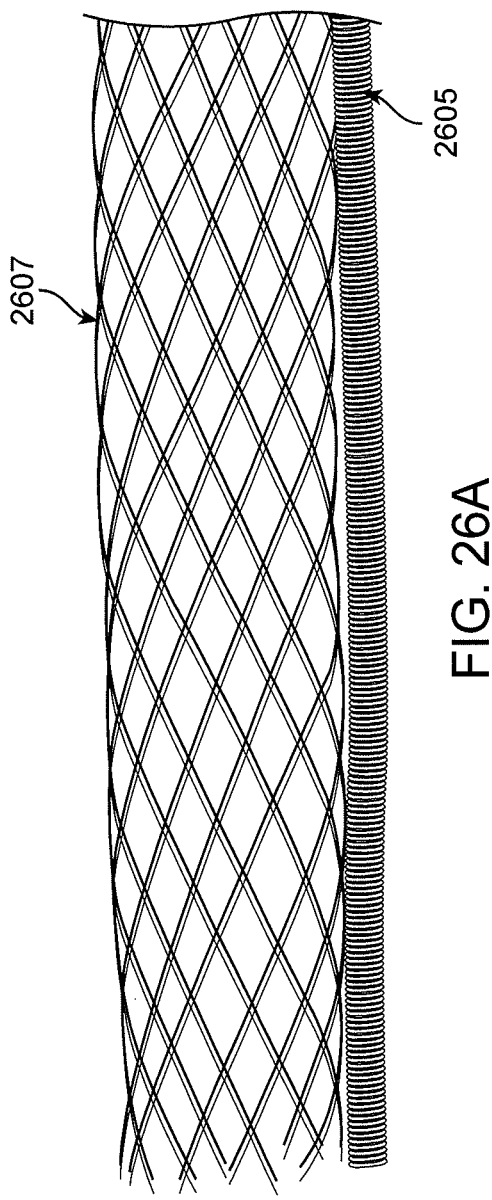
FIGS. 26A and 26B show schematic examples of a vaso-occlusive implant in which the pushable member and the expandable braided member are connected along their length in an off-axis configuration.
Figure 26B:
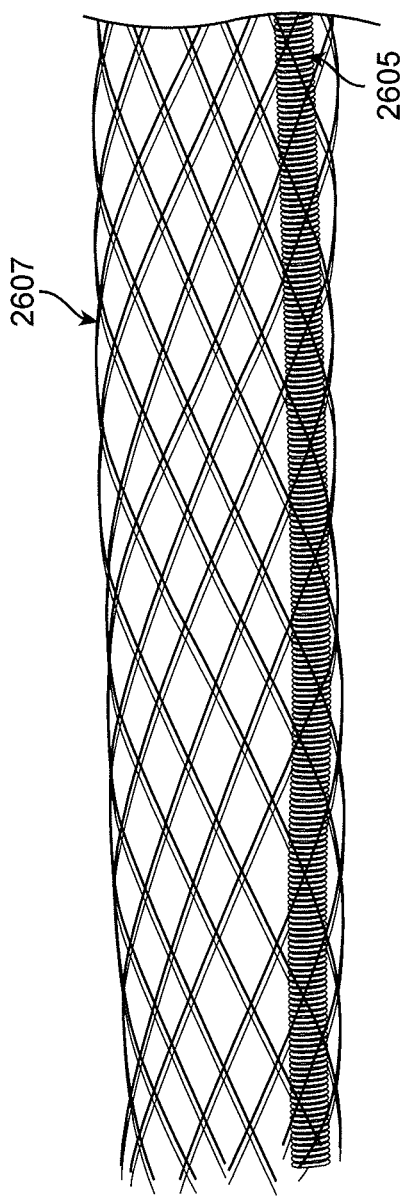

Also described herein are vaso-occlusive devices in which the pushable member (e.g., coil) and the expandable braided member are not symmetrically coaxially arranged, but are instead connected along their length in an off-axis configuration. An example of this is shown in FIGS. 26A and 26B. In FIG. 26A, the expandable, elongate and soft braided member 2607 is schematically illustrated and is attached along its length to an elongate pushable member (e.g., coil). In FIG. 26A the braided member 2607 is connected along an outer side to the pushable member 2605. The length of pushable member is typically longer than the length of braided member, and thus multiple regions of braided member may be included, as discussed above. Further, the ends of the braided member may be free, exposing the strand ends; in some variations the proximal end of the braided member(s) are attached to the pushable member, which may make the implant easier to withdraw into the catheter.

In FIG. 26B, the braided member is attached to the pushable member 2605 along an inner region of the braided member. The braided member may be attached along its length at all or a subset of the locations in which strands of the braided member cross the pushable member. Although in FIGS. 26A and 26B the pushable member is attached to the braided member in a line, the braided member and pushable member may be attached in a curve or helical attachment pattern.

Any of the braided members described herein may be used, having any appropriate number of strands (and pore sizes). Further, the braided member may be of any appropriate expanded diameter and collapsed diameter described above (e.g., the expanded diameter of the braided member may be between about 0.7 mm and about 5 mm, etc.). The pushable member may be formed as describe above; for example, the pushable member may be formed of a soft Pt coil.

Methods of Use

In general, any of the apparatuses described herein can be inserted into an aneurysm of a blood vessel with the intent of embolizing the aneurysm. Separate implants (stents) can be placed across the neck of the aneurysm. Due to their ability to expand once deployed outside of the delivery system or deployment tool these implants have the advantage of filling an aneurysm with less length than a non-expanding coil device. Also, the porous structure formed by the stent portion of the stent coil can be more effective than a solid structure like a coil in achieving inter-aneurysmal hemostasis due to its inherent interstices.

These implants are typically sufficiently soft so as not to damage the aneurysm or surrounding vascular wall. In general, deployment of implants (stent coil devices) can be difficult if the stent coil devices are not sufficiently rigid to sustain pushing or the stent coil is too long, such as in excess of 10 cm. The stent coil devices described herein may be loaded into catheters and delivered to the aneurysm by pushing on the proximal end of the pushable member with another implant or a pusher element.

Any of the embolic devices described herein can be formed into one or more configurations along the length of the embolic device. In addition, the embolic devices described herein can have a compact or delivery diameter, for example when the device is compacted into a catheter during delivery to a target site. The delivery diameter can be from about 0.1 mm to about 1.0 mm, more narrowly from about 0.2 mm to about 0.8 mm, more narrowly from about 0.25 mm to about 0.69 mm, for example about 0.5 mm.

The embolic devices described herein can be configured to expand radially by factors from about 1.5 to about 20 times, for example about 5 times the delivery diameter when not constrained inside of the catheter compared to when constrained by the catheter. The braided members of the embolic devices can be made by weaving, knitting or braiding filaments into tubes and shaping them. For example, the filaments can have diameters less than about 0.001 in. The tubes can be annealed into more complex 3-D shapes, such as shown. These embolic devices, can be highly flexible, able to conform to a tight 2 mm radius without damaging or plastically deforming the device shape and porous structures, with pore sizes ranging from about 0.01 mm to about 0.25 mm. The distal end of the embolic devices, for example the first end of the embolic device deployed into the aneurysm sack, can have a fabric anchor. The fabric anchor can be configured to seat or keep the device in the sack and not escaping after the device is positioned into the target aneurysm sack. The fabric anchor can lodge in the mouth of the sack, obstructing the mouth and preventing the remainder of the device from escaping the aneurysm.

In some examples, a typical 7 mm in diameter aneurysm can be filled with about one to about four, for example about three of the embolic devices. The embolic device can interlock with other embolic devices and may tend to stay within the aneurysm sack. The embolic devices can be used to fill larger neck aneurysms. The embolic devices can interlock with each other. The embolic device, such as the stent-coils described above ("implants"), for example due to their self-expanding nature, can resist coil compaction inside of the aneurysm. Coil compaction in the aneurysm space, which is a common problem with typical coils and can occur weeks, months or years after the embolization, resulting in the need for additional embolizations of the aneurysm to reduce its risk of future rupture. The embolic devices described herein can be used with a frame the inside of the aneurysm like a vessel liner, for example to block subsequently deployed embolic devices movement out the neck of the aneurysm. The stent-coil can be placed near the neck of the aneurysm. The porous outside layer of the stent-coil structure can enhance the ability to heal the aneurysm by providing a scaffold for new cell growth and attachment. The stent-coil structure can be placed inside the aneurysm neck or inside the parent vessel to aid in vessel occlusion in arterial venous malformations, fistulas or to any target where it is desirable to slow or arrest blood flow. When treating aneurysms the stent-coil deployed inside the aneurysm can reduce the risk of a subsequent stroke and the need for putting the patient on long term blood thinner or anti-coagulants as compared to placing a flow diverting stents in the parent artery at the mouth of the aneurysm.

An embolic device can be filled with a filler before or after deployment in the aneurysm.

An embolic device can have radiopaque and/or echogenic visualization markers. The fibers of the embolic device can be made from interbraided wire, for example made from platinum, platinum alloys (e.g., platinum-iridium alloy), and gold. The deployment tools, such as the catheters, pushers and mandrels, can have one or more markers. The embolic devices can be inserted into multiple vascular target sites to embolize aneurysm sacks. A first embolic device can be inserted into a first aneurysm and a second embolic device can be inserted into a second aneurysm.

Any or all elements of the embolic devices described above and/or other devices or apparatuses described herein can be made from, for example, platinum, platinum alloys for example with gold filaments, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (e.g., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold. An embolic device can be made from substantially 100% PEEK, substantially 100% titanium or titanium alloy, or combinations thereof.

The embolic device can be made partially or completely from biodegradable and/or bioabsorbable materials.

Any or all elements of the embolic devices and/or other devices or apparatuses described herein, can be, have, and/or be completely or partially coated with agents for adhesion, cell ingrowth, cell toxicity (e.g., cytostatic and/or cytotoxic) or combinations thereof.

The embolic devices and/or elements of the device and/or other devices or apparatuses described herein can be filled, coated, layered and/or otherwise made with and/or from fillers and/or glues known to one having ordinary skill in the art and/or a therapeutic and/or diagnostic agent. Any of these fillers and/or glues can include growth factors.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostaglandin E2 Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Figure 27A:
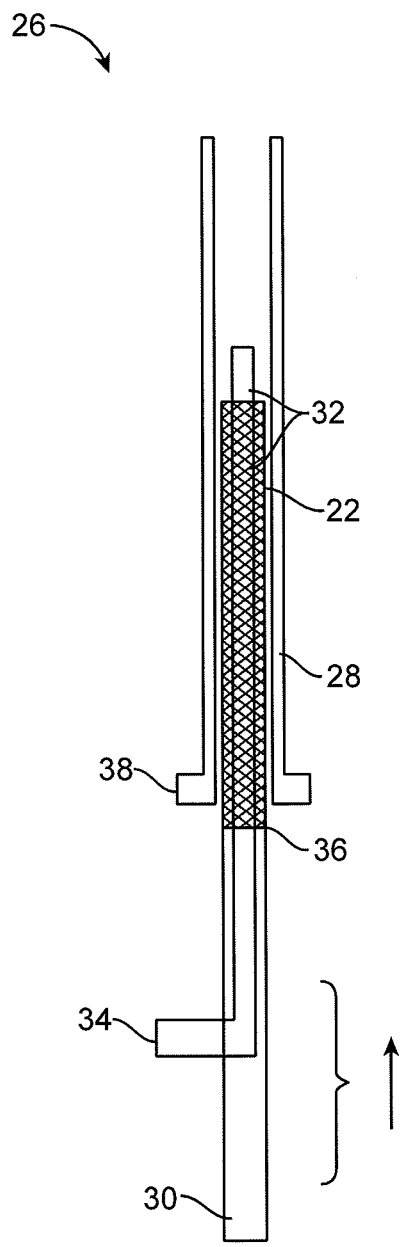
Figure 27B:
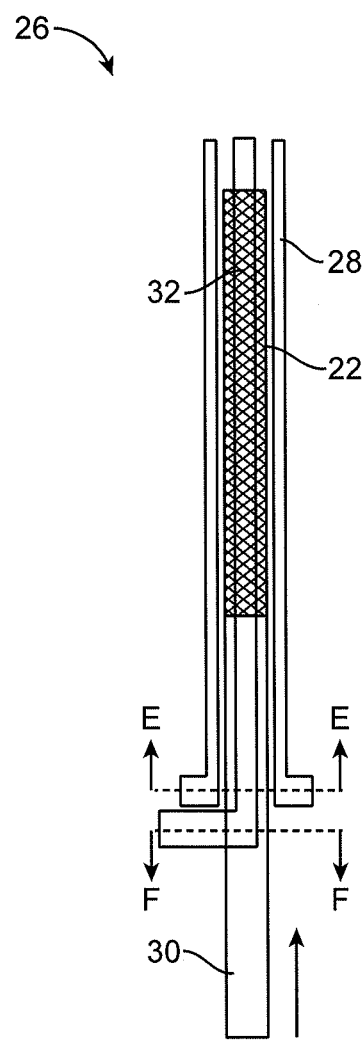

FIGS. 27A and 27B illustrate that the embolic device 22 can be loaded into a deployment device or deployment tool 26 for inserting and deployment into a target site. The target site can be a vascular aneurysm. The deployment tool 26 can have a catheter 28, a coil or other pusher 30, a support mandrel 32, and combinations thereof. The embolic device 22 can be a braided configuration. The support mandrel 32 can have an outer diameter about equal to the inner diameter of the embolic device 22. The embolic device 22 can float over the mandrel 32, e.g., the gap distance between the mandrel 32 and braid or other embolic device 22 can be from about 0.001 in. to about 0.010 in. The embolic device 22 can be fitted onto and frictionally attached (e.g., from the tight fit) to the support mandrel 32 before deployment. The embolic device 22 can translatably slide with respect to the support mandrel 32 if the friction resistance between the mandrel 32 and the embolic device 22 is overcome. The support mandrel 32 can have a support mandrel hub 34 or handle extending radially from the remainder of the mandrel 32. The support mandrel hub 34 can be proximal of the embolic device 22. The support mandrel 32, for example via the support mandrel hub 34, can be longitudinally translatably fixed to the pusher 30.

The pusher 30 can be slidably placed over the proximal end of the support mandrel 32. The distal end of the pusher 30 can abut, and/or be rigidly attached to the proximal end of the embolic device 22 at the abutment point 36. The pusher 30 can have an inner diameter approximately equal to the inner diameter of the embolic device 22. The pusher 30 can have an outer diameter equal to or greater than the outer diameter of the embolic device 22. The embolic device 22 can be releasably attached to the pusher 30. The catheter 28 can have a catheter hub 38 at the proximal end of the catheter.

The pusher 30 and mandrel 32 can be translated longitudinally concurrently, as shown by arrow.

FIG. 27B illustrates that the pusher 30 can be translatably pushed longitudinally with respect to the catheter 28, as shown by arrow. Driven by the pusher 30, the mandrel 32 and embolic device 22 can translate with respect to the catheter 28, for example, until the support mandrel hub 34 abuts the catheter hub 38. The tight fit of the support mandrel 32 inside the embolic device 22 can prevent the embolic device 22 from buckling inward or outward (since outward buckling requires inward buckling).

FIGS. 27C and 27D illustrate that the pusher can fit between the support mandrel 32 and the catheter 28. The support mandrel 32 can be almost complete encircled or completely encircled along a part of the length of the support mandrel 32 by the pusher 30. The pusher 30 can also have a pusher slot 40. The support mandrel hub 34 can slide through the pusher slot 40, for example to limit the travel distance of the mandrel 32 (e.g., the pusher slot 40 can extend along part, but not all of the length of the pusher 30, for example, to prevent the mandrel 32 from sliding out of the proximal and/or distal ends of the pusher 30). The mandrel 32 can be positioned in, and/or distal to, and/or proximal to the catheter 28. The mandrel 32 can be retained by the catheter 28, for example, so as not to be implanted with the embolic device 22.

FIG. 27E illustrates that the pusher 30 can continue to push, as shown by arrow, the embolic device 22 after the support mandrel hub 34 has abutted the catheter hub 38. The pusher 30 can longitudinally translate with respect to the mandrel 32, pushing the embolic device 22 out of the distal end of the catheter 28 and off of the distal end of the support mandrel 32. The distal end of the support mandrel 32 can remain in the catheter 28. The embolic device 22 can be retracted into the catheter 22 by the pusher 30, for example to reposition the embolic device 22 at the target site.

Figures 27F, 28A:
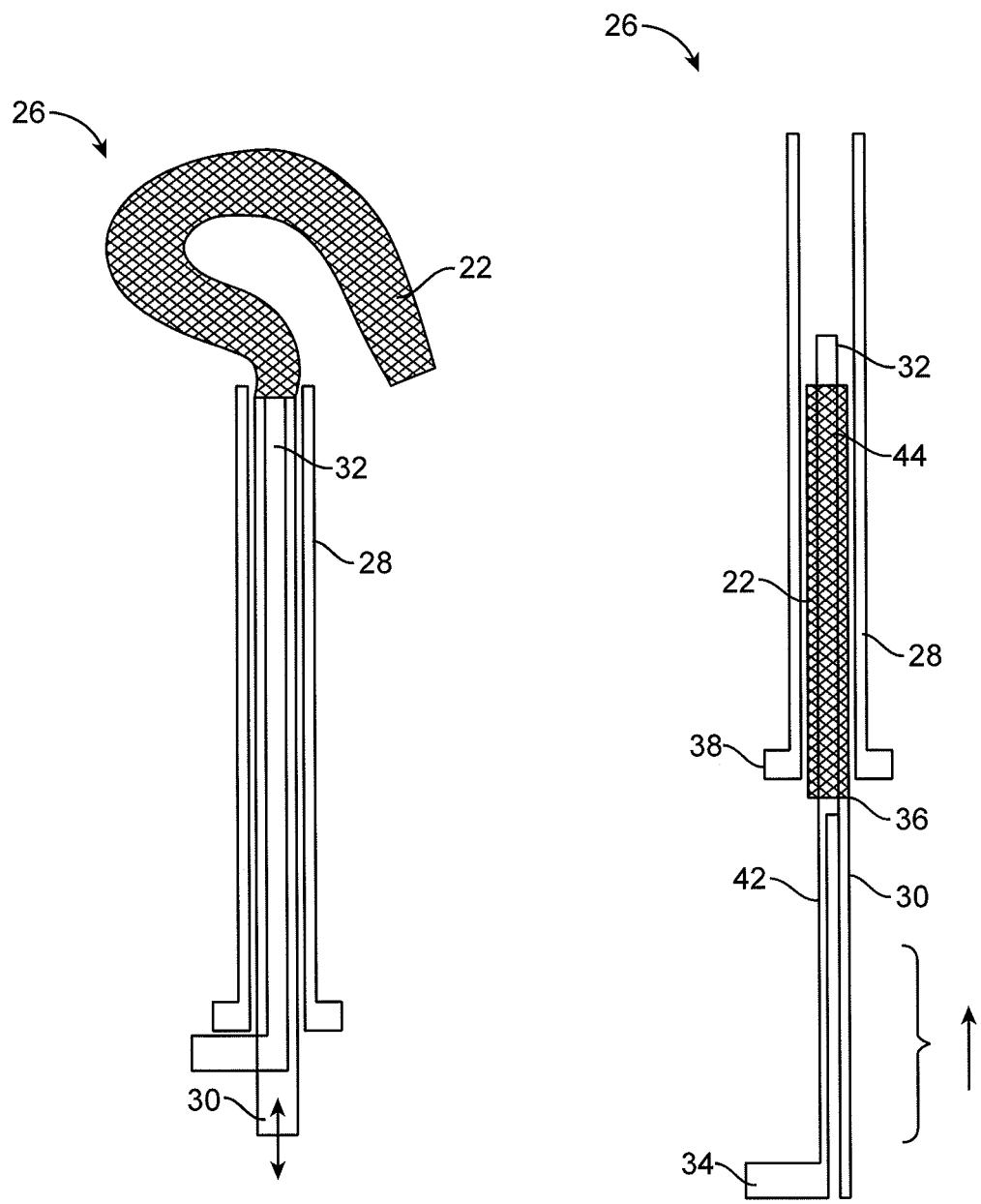

FIG. 27F illustrates that the pusher 30 can continue to push, as shown by advancing arrow, the embolic device 22. The embolic device 22 can be fully delivered out of the catheter 28. The embolic device 22 can be detached from the pusher 30. The embolic device 22 can self-expand (e.g., radially while contracting longitudinally) when released from the constraints of the support mandrel 32 and the catheter 28. The pusher 30 and the remainder of the deployment tool 26 can be withdrawn from the catheter 28, target site and/or patient, as shown by retracting arrow.

Figures 28B, 28C, 28D:
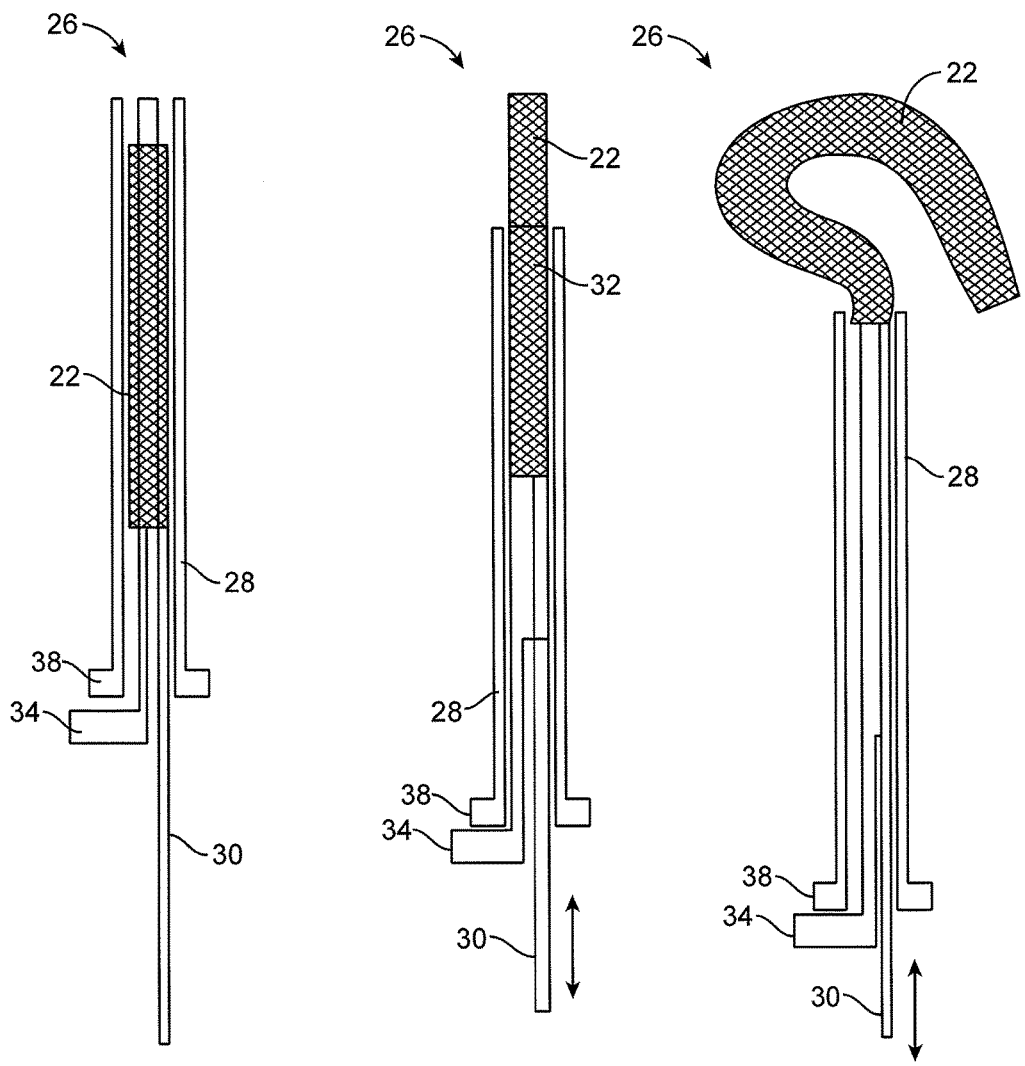

FIGS. 28A-28B illustrate that the embolic device 22 can be deployed by a deployment tool 26 similar to the deployment tool 26 shown in FIGS. 27A-27F, except the body of the mandrel 32 co-extensive with the pusher 30 can be outside of the pusher 30. For example, the pusher 30 can be laterally adjacent to the mandrel 32. The support mandrel 32 can also have a support mandrel beam 42 extending between the support mandrel body 44 within the embolic device 22 and the support mandrel hub 34. The pusher 30 can releasably attach to the entire terminal circumference of the proximal end of the embolic device 22, or to only a fractional angular portion of the circumference. The pusher 30 and mandrel 32 can be translated longitudinally concurrently, as shown by arrow in FIG. 28A. The pusher 30 can be pushed or pulled (e.g., to withdraw the pusher and/or retract the embolic device 22), as shown by arrows in FIGS. 28C and 28D.

Figure 29A:
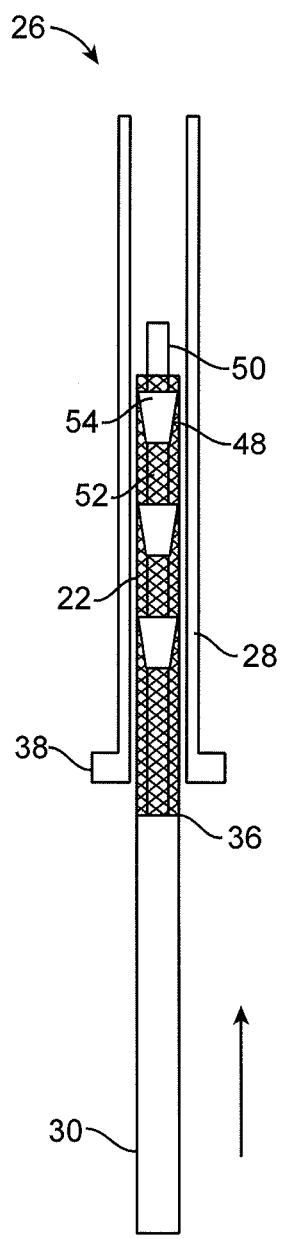
FIGS. 29A and 29B illustrate a method of deploying the embolic device with a variation of the deployment tool.

FIG. 29A illustrates that the embolic device 22 can have a braded member 48 (referred to in the figures as a braid, although the braided member can be braided, knitted, woven, or combinations thereof) and, optionally, a force-transfer element, such as a core 50. The force-transfer element or core 50 can be configured to transfer a distally translational force from the user (e.g., manually or automatically, such as from a motor), to the embolic device 22, and/or the braided member 48 (i.e., if the force-transfer element 50 is retained by the deployment device 26 during use and not deployed in the aneurysm). The force transfer or translation element 50 can have a leader 52 and a radial force transferor, such as a flare 54 or a bump, which can transfer the translational force from the leader 52 to the braided member 48. The force transfer element can be partially or completely radially interior to the braided member 48. The core 50 can be implanted with the braided member 48. The core 50 can also be a component of the deployment tool 26 instead and not implanted.

The core 50 can have a flexible, central extend member or leader 52, such as a flexible coil, rod, polymeric extrusion, other flexible elongated element, or combinations thereof, and one or more radial pressure members, such as flares 54, bumps or combinations thereof. For example, two, three or more flares 54 can be attached to the leader 52 at evenly spaced longitudinal lengths (e.g., every about 3 cm) along the core 50. The flares 54 can be radially expandable. The flares 54 can be configured to radially expand when the core is longitudinally translated distally within the catheter 28 and/or with respect to the braided member 48. The flares 54 can be configured to radially contract when the core 50 is longitudinally translated proximally with respect to the catheter 28 and/or the braided member 48.

The flares 54 can be attached to the core 50 at the proximal ends of the flares 54. The distal ends of the flares 54 can radially contract and expand. The distal ends of the flares 54 can releasably attach to the braided member 48. For example, the flare 54 can attach to the braided member 48 when the distal end of the flare 54 radially expands and the distal end of the flare 54 can radially engage with and attach to the braided member 48, while the proximal end of the flare 54 remains attached to the core 50.

The core 50 can be made from platinum, tantalum-doped polymer such as Nylon, polyester, or combinations thereof, or any other materials disclosed herein or combinations thereof. The core 50 can have a solid cross-section or be a hollow tube (e.g., to minimize structural rigidity). As the core 50 is longitudinally translated distally, the flares 54 can radially expand against the catheter 28 wall and drag or push the embolic device 22 (by transmitting force through the braided member 48) at the locations of the flare 54, for example to prevent or minimize buckling or longitudinal collapse of the embolic device 22 or braided member 48.

The pusher 30 can be longitudinally advanced, pushing the embolic device 22 distally. The pusher 30 can detached from direct connection with the embolic device 22 and retract (i.e., move proximally), in which case the flares 54 can radially retract and the embolic device 22 can remain longitudinally unmoved. In this manner, the embolic device 22 can be progressively translated distally in discrete increments as the pusher 30 can be repeated advanced a fraction of the length of catheter 28 and retracted in a ratcheting motion. As described herein, the coil pusher 30 can be used to push and pull the embolic device 22.

Figure 29B:
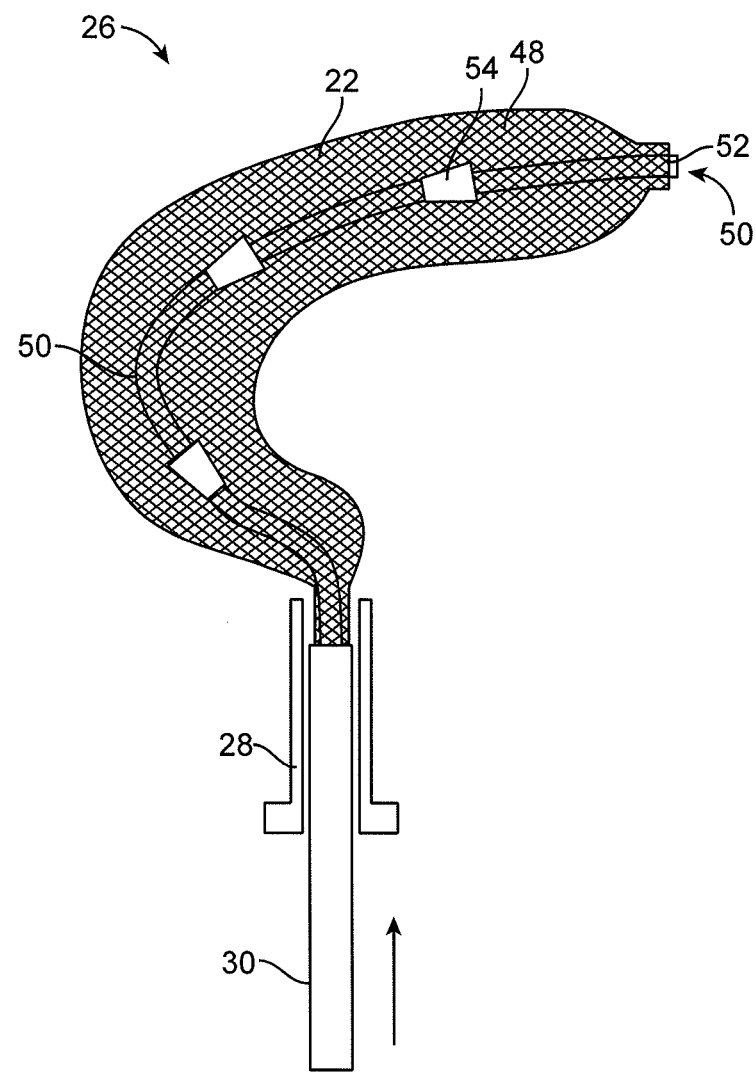

FIG. 29B illustrates that as the embolic device 22 exits the distal end of the catheter 28, the embolic device 22 (or braided member 48 in the situation where the core 50 is a portion of the embolic device 22) can radially expand and detach from the flares 54. The distal and/or proximal terminal ends of the embolic device 22 or braided member 48, can be releasably or non-releasably attached to the core 50.

Figures 30A, 30B:
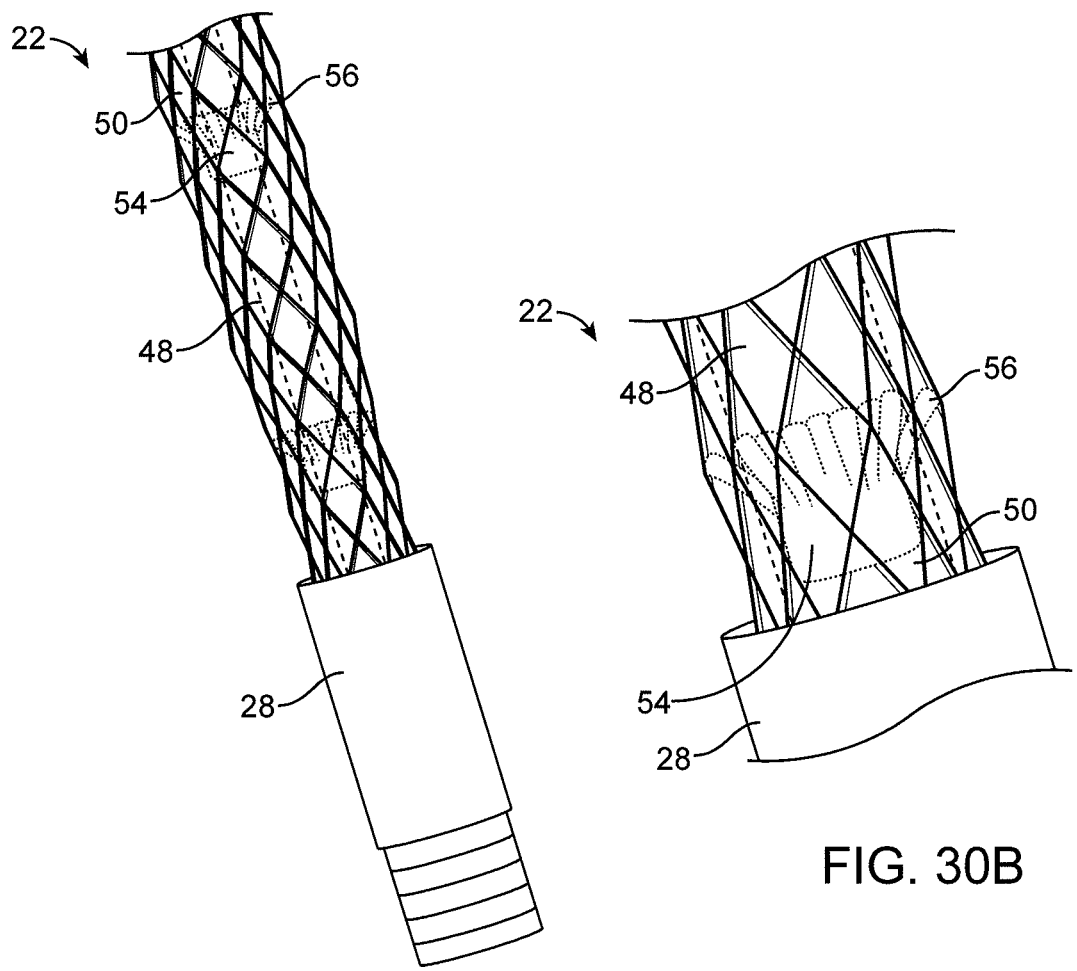
FIGS. 30A and 30B are a side view and a close-up side view, respectively, of a variation of an embolic device.

FIGS. 30A and 30B illustrate a variation of the embolic device 22 having the braided member 48, for example made from a braided material, and the core 50. The core 50 can be made from a coil (e.g., a platinum coil with or without a stretch-resistant element) or a solid or tubular rod (e.g., a polymer extrusion). The core 50 can be a guidewire (e.g., a Transcend EX from Boston Scientific of Natick, Mass.). The core 50 can have a core outer diameter from about 0.012 in to about 0.013 in, for example about 0.0125 in.

The flares 54 can be attached to the core 50. The flares 54 can have prongs 56 that can extend radially from the body of the flare 54. The prongs 56 can be configured to radially extend and retract. The prongs 56 can extend through the cells 58 of the braided member 48 when the prongs 56 are in a radially expanded configuration and the braided member 48 is in a radially contracted configuration.

Figure 31C:
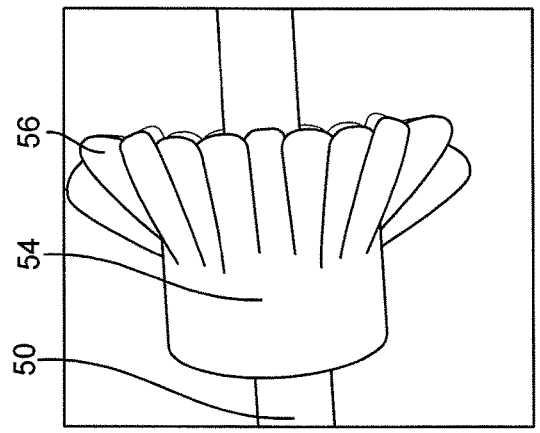
FIGS. 31A-31C illustrate a method of radial expansion of the distal end of a variation of a flare.
Figure 31B:
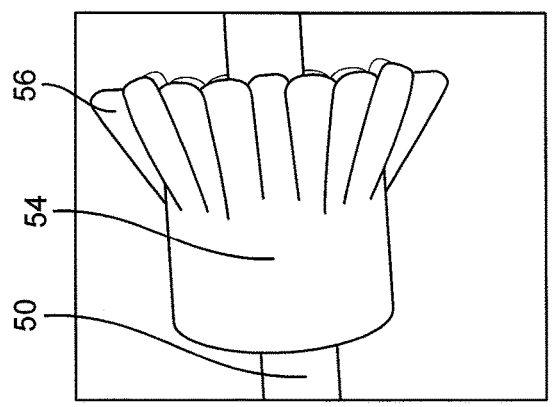
Figure 31A:
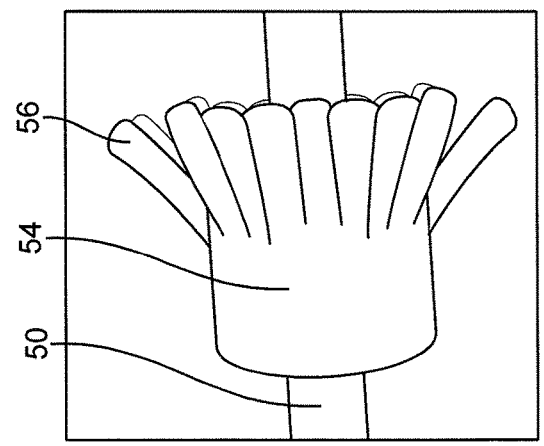

The braided member 48 can be made from a braid of wires 60, for example from about 16 to about 48, for example about 24 wires. The braided member 48 can have an outside diameter from about 0.0160 in to about 0.0170 in. in a contracted configuration, for example about 0.0165 in. The braided member 48 can have an outside diameter when heat set and undeformed from about 0.75 mm to about 1.2 mm. The wires 60 can be any material disclosed herein such a monofilament or multifilament polymer (e.g., PET, Nylon) or metal (e.g., platinum, Nitinol), a hybrid of materials in a single braid, or combinations thereof. The wires 60 can have a 0.001 in. diameter. The wires 60 can have a length of about 1.1 mm from intersecting one wire to the next wire. The embolic device 22 can be loaded into a catheter 28. The catheter 28 can have an inner diameter, such as from about 0.015 to about 0.025 in., for example about 0.019 in. FIGS. 31A through 31C illustrate that the proximal end of the flare 54 can be attached to the core 50. The distal end of the flare 54 can be radially expandable. The distal end of the flare 54 can have prongs 56 that can extend distally and radially. The flare 54 can be made from tubing (e.g., polyimide or any other material disclosed herein) and can be cut or frayed at the distal end of the flare 54 to form the prongs 56.

Figure 32B:
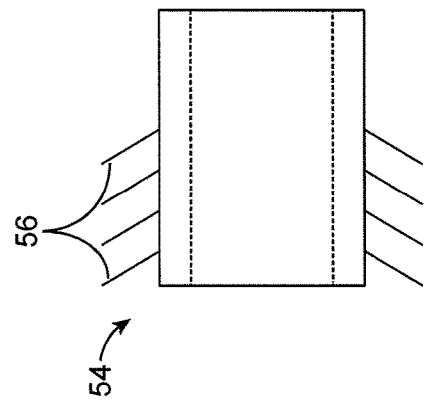
FIGS. 32A and 32B are front (i.e., longitudinally axial) and side views, respectively, of a variation of the flare.
Figure 32A:
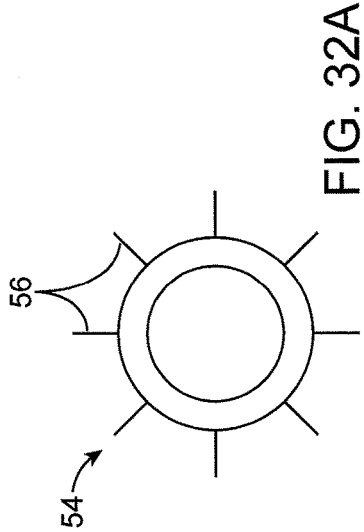

FIGS. 32A and 32B illustrate that the prongs 56 can be arranged into angularly aligned or misaligned rows extending proximally from the distal end of the flare 54. For example, the flare 54 can have four longitudinally-spaced rows of prongs 56. The prongs 56 can be angularly spaced evenly around the flare 54. For example, the center of the prong 56 can each extend away from the flare 54 at about 45° away from the center of the angularly-adjacent prong 56.

FIGS. 33A-33C illustrate that the flare 54 can be configured to push the braided member 48 or embolic device 22 with the prongs 56. The prongs 56 can be formed from the terminal ends of a flare braid 64. For example, the proximal end of the flare 54 can have a cohesion layer 62. The cohesion layer 62 can be polymer bonded to the proximal end of the flare braid 64. The distal end of the flare braid 64 can be out of the cohesion layer 62 with no polymer and can radially expand beyond the cohesion layer 62. The flare braid 64 can be inverted and form two flare braid layers (e.g., a radially inner layer and a radially outer layer) within the cohesion layer 62, as seen in FIGS. 33A and 33B.

FIGS. 34A and 34B illustrate a variation of the flare 54 similar to the flare in FIGS. 33A-33C except the flare braid 64 forms only one flare braid layer in the cohesion layer 62. The braided member 48 can be a braid having from about 8 to about 32 ends. The braided member 48 can be made from wires 60 or filaments that can have a diameter from about 0.0015 in to about 0.002 in, for example about 0.001 in.

Figure 35A:
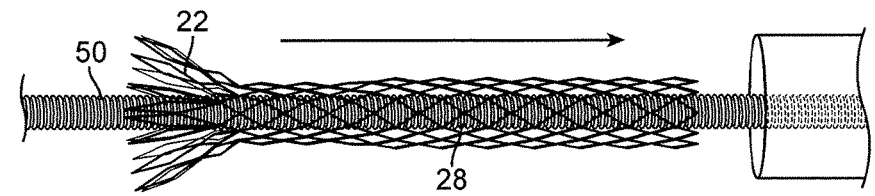
FIGS. 35A-35D illustrate a method of using the flare.
Figure 35B:
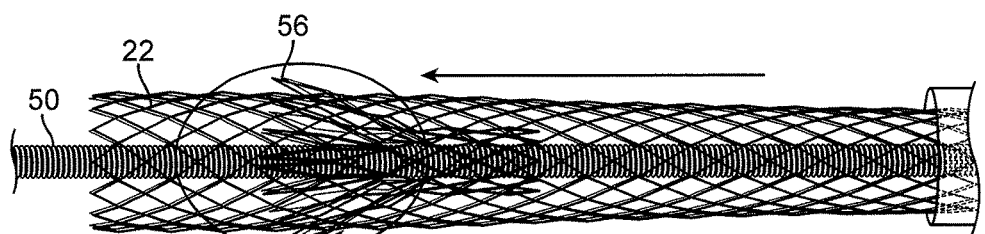
Figure 35C:
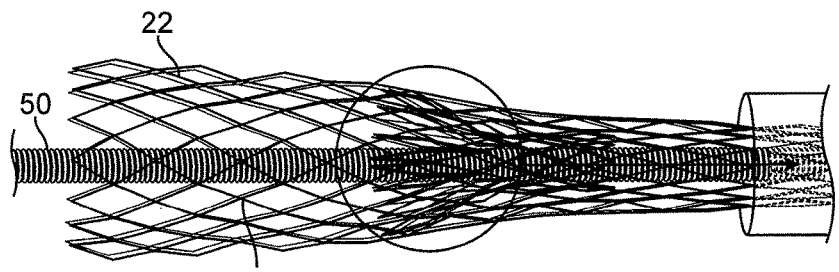
Figure 35D:
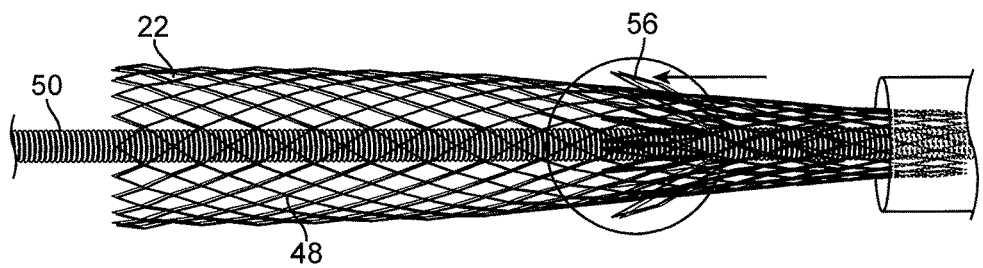

FIG. 35A illustrates that the catheter 28 can be retracted, as shown by arrow, from the embolic device 22. FIG. 35B illustrates that the embolic device 22 can radially expand and that the core 50 and flares 54 can be longitudinally advanced, as shown by arrow, with respect to the embolic device 22. The prongs 56 from the flare 54 can extend through the cells 58 in the braid of the braided member 48. The prongs 56 can engage the embolic device 22 and/or braided member 48 and attach the embolic device 22 and/or the braided member 48 to the core 50 via the flares 54. FIG. 35C illustrates that the core 50 can be retracted, as shown by arrow, with respect to the embolic device 22. The prongs 56 can be withdrawn from the cells 58 of the embolic device 22 and detach the embolic device 22 and/or the braided member 48 from the flares 54. FIG. 35D illustrates that the core 50 and flares 54 can be advanced again, as shown by arrow. The prongs 56 can radially expand and pass through cells 58 on the embolic device 22. The prongs 56 can attach to the embolic device 22 and/or the braided member 48 and connect the embolic device 22 and/or the braided member 48 to the core 50. The core 50 can push the embolic device 22.

FIG. 36A illustrates that the deployment tool 26 can have a support mandrel 32. The support or pushing mandrel 32 can have a flare 54 at the distal end of the mandrel 32. The flare 54 can be unidirectionally attached to the embolic device 22 and/or braided member 48, allowing relative translation only when the embolic device 22 and/or braided member 48 is moving distally with respect to the flare 54. The push mandrel 32 can have a push mandrel handle or hub 34. The push mandrel handle 34 can be controllably engaged between the puller 30 (i.e. the "pusher" in other variations can primarily pull the coil in tension in the present variation) and/or the push mandrel 32. The braided member 48 can be rigidly and detachably connected to the puller 30 at the abutment point 36. The abutment point 36 can be an abutment (i.e., denoting no overlap between the braided member 48 and the puller 30) or an overlap.

The deployment tool 26 can have the coil puller 30 that can be releasably attached to the proximal end of the embolic device 22. The push mandrel 32 can be longitudinally distally translated (i.e., advanced) through the catheter 28 with the puller 30 and the embolic device 22. The puller 30 can hold the embolic device 22 so that the embolic device 22 remains in tension between the flare 54 and the proximal end of the embolic device 22, for example to minimize kinking of the embolic device 22 in the catheter 28.

The puller 30 can be a passively dragged with the mandrel 32 when the mandrel 32 is initially advanced through the catheter 28. FIG. 36B illustrates that the push mandrel 32 can be longitudinally translated, as shown by arrow 78, along the catheter 28 while tension, as shown by arrow 80, remains on the puller 30.

FIG. 36C illustrates that when the embolic device 22 begins to exit the distal end of the catheter 28, the puller 30 and push mandrel 32 can be repeatedly placed in compression and tension, as shown by arrows, with each other to ratchet the embolic device 22 off the distal end of the push mandrel 32.

Figure 37A:
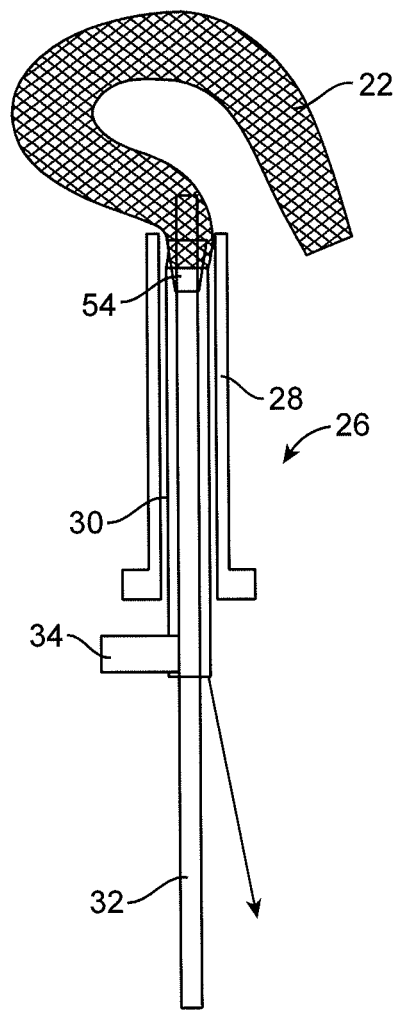
FIGS. 37A and 37B illustrate a method of deploying the embolic device with a variation of the deployment tool.

FIG. 37A illustrates that the embolic device 22 can be retrieved after deployment out of the catheter 28. For example, if the puller 30 is attached to the proximal end of the embolic device 22, the flare 54 can engage the embolic device 22 and deliver tension on the embolic device 22 between the flare 54 and the puller 30. The push mandrel handle 34 can be configured to manipulatibly longitudinally fix the push mandrel 32 to the puller 30, for example by squeezing the mandrel handle 34. The puller 30 can then be retracted while longitudinally fixed with respect to the mandrel 32, as shown by arrow. The embolic device 22 in tension will radially contract. The radially contracted embolic device 22 can fit within the catheter 28. The puller 30 can then retract a contracted length of the embolic device 22 into the catheter 28.

Figure 37B:
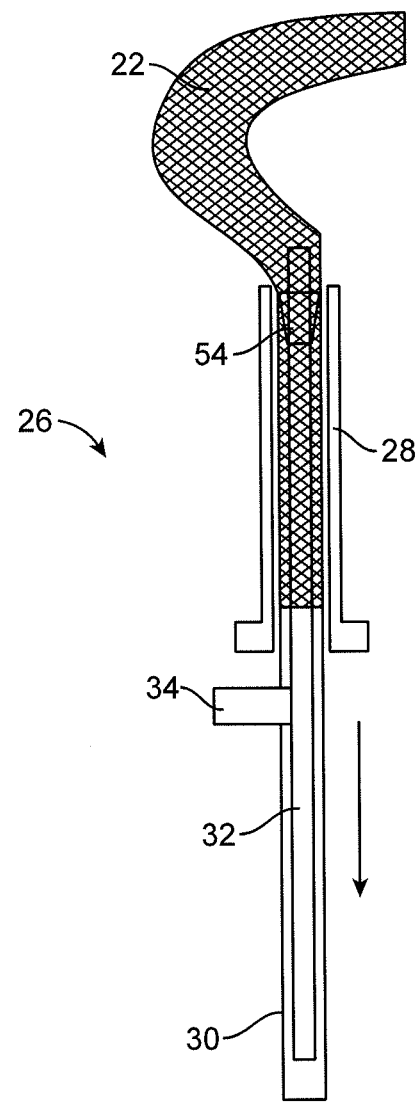

FIG. 37B illustrates that the flare 54 can be compliant during retraction of the puller 30 so the embolic device 22 can slide over the flare 54. The push mandrel handle 34 can be manipulated to control between locking the push mandrel 32 to the puller 30 and controlling either the puller 30 or the push mandrel 32 alone.

Figure 38A:
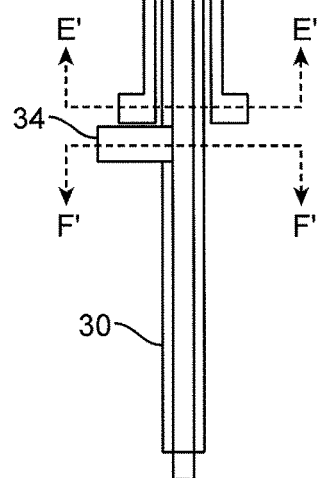
FIG. 38A illustrates a variation of the embolic device loaded on a deployment tool.
Figure 38B:
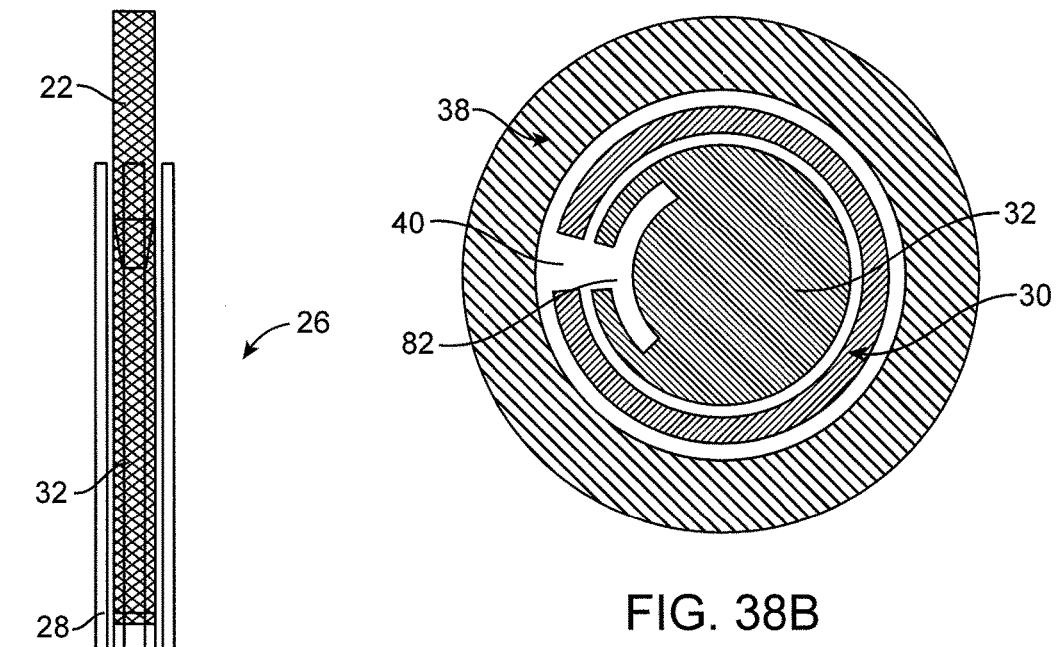
FIGS. 38B and 38C are variations of cross-sections E'-E' and F'-F1, respectively, of FIG. 38A.
Figure 38C:
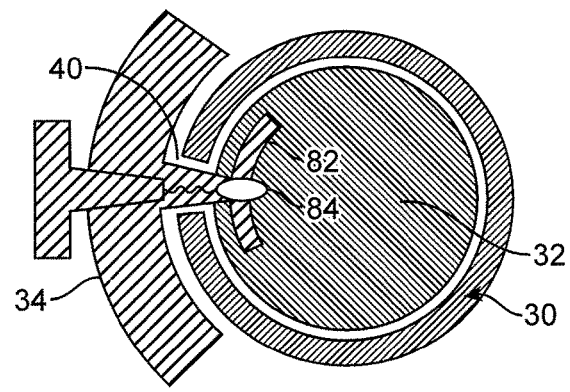

FIGS. 38A and 38B illustrate that the push mandrel 32 can have a longitudinal push mandrel slot 82. The push mandrel slot 82 can extend along part or all of the push mandrel length. The puller 30 can have a puller slot 40. The puller slot 40 can be aligned with the push mandrel slot 82. FIG. 38C illustrates that the push mandrel handle 34 can be slidably received by the puller slot 40 and the push mandrel slot 82. The push mandrel handle 34 can have a handle engagement element 84, such as a spring-loaded key, rod or ratchet pawl. The push mandrel handle 34 can controllably attach to and detach from the push mandrel 32, the puller 30 or both, for example to longitudinally fix and unfix the push mandrel 32 to the puller 30.

Figure 39:
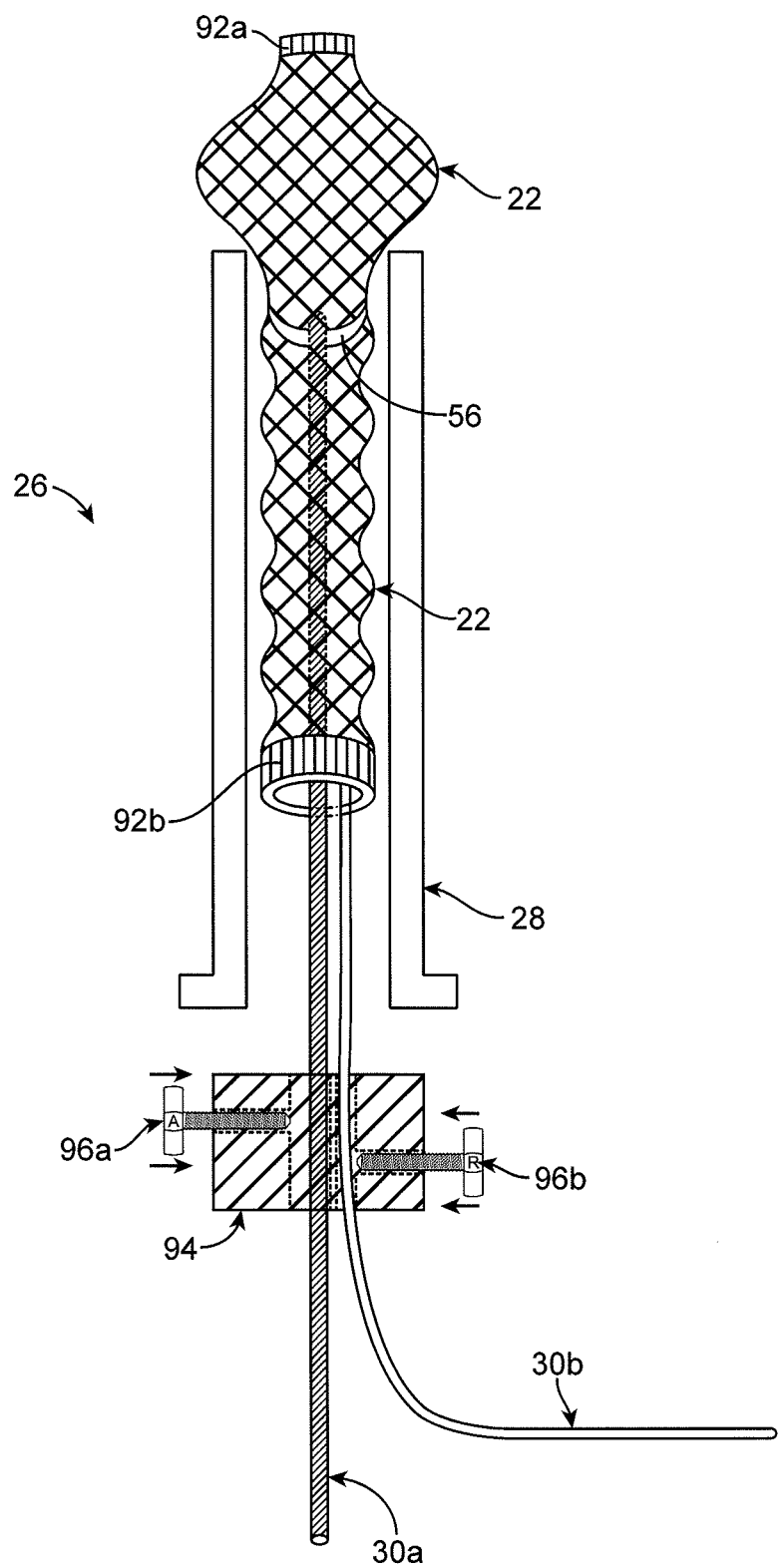
FIG. 39 illustrates a variation of the deployment tool and the embolic device.

FIG. 39 illustrates that the embolic device 22 can have two prongs 56 extending bilaterally from the pusher 30a. The prongs 56 can be as shown or any other prongs or pushing mechanism shown herein, such as the prongs 56 shown and described above. The prongs 56 can be flexible and radially extendable and retractable. The prongs 56 can have a convex, arced, or crescent configuration. The prongs 56 can be configured to unidirectionally interface the embolic device 22 and/or braided member 48. For example, the prongs 56 can engage the embolic device 22 and transfer force from the pusher 30a to the embolic device 22 when the pusher 30a is translated distally and the prongs 56 can disengage the embolic device 22 when the pusher 30a is translated proximally. The pusher 30a can be rigid, for example a rigid rod or beam. The puller 30b can be rigid or flexible, for example a linkage, cord, fabric or polymer ribbon, or combinations thereof. The embolic device 22 can have one or more flexible or rigid device collars 92, for example at the distal terminal end and/or the proximal terminal end of the embolic device 22 or braided member 48. The proximal device collar 92b can be attached to a puller wire or lead extending proximally from the proximal device collar 92b.

The deployment tool 26 can have a translational controller 94. The translational controller 94 can be slidably attached with the pusher 30a and the puller 30b. The translational controller 94 can have a pusher advancement control. The pusher advancement control 96a can be a knob or button that can pressure fit against the pusher 30a to lock the pusher 30a and/or translate the pusher 30a. The translational controller 94 can have a puller retraction control 96b. The puller retraction control 96b can be a knob or button that can pressure fit against the puller 30b to lock the puller 30b and/or translate the puller 30b.

FIG. 40A illustrates a variation of the deployment tool 26 and embolic device 22 similar to those shown in FIG. 39 (the translational controller 94 is not shown for illustrative purposes). The pusher 30b can be translated, as shown by arrow 98, in a distal direction. The prongs 56 can transfer distal force from the pusher 30a to the embolic device 22. The embolic device 22 can be translated, as shown by arrow 100, distally, out of the distal end of the catheter 28. The prongs 56 can be positioned near the distal end of the catheter 28. The puller 30b can have a proximally-directed force applied to maintain tension in the length of the embolic device 22 proximal to the prongs 56.

FIG. 40B illustrates that the pusher 30a can be retracted (i.e., translated proximally), as shown by arrow, with respect to the catheter 28 and the embolic device 22, for example to reset the position of the pusher 30a to prepare to push more length of the embolic device 22 out of the catheter 28. The ratchet length or stroke length between the prongs 56 (or any fixed point on the rigid pusher 30a) at a distal-most position and at a proximal-most position during use can be from about 3 cm to about 15 cm, for example about 5 cm. If the prongs 56 are retracted too far, the embolic device 22 distal to the prongs 56 can longitudinally collapse, jam or crumple (e.g., because of insufficient column strength). The embolic device 22 can block the catheter 28 or otherwise impair distal translation of the embolic device 22.

FIG. 40C illustrates that a contraction sheath 102 can be distally translated between the puller 30b and the embolic device 22. The contraction sheath 102 can be a rigid or semi-rigid and semi-flexible cylindrical configuration. The contraction sheath 102 can be distally translated at least until the contraction sheath 102 longitudinally overlaps the prongs 56. The contraction sheath 102 can press the prongs distally and inwardly, radially contracting the prongs 56. The radially contracted prongs 56 can be disengaged and unattached from the embolic device 22.

FIG. 40D illustrates that the pusher 30a can be distally translated with the contraction sheath 102, as shown by arrows, translating the contracted prongs 56 distally. When the pusher 30a and the prongs 56 are at a desired longitudinal position, the contraction sheath 102 can be retracted, releasing the prongs 56. The prongs 56 can radially expand and unidirectionally engage with and attach to the embolic device 22, as shown in FIG. 40A.

While the pusher 30a and prongs 56 are retracting, as shown in FIG. 40B, and/or while the prongs 56 are in the contraction sheath 102, the puller 30b can be proximally pulled to retract the embolic device 22 into the catheter 28.

Figure 41A:
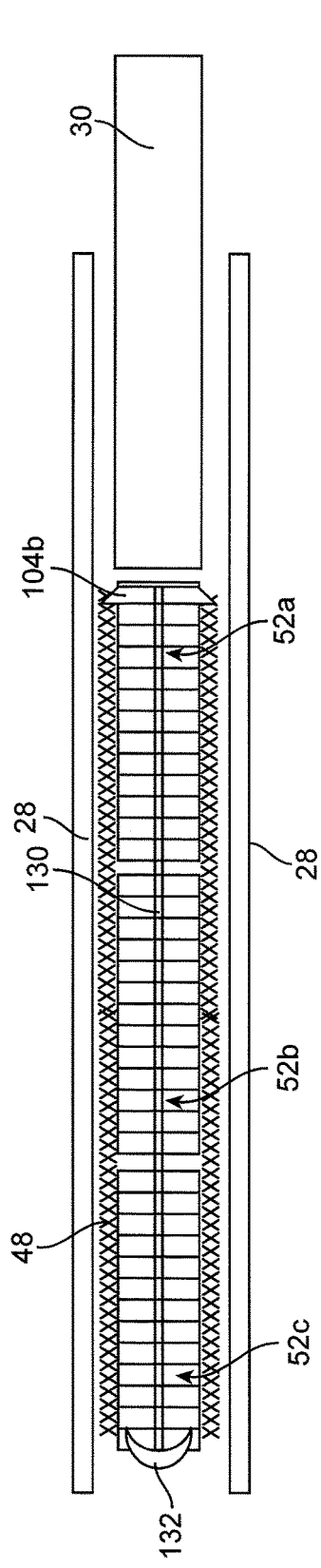
FIGS. 41A and 41B are cross-sectional views of a method of deploying the embolic device with a variation of the deployment tool.
Figure 41B:
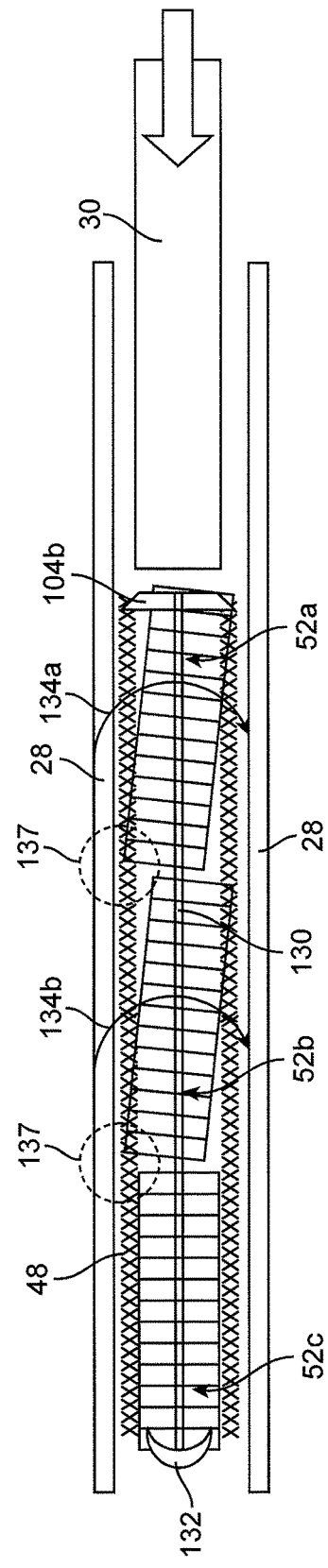

FIGS. 41A and 41B illustrate a device and method for deploying the braided member 48. The mandrel 32 can have radially extending pushing spines 146 (e.g., fingers). The spines can extend distally and proximally. The pushing spines can engage the braided member 48 and act as pushing or pulling elements for ratcheting the layer 48 distally or proximally. A hypotube 148 inside of the catheter 28 can prevent premature extension of the spines.

FIG. 41A illustrates that the distal end of the braided member 48 can be unattached to the core 50. The proximal end of the braided member 48 can be attached to the core 50, for example to the first leader 52a, at the proximal braided member anchor 104b. FIG. 41B illustrates that the leaders 52 can train wreck in the catheter 28, for example, when the pusher 30 is translated distally, as shown by arrow, as described herein. The first leader 52a can have a first leader rotation 134a. The second leader 52b can have a second leader rotation 134b in the same or opposite direction as the first leader rotation 134a. The third leader 52c can have a third leader rotation (the third leader 52c is shown in FIG. 41B as unrotated). The leader rotations 134 can be about lateral or transverse axes extending through each respective leader 52a, 52b, or 52c. The leaders 52 can rotate to press the braided member 48 into the catheter 28 at pressure points 137. For example, the core 50 can frictionally drag the braided member 48 at the pressure points 137. The braided member 48 can be taught between the train wreck pressure points 137.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vaso-occlusion system for occluding an aneurysm, the system comprising:
    a delivery catheter extending from a proximal end to a distal end; and
    a vaso-occlusive device within the delivery catheter, wherein the vaso-occlusive device is adapted to be pushed out of, and retrieved back into, the distal end of the delivery catheter, the vaso-occlusive device comprising:
an elongate inner member having a length and a diameter; and
a plurality of distally-open, adjacently arranged outer braided tubular members that are distally pushable out of the delivery catheter, wherein a proximal end of each of the outer braided tubular members is fixed to the elongate inner member but a distal end of each of the outer braided tubular members is not attached to the elongate inner member, further wherein each of the outer braided tubular members has a length that is greater than 5 cm and less than the length, when deployed, of the elongate inner member, and wherein each of the outer braided tubular members has a collapsed configuration when held within the delivery catheter, and expands to an expanded configuration having a diameter of greater than 1.5 times the diameter of the inner member at a distal end of each of the outer braided tubular members when released from the delivery cannula, further wherein each of the outer braided tubular members is formed from about 24 to 36 strands of Nitinol, and each of the outer braided tubular members has a braid angle of 35 degrees or less in the collapsed configuration within the delivery catheter.

2. The vaso-occlusion system of claim 1, further comprising a friction element on the inner member configured to contact both the inner member and one of the braided tubular members when held within the delivery catheter.

3. The vaso-occlusion system of claim 1, wherein the elongate inner member comprises a closed pitch coil.

4. The vaso-occlusion system of claim 1, wherein each of the braided tubular members is formed from a plurality of strands having a thickness that is about 0.0010 inches diameter or less.

5. The vaso-occlusion system of claim 1, wherein the catheter has an inner diameter of between about 0.015 inches and about 0.025 inches.

6. The vaso-occlusion system of claim 1, wherein the each of the outer braided tubular members has an expanded braid angle between about 35-90 degrees when pushed distally out of the delivery catheter.

7. The vaso-occlusion system of claim 1, wherein each of the outer braided tubular member has a pore size formed between strands in the expanded configuration of less than about 0.1 square mm.

8. The vaso-occlusion system of claim 1, wherein an elongate length of the vaso-occlusive device is configured to have a pre-set curve.

9. The vaso-occlusion system of claim 1, further comprising each of the outer braided tubular members are adjacently arranged so that the distal ends of each of the outer braided tubular members is non-overlapping with the proximal ends of an adjacent outer braided tubular members.

10. The vaso-occlusion device of claim 1, wherein the outer braided tubular material is formed from a plurality of strands of Nitinol wire having a thickness that is between about 0.0004 inches and about 0.00075 inches.

11. A vaso-occlusion system for occluding an aneurysm, the system comprising:
a delivery catheter extending from a proximal end to a distal end; and
a vaso-occlusive device within the delivery catheter, wherein the vaso-occlusive device is adapted to be pushed out of, and retrieved back into, the distal end of the delivery catheter, the vaso-occlusive device comprising:
an elongate inner member having a length and a diameter; and
a plurality of distally-open, adjacently arranged outer braided tubular members that are each distally pushable out of the delivery catheter, wherein a proximal end of each of the outer braided tubular members is fixed to the elongate inner member but a distal end of each of the outer braided tubular members is not attached to the elongate inner member, further wherein each of the outer braided tubular members has a length that is greater than 5 cm and less than the length, when deployed, of the elongate inner member, and wherein each of the outer braided tubular members has a collapsed configuration when held within the delivery catheter, and expands to an expanded configuration having a diameter of greater than 1.5 times the diameter of the inner member at a distal end of each of the outer braided tubular members when released from the delivery cannula, further wherein each of the outer braided tubular members is formed from about 24 to 36 strands of Nitinol having a diameter of 0.0010 inches or less, and each of the outer braided tubular members has a braid angle of 30 degrees or less in the collapsed configuration within the delivery catheter and a braid angle in the expanded configuration of 35 degrees or greater.

12. A vaso-occlusion device for occluding an aneurysm, wherein the vaso-occlusive device is adapted to be pushed out of, and retrieved back into, the distal end of a delivery catheter, the vaso-occlusive device comprising:
an elongate inner member having a length and a diameter; and
a plurality of distally-open, adjacently arranged outer braided tubular members that are distally pushable out of the delivery catheter, wherein a proximal end of each of the outer braided tubular members is fixed to the elongate inner member but a distal end of each of the outer braided tubular members is not attached to the elongate inner member, further wherein each of the outer braided tubular members has a length that is greater than 5 cm and less than the length, when deployed, of the elongate inner member, and wherein each of the outer braided tubular members has a collapsed configuration when held within the delivery catheter, and expands to an expanded configuration having a diameter of greater than 1.5 times the diameter of the inner member at a distal end of each of the outer braided tubular members when released from the delivery cannula, further wherein each of the outer braided tubular members is formed from about 24 to 36 strands of Nitinol, and each of the outer braided tubular members has a braid angle of 35 degrees or less in the collapsed configuration within the delivery catheter.

13. The vaso-occlusion device of claim 12, further comprising a friction element on the inner member configured to contact both the inner member and one of the braided tubular members when held within the delivery catheter.

14. The vaso-occlusion device of claim 12, wherein each of the braided tubular members is formed from a plurality of strands having a thickness that is about 0.0010 inches diameter or less.

15. The vaso-occlusion device of claim 12, wherein the each of the outer braided tubular members has an expanded braid angle between about 35-90 degrees when pushed distally out of the delivery catheter.

16. The vaso-occlusion device of claim 12, wherein each of the outer braided tubular member has a pore size formed between strands in the expanded configuration of less than about 0.1 square mm.

17. The vaso-occlusion device of claim 12, wherein an elongate length of the vaso-occlusive device is configured to have a pre-set curve.

18. The vaso-occlusion device of claim 12, further comprising each of the outer braided tubular members are adjacently arranged so that the distal ends of each of the outer braided tubular members is non-overlapping with the proximal ends of an adjacent outer braided tubular members.

19. The vaso-occlusion device of claim 12, wherein the elongate inner member comprises a closed pitch coil.

20. The vaso-occlusion device of claim 12, wherein the outer braided tubular material is formed from a plurality of strands of Nitinol wire having a thickness that is between about 0.0004 inches and about 0.00075 inches.

* * * * *